(12) United States Patent
Laaksonen et al.

(10) Patent No.: US 9,863,965 B2
(45) Date of Patent: *Jan. 9, 2018

(54) LIPIDOMIC BIOMARKERS FOR THE PREDICTION OF CARDIOVASCULAR OUTCOMES IN CORONARY ARTERY DISEASE PATIENTS NOT UNDERGOING STATIN TREATMENT

(71) Applicant: Zora Biosciences OY, Espoo (FI)

(72) Inventors: Reijo Laaksonen, Lempäälä (FI); Kim Ekroos, Helsinki (FI); Reini Hurme, Espoo (FI); Riikka Katainen, Helsinki (FI)

(73) Assignee: Zora Biosciences OY, Espoo (FI)

( * ) Notice: Subject to any disclaimer, the term of this patent is extended or adjusted under 35 U.S.C. 154(b) by 0 days.

This patent is subject to a terminal disclaimer.

(21) Appl. No.: 15/210,048

(22) Filed: Jul. 14, 2016

(65) Prior Publication Data

US 2016/0320418 A1    Nov. 3, 2016

Related U.S. Application Data

(63) Continuation of application No. 14/722,964, filed on May 27, 2015, now Pat. No. 9,423,406, which is a continuation of application No. 14/356,594, filed as application No. PCT/EP2012/071972 on Nov. 7, 2012, now Pat. No. 9,052,328.

(60) Provisional application No. 61/556,909, filed on Nov. 8, 2011.

(30) Foreign Application Priority Data

Nov. 8, 2011    (EP) ..................... 11188328

(51) Int. Cl.
G01N 33/92    (2006.01)

(52) U.S. Cl.
CPC ......... *G01N 33/92* (2013.01); *G01N 2570/00* (2013.01); *G01N 2800/042* (2013.01); *G01N 2800/32* (2013.01); *G01N 2800/324* (2013.01); *G01N 2800/50* (2013.01); *G01N 2800/70* (2013.01)

(58) Field of Classification Search
None
See application file for complete search history.

(56) References Cited

U.S. PATENT DOCUMENTS

2009/0197242 A1    8/2009    Kaddurah-Daouk et al.

FOREIGN PATENT DOCUMENTS

| CA | 2715921 A1 | 9/2009 |
|---|---|---|
| CA | 2741117 A1 | 5/2010 |
| WO | 2009040002 A1 | 4/2009 |
| WO | 2011/063470 | 3/2011 |
| WO | 2011/063048 | 5/2011 |
| WO | 2011/138419 | 11/2011 |
| WO | 2012/136272 | 10/2012 |
| WO | 2013/068374 | 5/2013 |

OTHER PUBLICATIONS

Kasumov et al. (Analytical Biochem 2010 vol. 401 p. 154-161).*
Sullards (Lipid Maps Lipidomics Workshop Apr. 2009).*
Valsecchi et al. (Journal of Lipid Research 2007 vol. 48, p. 417-424).*
International Search Report and Written Opinion dated Jun. 5, 2013 from International Application No. PCT/EP2012/071972, pp. 1-24.
Bergheanu, Sandrin C. et al. Lipidomic approach to evaluate rosuvastatin and atorvastatin at various dosages: investigating differential effects among statins. Current Medicain Rsearch and Opinion, Sep. 1, 2008, vol. 24, No. 9, pp. 1-11.
Kirschenlohr, Heide L. et al. Proton NMR analysis of plasma is a weak predictor of coronary artery disease. Nature Medicine, Jun. 2006, vol. 12, No. 6, pp. 705-710.
Yeo, W. W. et al. Predicting CHD risk in patients with diabetes mellitus. Diabetic Medicine, May 1, 2001, vol. 18, No. 5, pp. 341-344.
Merrill, Alfred H., Jr. et al. Sphingolipidomics: High-throughout, structure-specific, and quantitative analysis of sphingolipids by liquid chromatography tandem mass spectometry. Methods, Jun. 1, 2005, vol. 36, No. 2, pp. 207-224.
Shui, Guanghou et al. Comparative Plasma Lipidome between Human and Cynomolgus Monkey: Are Plasma Polar Lipids Good Biomarkers for Diabetic Monkeys? PLOS ONE, May 2011, vol. 6, Issue 5, pp. 1-12.
Chinese Office Action and Search Report dated Jan. 30, 2015, Chinese Patent Application No. 201280054322.3, filed Nov. 7, 2012, 27 pages (including English translation).

* cited by examiner

*Primary Examiner* — Changhwa J Cheu
(74) *Attorney, Agent, or Firm* — MH2 Technology Law Group, LLP

(57) ABSTRACT

The present invention inter alia provides a method, and use thereof, of predicting severe CVD complications such as AMI or CVD death by detecting the lipid concentrations or lipid ratios of a biological sample and comparing it to a control and has identified specific lipid markers that are more specific and sensitive in predicting these CVD complications than currently utilized clinical markers. Also provided are antibodies towards said lipids, and the use thereof for predicting, diagnosing, preventing and/or treating CVD complications. The invention additionally relates to kits comprising lipids and/or an antibody thereto, for use in the prediction and/or diagnosis of CVD complications.

30 Claims, No Drawings

LIPIDOMIC BIOMARKERS FOR THE PREDICTION OF CARDIOVASCULAR OUTCOMES IN CORONARY ARTERY DISEASE PATIENTS NOT UNDERGOING STATIN TREATMENT

CROSS-REFERENCE TO RELATED APPLICATIONS

This application is a Continuation of Ser. No. 14/722,964 filed 27 May 2015 (allowed), which is a Continuation of Ser. No. 14/356,594 filed on 6 May 2014 (now U.S. Pat. No. 9,052,328), which is the U.S. National Stage application of PCT/EP2012/071972 filed 7 Nov. 2012, which claims priority to European patent application 11188328.6 filed 8 Nov. 2011 and U.S. Provisional Patent Application 61/556,909 filed 8 Nov. 2011, the entire disclosures of which are hereby incorporated herein by reference in their entireties.

DESCRIPTION

Field of the Invention

This invention relates to methods and uses involving lipid levels to predict and prevent severe cardiovascular disease-associated fatal complications. The invention thus provides a means to identify and treat high-risk coronary artery disease patients. The methods include analyzing lipid levels of a biological sample, and comparing it to a control.

Background of the Invention

Worldwide, cardiovascular diseases (CVD) are among the leading causes of mortality and morbidity with ever-increasing prevalence. CVD is used to classify numerous conditions that affect the heart, heart valves, blood, and vasculature of the body. One of these conditions is coronary artery disease (CAD). Statins are a family of cholesterol lowering drugs for people at high risk of cardiovascular complications. Statins are widely used, as alone in the USA there are almost 20 million statin treated patients and it has been calculated that some 50 million patients would benefit of statin treatment in the USA. However, despite statin treatment the CVD patients have risk to develop severe CVD complications. Early targeted initiation of preventive measures of CVD-related fatal complications, such as acute myocardial infarction (AMI) and death, would be of great benefit and can provide a major opportunity in reducing mortality and morbidity in patients suffering from CVD. To this end, accurate identification of individuals who are at risk of developing CVD complications is essential. However, traditional risk assessment fails to recognize a substantial proportion of patients at high risk while a large proportion of individuals are classified as having intermediate risk, leaving patient management uncertain. Additional strategies to further refine risk assessment of high-risk CVD are therefore highly needed. To this end, the inventors have evaluated the role of novel lipidomic biomarkers as a prognostic tool for fatal cardiovascular events in CVD patients.

Statins are widely used drugs to prevent atherosclerotic end points in CVD patients and, therefore, a significant portion of middle aged population is being treated with statins. Statins do lower efficiently LDL-cholesterol and also many other lipids in the circulation. Thus, statin treatment is significantly affecting plasma concentrations of many potential lipidomic markers and therefore it is important to separately study lipidomic biomarkers in subjects on statin treatment and without statin treatment. It is known in the clinical practice that conventional lipid biomarkers such as LDL-cholesterol are not informative in statin treated patients, but these patients may still have a substantial residual risk of CAD complications despite statin treatment. This current invention deals with subjects who are not undergoing statin treatment at the time of the risk evaluation. A novel innovative aspect here is that the investigators are studying risk markers separately in patients with type 2 Diabetes (DM2). DM2 is causing numerous metabolic alterations in the human body and, therefore, DM2 may affect plasma levels of lipidomic biomarkers as well. Furthermore, CVD risk lipids in non-DM2 patients and DM2 patients may not be the same and the prognostic accuracy can potentially be greatly improved if these subject groups are studied separately.

Plasma or serum total cholesterol, LDL-cholesterol or HDL-cholesterol concentrations have been used as gold standard biomarkers for CVD/CAD risk prediction. However, a number of coronary artery disease (CAD) or acute myocardial infarction (AMI) patients have LDL-C levels within the recommended range suggesting the need for additional diagnostic measures of the residual risk. It is evident from earlier large scale population studies that these measurements associate with the CAD risk and CAD endpoints such as AMI or cardiovascular death. Therefore, preventive treatment strategies have so far been addressed to lower LDL-C concentrations (mainly by statin treatment) and more recently also attempts to raise HDL-C have been made (e.g., by CETP-inhibitors). On the other hand, it has also been observed that one half of the AMI patients actually do have normal LDL cholesterol levels and that there is a substantial residual risk in statin treated patients despite a LDL-C lowering. Furthermore, recent publications have demonstrated that plasma levels of apolipoprotein B (apoB), the main surface protein on LDL particles, and LDL-C, the amount of cholesterol in those particles, are correlated and, considered separately, as positive risk factors. Plasma levels of apolipoprotein $A_1$, the main surface protein on HDL particles, and HDL-C, the amount of cholesterol in those particles, are also correlated with each other and, considered separately, as negative risk factors. Importantly, for a given usual apoB, lower LDL-C has been observed to associate with a higher risk of AMI supporting the view that, on average, LDL particles with low cholesterol content per particle (small, dense LDL particles) are particularly hazardous. Thus, it seems possible that LDL-C associates directly with the more dangerous molecules carried by LDL-particles and that LDL-C is only an indirect measurement of the risk. Therefore, it is of importance to search for molecules e.g., certain lipid species that are directly related with hazardous (i.e., fatal) cardiovascular events.

Lipid metabolite imbalance is a probable cause of dyslipidemia and the ensuing atherosclerosis manifested in its gravest form as the vulnerable atherosclerotic plaque. Atherosclerotic plaques are complex molecular formations that contain numerous lipids. However, there are other factors than lipid rich plaques or LDL cholesterol that make lipids an attractive group of molecules for CVD studies. Lipids are tightly regulated which makes Lipidomic data robust and informative on the current state of the studied organism. Also, lipids are one of the culmination points of a biological system, more the true outcome than the predictor. Combining Lipidomic data with appropriate biobanked clinical material presents a good opportunity for biomarker discovery. Moreover, lipidomics can be used as a gauge of efficacy and safety in drug development and evolving theragnostics. Lipidomic biomarkers are prime candidates for true companion diagnostics in the CVD area and present many opportunities for improved translational medicine as well.

The plaque building blocks and lipoprotein components that are thought to traffic lipids to the site of lesion formation can now be resolved with Lipidomic studies correlating lipid structure and composition to function and thereby disease pathogenesis. The number of lipid mediators in the human body is overwhelming. Their identification and quantification is facilitated by the advances in mass spectrometry and lipid biochemistry, which enable the simultaneous high throughput identification and quantification of hundreds of molecular lipid species in several lipid classes (Ejsing C S, et al: *Global analysis of the yeast lipidome by quantitative shotgun mass spectrometry. Proc Natl Acad Sci USA* 2009, 106:2136-2141; Stahlman M, et al: *High-throughput shotgun lipidomics by quadrupole time-of-flight mass spectrometry. J Chromatogr B Analyt Technol Biomed Life Sci* 2009 Hiukka A, et al: *ApoCIII-enriched LDL in type 2 diabetes displays altered lipid composition, increased susceptibility for sphingomyelinase, and increased binding to biglycan. Diabetes* 2009, 58:2018-2026; Linden D, et al: *Liver-directed overexpression of mitochondrial glycerol-3-phosphate acyltransferase results in hepatic steatosis, increased triacylglycerol secretion and reduced fatty acid oxidation. FASEB J* 2006, 20:434-443.) collectively referred to as the lipidome. Lipidomic studies identify lipid cellular distribution and describe their biochemical mechanisms, interactions and dynamics. Importantly, lipidomics quantifies the exact chemical composition of lipidomes (Han X, Gross R W: *Global analyses of cellular lipidomes directly from crude extracts of biological samples by ESI mass spectrometry: a bridge to lipidomics. J Lipid Res* 2003, 44:1071-1079).

Due to both high sensitivity and selectivity of lipidomics, even the smallest sample amounts can be analyzed today. The bulk of the lipid data in the art today presents lipids in a sum composition format, i.e. phosphatidylcholine (PC) 34:1 (Brugger B, et al: *Quantitative analysis of biological membrane lipids at the low picomole level by nano-electrospray ionization tandem mass spectrometry. Proc Natl Acad Sci USA* 1997, 94:2339-2344) where the molecular lipid and the attached fatty acid tails remain unidentified. The identification of molecular lipid species, e.g., PC 16:0/18:1 (Ekroos K, et al: *Charting molecular composition of phosphatidylcholines by fatty acid scanning and ion trap MS3 fragmentation. J Lipid Res* 2003, 44:2181-2192) is the main feature of advanced lipidomics, which delivers highly resolved molecular lipid species rather than summed fatty acid information. For example, the information of the type of fatty acids and their positions of attachment to the glycerol backbone making up the particular PC molecule is revealed. There are conventional techniques such as thin-layer chromatography combined with gas chromatography but they not only require considerably larger sample amounts and laborious sample preparation, but they do not deliver the molecular lipid species. Despite multiple mass spectrometry techniques capable of characterizing lipid entities, most of them are still unable to deliver reliable high-quality quantitative data in terms of absolute or close-to absolute concentrations. In the context of the present invention, electrospray ionization mass spectrometry-based lipidomics is the preferred technology and can utilize both shotgun and targeted lipidomics for exhaustive deciphering and precise quantification of molecular lipidomes. The superior quality and specificity of shotgun and targeted lipidomics will meet stringent regulatory standards, such as good laboratory practice guidelines (GLP) when set-up in the proper environment. Using these technologies quantification of up to two thousand molecular lipids is possible even in a high throughput format.

Lipidomics is a tool for differentiating patients based on their molecular lipid profiles. Personalized medicine and diagnostics enabled by lipidomics will facilitate the mission of the right individual receiving the right drug at the right time and dose. Several works employing analytes consisting of lipids, proteins and hydrophilic molecules among many others have been conducted to meet the needs of personalized medicine. Recently, non-hypothesis-driven metabolomic screenings have been used to identify novel CVD biomarkers.

For example, WO2004/038381 discloses a method for metabolomically facilitating the diagnosis of a disease state of a subject, or for predicting whether a subject is predisposed to having a disease state wherein the small molecule profile from a subject is obtained and compared to a standard small molecule profile.

WO2008/148857 discloses a method to assess the risk of cardiovascular disease in a patient (including atherosclerosis) by isolating the HDL fraction and sub-fraction from a blood sample of the patient. The components of the HDL fraction or sub-fraction to be measured were Sphingosine-1-Phosphate (S1P), sphingomyelin (SM) and Apolipoprotein A-I (apoA-1).

WO2008/11943 further discloses markers for detecting coronary artery disease that can indicate a patient at risk of having or developing coronary artery disease. These include 15 "first-choice" molecules which were: C18:3 Cholesterol ester, C32:1 Phosphatidylcholine, Alanine, Lipid (mainly VLDL), Lysine, Hexadecanoic acid, C36:2 Phosphatidylcholine, Formate, C32:2 Phosphatidylcholine, C18:2 (Linoleic Acid), Cholesterol, C 18:2 Lyso-phosphatidylcholine, C36:3 Phosphatidylcholine, C34:4 Phosphatidylcholine and C34:3 Phosphatidylcholine.

Furthermore, US2007/0099242 describes a method to determine if a subject is at risk to develop, or is suffering from cardiovascular disease. The method involves determining a change in the amount of a biomarker in the biological sample or HDL sub-fraction thereof, compared to a control sample, wherein the biomarker is at least one of Apolipoprotein C-IV ("ApoC-IV"), Paraoxonase 1 ("PON-1"), Complement Factor 3 ("C3"), Apolipoprotein A-IV ("ApoA-IV"), Apolipoprotein E ("ApoE"), Apolipoprotein LI ("ApoL1"), Complement Factor C4 ("C4"), Complement Factor C4B1 ("C4B1"), Histone H2A, Apolipoprotein C-II ("ApoC-II"), Apolipoprotein M ("ApoM"), Vitronectin, Haptoglobin-related Protein and Clusterin. The document also discloses a method for detecting the presence of one or more atherosclerotic lesions wherein a change in the amount of a biomarker in the biological sample or HDL sub-fraction thereof is detected, compared to a control sample and wherein the biomarker is selected from PON-1, C3, C4, ApoE, ApoM and C4B1. All biomarkers mentioned in this document are protein or lipoprotein biomarkers.

WO2011/063470 compares the lipid profiles of patients with coronary disease (stable) with patients with acute coronary syndrome (ACS) having acute chest pain, ECG changes and troponin I elevations. This comparison revealed lipid markers that associate with troponin I and clinical markers of ACS suggesting that lipids may be used as a biomarker of acute myocardial ischemia. However, in acute cardiovascular setting, troponin I seems to be superior marker compared to lipid profiles (Meikle et al. *Plasma lipidomic analysis of stable and unstable coronary artery disease. Arterioscler Thromb Vasc Biol.* 2011 November;

31(11):2723-32.) and the findings do not predict patient outcome nor long-term risk of acute myocardial ischemia or cardiovascular death.

From previous work it cannot be extrapolated that lipid analysis will yield by default a CVD biomarker predictive to the fatal outcomes associated with CVD/CAD. There remains a need for specific markers useful for identifying specific risk patient populations within patients generally suffering from or being at risk of CVD/CAD.

The present invention identifies biomarkers of high risk CVD by absolute, or close to absolute, quantification of defined molecular lipid species instead of profiling multiple analytes. Importantly, while many of the existing biomarker candidates are composite fingerprints of multiple factors, the lipidomics approach herein shows value already at a level of single species or ratios thereof. The present application discloses an improved lipid assay approach over those in the prior art since it takes into account factors that affect lipid metabolism such as lipid lowering treatment (e.g. statins) and diabetes. Therefore, the present application provides novel personalized prediction markers.

SUMMARY OF THE INVENTION

The present invention provides novel lipidomic markers for predicting and preventing severe CVD/CAD-associated complications, including AMI, stroke and death, in CVD/CAD patients not undergoing statin treatment. These markers thus provide a means to identify and treat high-risk coronary artery disease patients. Specifically, it has been found that the lipid molecules, lipid-lipid concentration ratios and lipid-clinical concentration ratios provided herein, when displaying an increased or decreased level—as the case may be—in samples from CAD patients, are useful lipidomic markers for the methods and uses in accordance with the present invention. These sensitive and specific markers were specifically tested to display superior diagnostic and prognostic value compared to the current clinically-used markers predictive for CVD/CAD outcomes. In fact, the currently available biomarkers such as LDL-C or HDL-C have only very limited or no value in predicting the CVD death risk in CAD patients. The present invention therefore represents a significant advantage to other markers which are currently used to diagnose and/or predict CVD and CVD complications, which include LDL-C, total plasma/serum cholesterol and Apolipoprotein B and A1. Thus, the lipidomic markers provided herein allow better diagnosis of or assessment of the risk to develop major CVD complications such as AMI or CVD death.

In accordance with the present invention, methods are inter alia disclosed herein for determining the risk of a CVD patient not undergoing statin treatment to develop CVD complications, or for determining warning signs of CVD risks, (including death, myocardial infarction (MI), angina pectoris, transischemic attack (TIA) and stroke) in said patient.

Methods according to the invention typically comprise the steps of: a) providing a biological sample from a CAD subject; b) determining a lipid concentration, lipid-lipid concentration ratio, or lipid-clinical concentration ratio or (a) corresponding profile(s) from said sample (i.e., determining information on a lipidomic marker in accordance with the invention); and c) comparing said determined lipid concentration, lipid-lipid concentration ratio, or lipid-clinical concentration ratio or said corresponding profile(s) to the corresponding lipid concentration, lipid-lipid concentration ratio, or lipid-clinical concentration ratio or the corresponding profile(s) in a control.

As mentioned above, the lipidomic marker to be compared between the subject sample and the control (or control sample) may be one or more of the lipid concentration(s), lipid-lipid concentration ratio(s), or lipid-clinical concentration ratio(s) or combinations thereof, i.e., the corresponding profile(s), as described and claimed herein. In this regard, the control or control sample allows establishment of the lipidomic marker baseline or starting point.

The lipidomic markers of the present invention allow for prediction and prevention of fatal CVD complications. This will facilitate earlier intervention, less symptom development and suffering and decreased morbidity/mortality associated with CVD. Thus, the lipidomic markers described and claimed herein allow for individual tailoring of drug intervention for patients being at risk to develop major CVD complications.

In other words, the present invention discloses diagnostic and/or predictive lipid markers and lipid-lipid or lipid-clinical concentration ratios for use in predicting CVD complications such as AMI or CVD death in CVD patients who are not undergoing statin treatment. The invention uses the measurement of lipid concentrations, lipid-lipid and/or lipid-clinical concentration ratios to determine the risk of said subject to develop CVD complications such as AMI and/or CVD death. The subject may have previously suffered from a cardiovascular disease event such as angina pectoris, myocardial infarction or stroke.

Accordingly, in one aspect of the invention, a method is provided for determining whether a subject who is not undergoing statin treatment is at risk to develop one or more CVD complications such as AMI and/or CVD death, said method comprising determining in a sample from said subject one or more lipid-lipid concentration ratio(s), wherein (an) increased or decreased lipid-lipid concentration ratio(s) in said sample, when compared to a control sample, is (are) indicative of said subject having an increased risk of developing one or more CVD complications, such as AMI or CVD death, wherein the one or more lipid-lipid concentration ratio(s) whose increase(s) is (are) compared to the control is (are) selected from: Cer(d18:1/18:0)/Cer(d18:1/24:0), Cer(d18:1/20:0)/Cer(d18:1/24:0), Cer(d18:1/22:0)/Cer(d18:1/24:0) Gb3(d18:1/16:0)/PC 18:0/22:6, SM (d18:1/16:0) (d18:1/15:1-OH)/SM (d18:1/24:0) (d18:1/23:1-OH) (Table 3);
and wherein the one or more lipid-lipid concentration ratio(s) whose decrease(s) is (are) compared to the control is (are) selected from: Cer(d18:1/24:0)/PC 16:0/18:2, SM (d18:1/24:0) (d18:1/23:1-OH)/SM (d18:1/24:1) (d18:1/23:2-OH), Cer(d18:1/24:0)/Cer(d18:1/24:1), Cer(d18:1/24:0)/SM (d18:1/14:0) (d18:1/13:1-OH), Cer(d18:1/24:0)/Gb3 (d18:1/16:0) and Cer(d18:1/24:0)/SM (d18:1/16:1) (d18:1/15:2-OH) (Table 3).

In one particular embodiment, the one or more lipid-lipid concentration ratio(s) whose decrease(s) is (are) compared to the control is (are) selected from: Cer(d18:1/24:0)/PC 16:0/18:2, SM (d18:1/24:0) (d18:1/23:1-OH)/SM (d18:1/24:1) (d18:1/23:2-OH), Cer(d18:1/24:0)/SM (d18:1/14:0) (d18:1/13:1-OH), Cer(d18:1/24:0)/Gb3(d18:1/16:0) and Cer(d18:1/24:0)/SM (d18:1/16:1) (d18:1/15:2-OH) (Table 3).

In yet another alternative embodiment, the present invention relates to a method for determining whether a subject who is not undergoing statin treatment is at risk to develop one or more CVD complications, such as AMI and/or CVD death, comprising determining in a sample from said subject one or more lipid-clinical concentration ratio(s), wherein (an) increased or decreased lipid-clinical concentration ratio(s) in said sample, when compared to a control sample, is (are) indicative of said subject having an increased risk of developing one or more CVD complications, such as AMI or CVD death, wherein the one or more lipid-clinical concentration ratio(s) whose increase(s) is (are) compared to the control is (are) selected from: GlcCer(d18:1/16:0)/total cholesterol, Gb3(d18:1/16:0)/apolipoprotein A-I, Gb3(d18:1/18:0)/apolipoprotein A-I, Gb3(d18:1/16:0)/HDL cholesterol and PC 16:0/18:2/total cholesterol (Table 3);

and wherein the one or more lipid-clinical concentration ratio(s) whose decrease(s) is (are) compared to the control is (are) selected from: Cer(d18:1/24:0)/supersensitive C-reactive protein and PC 18:0/22:6/supersensitive C-reactive protein (Table 3).

For the purposes of the invention, and particularly for lipid-clinical concentration ratios, an Apolipoprotein A-I measurement may alternatively be an Apolipoprotein A-II measurement.

In another aspect of the invention, a method is provided for determining whether a subject not undergoing statin treatment who is not suffering from type 2 diabetes mellitus is at risk to develop one or more CVD complications, such as acute myocardial infarction (AMI) and/or CVD death, said method comprising determining in a sample from said subject the concentration(s) of one or more lipid(s), wherein (an) increased or decreased concentration(s) in said sample, when compared to a control sample, is (are) indicative of said subject having an increased risk of developing one or more CVD complications, such as AMI or CVD death, wherein the one or more lipid(s) whose increase(s) in concentration is (are) compared to the control is (are) selected from: CE 19:1 oxCE 682.6, GlcCer(d18:1/16:0), SM (d18:1/18:1), CE 20:4, LacCer(d18:1/16:0), Cer 18:1/16:0, SM 18:1/16:0 and CE 16:0 (Tables 4a, 6 and 8);

and wherein the one or more lipid(s) whose decrease(s) in concentration is (are) compared to the control is (are) selected from: PC 18:0/22:6, SM (d18:1/23:1) (d18:1/22:2-OH), PC 16:0/22:6, SM 18:1/24:0 and LPC 16:0 (Tables 4a, 6 and 8).

In one particular embodiment, the one or more lipid(s) whose increase(s) in concentration is (are) compared to the control is (are) selected from: CE 19:1 (oxCE 682.6), CE 20:4, Cer 18:1/16:0 and SM 18:1/16:0 (Tables 4a, 6 and 8); and wherein the one or more lipid(s) whose decrease(s) in concentration is (are) compared to the control is (are) selected from: PC 18:0/22:6, SM 18:1/24:0 and LPC 16:0 (Tables 4a, 6 and 8).

In a preferred embodiment, the one or more lipid(s) whose increase(s) in concentration is (are) compared to the control is (are) selected from: GlcCer(d18:1/16:0), CE 20:4, LacCer (d18:1/16:0), Cer 18:1/16:0, SM 18:1/16:0 and CE 16:0 (Table 8);

and the one or more lipid(s) whose decrease(s) in concentration is (are) compared to the control is (are) selected from: PC 16:0/22:6, SM 18:1/24:0 and LPC 16:0 (Table 8).

In one particularly preferred embodiment, the one or more lipid(s) whose increase(s) in concentration is (are) compared to the control is (are) selected from: CE 20:4, Cer 18:1/16:0 and SM 18:1/16:0 (Table 8); and the one or more lipid(s) whose decrease(s) in concentration is (are) compared to the control is (are) selected from: SM 18:1/24:0 and LPC 16:0 (Table 8).

In an alternative embodiment, the present invention relates to a method for determining whether a subject not undergoing statin treatment who is not suffering from type 2 diabetes mellitus is at risk to develop one or more CVD complications such as AMI and/or CVD death, comprising determining in a sample from said subject one or more lipid-lipid concentration ratio(s), wherein (an) increased or decreased lipid-lipid concentration ratio(s) in said sample, when compared to a control sample, is (are) indicative of said subject having an increased risk of developing one or more CVD complications, such as AMI or CVD death, wherein the one or more lipid-lipid concentration ratio(s) whose increase(s) is (are) compared to the control is (are) selected from: Cer(d18:1/18:0)/SM (d18:1/23:1) (d18:1/22:2-OH), Cer(d18:1/16:0)/PC 18:0/22:6, Cer(d18:1/18:0)/PC 16:0/22:6, GlcCer(d18:1/16:0)/PC 18:0/22:6, GlcCer(d18:1/18:0)/SM (d18:1/23:1) (d18:1/22:2-OH), Cer(d18:1/16:0)/PC 16:0/22:6, Cer(d18:1/20:0)/SM (d18:1/23:1) (d18:1/22:2-OH), GlcCer(d18:1/18:0)/PC 16:0/22:6, SM (d18:1/18:1)/SM (d18:1/23:1) (d18:1/22:2-OH), Cer(d18:1/20:0)/PC 16:0/22:6, SM (d18:1/16:0) (d18:1/15:1-OH)/SM (d18:1/23:1) (d18:1/22:2-OH), SM (d18:1/15:0) (d18:1/14:1-OH)/SM (d18:1/23:1) (d18:1/22:2-OH), GlcCer(d18:1/20:0)/SM (d18:1/23:1) (d18:1/22:2-OH), Cer(d18:1/24:1)/PC 18:0/22:6, SM (d18:1/16:1) (d18:1/15:2-OH)/SM (d18:1/23:1) (d18:1/22:2-OH), GlcCer(d18:1/16:0)/PC 16:0/22:6, LacCer (d18:1/22:0)/PC 16:0/22:6, LacCer(d18:1/22:0)/SM (d18:1/23:1) (d18:1/22:2-OH), GlcCer(d18:1/20:0)/PC 16:0/22:6, CE 16:0/PC 18:0/22:6, Cer(d18:1/22:0)/PC 18:0/22:6, CE 18:2/PC 18:0/22:6, CE 18:1/PC 18:0/22:6, Cer(d18:1/16:0)/Cer(d18:1/24:0), Gb3(d18:1/16:0)/PC 16:0/22:6, CE 20:4/PC 18:0/22:6, CE 22:6/PC 18:0/22:6, PC 16:0/16:0/PC 16:0/22:6, CE 16:0/PC 16:0/22:6, CE 18:2/PC 16:0/22:6, Gb3(d18:1/24:0)/PC 16:0/22:6, CE 18:1/PC 16:0/22:6, CE 20:4/PC 16:0/22:6, SM (d18:1/16:1) (d18:1/15:2-OH)/SM (d18:1/24:0) (d18:1/23:1-OH), Cer(d18:1/16:0)/Cer(d18:1/22:0), CE 16:0/Cer(d18:1/24:0), SM (d18:1/18:1)/SM (d18:1/24:0) (d18:1/23:1-OH), GlcCer(d18:1/18:0)/SM (d18:1/24:0) (d18:1/23:1-OH) and SM (d18:1/15:0) (d18:1/14:1-OH)/SM (d18:1/24:0) (d18:1/23:1-OH)(Table 4b);

and wherein the one or more lipid-lipid concentration ratio(s) whose decrease(s) is (are) compared to the control is (are) selected from: Cer(d18:1/24:0)/GlcCer(d18:1/18:0), Cer(d18:1/24:0)/GlcCer(d18:1/16:0), PC 16:0/22:6/SM (d18:1/16:0) (d18:1/15:1-OH), PC 18:0/22:6/SM (d18:1/14:0) (d18:1/13:1-OH), PC 16:0/22:6/SM (d18:1/16:1) (d18:1/15:2-OH), PC 18:0/22:6/SM (d18:1/16:0) (d18:1/15:1-OH), PC 18:0/22:6/SM (d18:1/15:0) (d18:1/14:1-OH), PC 18:0/22:6/SM (d18:1/18:0), PC 18:0/22:6/SM (d18:1/16:1) (d18:1/15:2-OH) and PC 18:0/22:6/SM (d18:1/18:1) (Table 4b).

In a preferred embodiment, the one or more lipid-lipid concentration ratio(s) whose increase(s) is (are) compared to the control is (are) selected from: Cer(d18:1/18:0)/SM (d18:1/23:1) (d18:1/22:2-OH), Cer(d18:1/16:0)/PC 18:0/22:6, Cer(d18:1/18:0)/PC 16:0/22:6, GlcCer(d18:1/16:0)/PC 18:0/22:6, GlcCer(d18:1/18:0)/SM (d18:1/23:1) (d18:1/22:2-OH), Cer(d18:1/16:0)/PC 16:0/22:6, Cer(d18:1/20:0)/SM (d18:1/23:1) (d18:1/22:2-OH), GlcCer(d18:1/18:0)/PC 16:0/22:6, SM (d18:1/18:1)/SM (d18:1/23:1) (d18:1/22:2-OH), Cer(d18:1/20:0)/PC 16:0/22:6, SM (d18:1/16:0) (d18:1/15:1-OH)/SM (d18:1/23:1) (d18:1/22:2-OH), SM (d18:1/15:0) (d18:1/14:1-OH)/SM (d18:1/23:1) (d18:1/22:2-OH), GlcCer(d18:1/20:0)/SM (d18:1/23:1) (d18:1/22:2-OH), Cer (d18:1/24:1)/PC 18:0/22:6, SM (d18:1/16:1) (d18:1/15:2-OH)/SM (d18:1/23:1) (d18:1/22:2-OH), GlcCer(d18:1/16:0)/PC 16:0/22:6, LacCer(d18:1/22:0)/PC 16:0/22:6, CE 16:0/PC 18:0/22:6, CE 18:2/PC 18:0/22:6 and Cer(d18:1/16:0)/Cer(d18:1/24:0) (Table 6);

and the one or more lipid-lipid concentration ratio(s) whose decrease(s) is (are) compared to the control is (are) selected from: PC 18:0/22:6/SM (d18:1/16:1) (d18:1/15:2-OH) and PC 18:0/22:6/SM (d18:1/18:1)(Table 6).

In yet another alternative embodiment the present invention relates to a method for determining whether a subject not undergoing statin treatment who is not suffering from type 2 diabetes mellitus is at risk to develop one or more CVD complications, such as AMI and/or CVD death, comprising determining in a sample from said subject one or more lipid-clinical concentration ratio(s), wherein (an) increased or decreased lipid-clinical concentration ratio(s) in said sample, when compared to a control sample, is (are) indicative of said subject having an increased risk of developing one or more CVD complications, such as AMI or CVD death, wherein the one or more lipid-clinical concentration ratio(s) whose increase(s) is (are) compared to the control is (are) selected from: Cer(d18:1/16:0)/HDL cholesterol, GlcCer(d18:1/16:0)/apolipoprotein A-I, CE 19:1 oxCE 682.6/apolipoprotein A-I, GlcCer(d18:1/18:0)/apolipoprotein A-I, GlcCer(d18:1/18:0)/HDL cholesterol, GlcCer(d18:1/16:0)/HDL cholesterol, GlcCer(d18:1/20:0)/apolipoprotein A-I, GlcCer(d18:1/18:0)/total cholesterol and Cer(d18:1/16:0)/apolipoprotein B (Table 4c);

and wherein the one or more lipid-clinical concentration ratio(s) whose decrease(s) is (are) compared to the control is (are) selected from: LacCer(d18:1/24:0)/supersensitive C-reactive protein, CE 17:1/supersensitive C-reactive protein, SM (d18:1/16:0) (d18:1/15:1-OH)/supersensitive C-reactive protein, GlcCer(d18:1/24:0)/supersensitive C-reactive protein, Gb3(d18:1/22:0)/supersensitive C-reactive protein, PC 18:0/20:3/apolipoprotein B, PC 16:0/16:1/supersensitive C-reactive protein, PC 16:0/22:6/total cholesterol, PC 16:0/22:6/apolipoprotein B, PC 18:1/18:1/supersensitive C-reactive protein, SM (d18:1/24:1) (d18:1/23:2-OH)/supersensitive C-reactive protein, PC 18:0/18:2/supersensitive C-reactive protein, Cer(d18:1/24:1)/supersensitive C-reactive protein, Cer(d18:1/22:0)/supersensitive C-reactive protein, PC 18:0/22:6/triglycerides, SM (d18:1/18:0)/supersensitive C-reactive protein, PC 18:0/20:3/supersensitive C-reactive protein, SM (d18:1/24:0) (d18:1/23:1-OH)/supersensitive C-reactive protein, PC 16:0/18:1/supersensitive C-reactive protein, SM (d18:1/23:1) (d18:1/22:2-OH)/total cholesterol, PC 18:0/22:6/LDL cholesterol, PC 18:0/22:6/total cholesterol, SM (d18:1/23:1) (d18:1/22:2-OH)/LDL cholesterol, SM (d18:1/23:1) (d18:1/22:2-OH)/apolipoprotein B, PC 18:0/22:6/apolipoprotein B, SM (d18:1/23:0) (d18:1/22:1-OH)/supersensitive C-reactive protein, PC 18:0/18:1/supersensitive C-reactive protein, LPC 16:0/supersensitive C-reactive protein, PC 16:0/22:6/supersensitive C-reactive protein, SM (d18:1/23:1) (d18:1/22:2-OH)/supersensitive C-reactive protein, PC 18:0/22:6/lipoprotein(a) and PC 16:0/18:0/supersensitive C-reactive protein (Table 4c).

In one particular embodiment, the one or more lipid-clinical concentration ratio(s) whose increase(s) is (are) compared to the control is (are) selected from: CE 19:1 oxCE 682.6/apolipoprotein A-I, GlcCer(d18:1/18:0)/HDL cholesterol, GlcCer(d18:1/16:0)/HDL cholesterol, GlcCer(d18:1/20:0)/apolipoprotein A-I and GlcCer(d18:1/18:0)/total cholesterol (Table 4c).

In a preferred embodiment, the one or more lipid-clinical concentration ratio(s) whose increase(s) is (are) compared to the control is (are) selected from: Cer(d18:1/16:0)/HDL cholesterol (Table 6);

and/or the one or more lipid-clinical concentration ratio(s) whose decrease(s) is (are) compared to the control is (are) selected from: PC 18:0/22:6/LDL cholesterol, PC 18:0/22:6/total cholesterol and PC 18:0/22:6/apolipoprotein B (Table 6).

In another aspect of the invention, a method is provided for determining whether a subject not undergoing statin treatment who is suffering from type 2 diabetes mellitus is at risk to develop one or more CVD complications, such as acute myocardial infarction (AMI) and/or CVD death, said method comprising determining in a sample from said subject the concentration(s) of one or more lipid(s), wherein (an) increased or decreased concentration(s) in said sample, when compared to a control sample, is (are) indicative of said subject having an increased risk of developing one or more CVD complications, such as AMI or CVD death, wherein the one or more lipid(s) whose increase(s) in concentration is (are) compared to the control is (are) selected from: Gb3(d18:1/24:1), Gb3(d18:1/16:0), GlcCer 18:1/16:0, LacCer 18:1/16:0 and PC 16:0/22:6 (Tables 5a, 7 and 8);

and wherein the one or more lipid(s) whose decrease(s) in concentration is (are) compared to the control is (are) selected from: PC O-16:0/20:4-alkyl, CE 20:4, CE 18:0, CE 14:0, CE 22:6, CE 18:3, GlcCer 18:1/18:0 and SM 18:1/24:0 (Tables 5a, 7 and 8).

In one particular embodiment, the one or more lipid(s) whose increase(s) in concentration is (are) compared to the control is (are) selected from: Gb3(d18:1/24:1), Gb3(d18:1/16:0), GlcCer 18:1/16:0 and LacCer 18:1/16:0 (Tables 5a, 7 and 8);

and wherein the one or more lipid(s) whose decrease(s) in concentration is (are) compared to the control is (are) selected from: PC O-16:0/20:4-alkyl, CE 20:4, CE 22:6, GlcCer 18:1/18:0 and SM 18:1/24:0 (Tables 5a, 7 and 8).

In a preferred embodiment, the one or more lipid(s) whose increase(s) in concentration is (are) compared to the control is (are) selected from: Gb3 18:1/16:0, GlcCer 18:1/16:0, LacCer 18:1/16:0 and PC 16:0/22:6 (Table 8);

and the one or more lipid(s) whose decrease(s) in concentration is (are) compared to the control is (are) selected from: CE 14:0, CE 22:6, CE 18:3, GlcCer 18:1/18:0 and SM 18:1/24:0 (Table 8).

In one particularly preferred embodiment, the one or more lipid(s) whose increase(s) in concentration is (are) compared to the control is (are) selected from: Gb3 18:1/16:0, GlcCer 18:1/16:0 and LacCer 18:1/16:0 (Table 8);

and the one or more lipid(s) whose decrease(s) in concentration is (are) compared to the control is (are) selected from: CE 22:6, GlcCer 18:1/18:0 and SM 18:1/24:0 (Table 8).

In an alternative embodiment, the present invention relates to a method for determining whether a subject not undergoing statin treatment who is suffering from type 2 diabetes mellitus is at risk to develop one or more CVD complications such as AMI and/or CVD death, comprising determining in a sample from said subject one or more lipid-lipid concentration ratio(s), wherein (an) increased or decreased lipid-lipid concentration ratio(s) in said sample, when compared to a control sample, is (are) indicative of said subject having an increased risk of developing one or more CVD complications, such as AMI or CVD death, wherein the one or more lipid-lipid concentration ratio(s) whose increase(s) is (are) compared to the control is (are) selected from: Gb3(d18:1/24:1)/SM (d18:1/17:0) (d18:1/16:1-OH), Gb3(d18:1/24:1)/PC O-16:0/20:4-alkyl, Gb3(d18:1/16:0)/SM (d18:1/17:0) (d18:1/16:1-OH), Gb3(d18:1/24:1)/GlcCer(d18:1/24:0), Gb3(d18:1/24:1)/GlcCer(d18:1/22:0) and Gb3(d18:1/22:0)/SM (d18:1/17:0) (d18:1/16:1-OH) (Table 5b);

and wherein the one or more lipid-lipid concentration ratio(s) whose decrease(s) is (are) compared to the control is (are) selected from: CE 18:0/PC 18:0/18:2, PC 18:0/18:2/PE 18:0/18:2, Cer(d18:1/24:0)/PE 18:0/18:2, CE 18:0/CE 18:1, CE 18:2/Gb3(d18:1/16:0), CE 16:0/Gb3(d18:1/16:0), CE 18:0/PC 16:0/22:6, CE 14:0/Gb3(d18:1/24:0), CE 18:0/SM (d18:1/16:0) (d18:1/15:1-OH), CE 18:3/SM (d18:1/14:0) (d18:1/13:1-OH), CE 18:0/PC 16:0/18:2, Cer(d18:1/24:0)/PC O-16:0/18:1-alkyl, CE 18:0/Gb3(d18:1/24:0), CE 18:3/PC 16:0/18:1, PC 18:0/20:3/PC O-16:0/18:1-alkyl, CE 14:0/PC 16:0/16:0, CE 17:1/Gb3(d18:1/16:0), CE 14:0/SM (d18:1/14:0) (d18:1/13:1-OH), PC 18:0/20:3/PE 18:0/18:2, CE 18:0/SM (d18:1/14:0) (d18:1/13:1-OH), CE 14:0/PC 16:0/18:1, CE 18:0/SM (d18:1/24:1) (d18:1/23:2-OH), CE 18:0/Cer(d18:1/16:0), CE 18:0/Cer(d18:1/24:1), CE 18:0/PC 16:0/16:0, CE 18:0/PC 18:1/18:1, CE 18:0/PC 16:0/18:1, CE 20:4/PC O-16:0/18:1-alkyl, CE 18:3/PE 18:0/18:2, CE 20:4/Gb3(d18:1/16:0), CE 14:0/PE 18:0/18:2, CE 18:0/Cer(d18:1/26:1), CE 18:3/Gb3(d18:1/22:0), CE 14:0/Gb3(d18:1/16:0), CE 18:3/PC O-16:0/18:1-alkyl, CE 18:3/Gb3(d18:1/16:0), CE 14:0/PC O-16:0/18:1-alkyl, CE 20:4/Gb3(d18:1/18:0), CE 18:3/Gb3(d18:1/24:1), CE 14:0/Gb3(d18:1/24:1), CE 20:5/PC O-16:0/18:1-alkyl, CE 18:0/Gb3(d18:1/18:0), CE 18:0/Gb3(d18:1/16:0) and CE 18:0/Gb3(d18:1/24:1) (Table 5b).

In one particular embodiment, the one or more lipid-lipid concentration ratio(s) whose decrease(s) is (are) compared to the control is (are) selected from: CE 18:0/PC 18:0/18:2, PC 18:0/18:2/PE 18:0/18:2, Cer(d18:1/24:0)/PE 18:0/18:2, CE 18:0/CE 18:1, CE 18:2/Gb3(d18:1/16:0), CE 16:0/Gb3 (d18:1/16:0), CE 18:0/PC 16:0/22:6, CE 14:0/Gb3(d18:1/24:0), CE 18:0/SM (d18:1/16:0) (d18:1/15:1-OH), CE 18:3/SM (d18:1/14:0) (d18:1/13:1-OH), CE 18:0/PC 16:0/18:2, Cer(d18:1/24:0)/PC O-16:0/18:1-alkyl, CE 18:0/Gb3(d18:1/24:0), CE 18:3/PC 16:0/18:1, PC 18:0/20:3/PC O-16:0/18:1-alkyl, CE 14:0/PC 16:0/16:0, CE 17:1/Gb3(d18:1/16:0), CE 14:0/SM (d18:1/14:0) (d18:1/13:1-OH), PC 18:0/20:3/PE 18:0/18:2, CE 18:0/SM (d18:1/14:0) (d18:1/13:1-OH), CE 14:0/PC 16:0/18:1, CE 18:0/SM (d18:1/24:1) (d18:1/23:2-OH), CE 18:0/Cer(d18:1/24:1), CE 18:0/PC 16:0/16:0, CE 18:0/PC 18:1/18:1, CE 18:0/PC 16:0/18:1, CE 20:4/PC O-16:0/18:1-alkyl, CE 18:3/PE 18:0/18:2, CE 20:4/Gb3 (d18:1/16:0), CE 14:0/PE 18:0/18:2, CE 18:0/Cer(d18:1/26:1), CE 18:3/Gb3(d18:1/22:0), CE 14:0/Gb3(d18:1/16:0), CE 18:3/PC O-16:0/18:1-alkyl, CE 18:3/Gb3(d18:1/16:0), CE 14:0/PC O-16:0/18:1-alkyl, CE 20:4/Gb3(d18:1/18:0), CE 18:3/Gb3(d18:1/24:1), CE 14:0/Gb3(d18:1/24:1), CE 20:5/PC O-16:0/18:1-alkyl, CE 18:0/Gb3(d18:1/18:0), CE 18:0/Gb3(d18:1/16:0) and CE 18:0/Gb3(d18:1/24:1) (Table 5b).

In a preferred embodiment, the one or more lipid-lipid concentration ratio(s) whose increase(s) is (are) compared to the control is (are) selected from: Gb3(d18:1/24:1)/SM (d18:1/17:0) (d18:1/16:1-OH), Gb3(d18:1/16:0)/SM (d18:1/17:0) (d18:1/16:1-OH) and Gb3(d18:1/24:1)/GlcCer(d18:1/24:0) (Table 7); and the one or more lipid-lipid concentration ratio(s) whose decrease(s) is (are) compared to the control is (are) selected from: CE 18:3/PC 16:0/18:1, CE 18:0/SM (d18:1/14:0) (d18:1/13:1-OH), CE 14:0/PE 18:0/18:2, CE 18:3/PC O-16:0/18:1-alkyl, CE 18:0/Gb3(d18:1/16:0) and CE 18:0/Gb3(d18:1/24:1) (Table 7).

In yet another alternative embodiment, the present invention relates to a method for determining whether a subject not undergoing statin treatment who is suffering from type 2 diabetes mellitus is at risk to develop one or more CVD complications, such as AMI and/or CVD death, comprising determining in a sample from said subject one or more lipid-clinical concentration ratio(s), wherein (an) increased or decreased lipid-clinical concentration ratio(s) in said sample, when compared to a control sample, is (are) indicative of said subject having an increased risk of developing one or more CVD complications, such as AMI or CVD death, wherein the one or more lipid-clinical concentration ratio(s) whose increase(s) is (are) compared to the control is (are) selected from: PC 18:1/18:1/lipoprotein(a), PC O-16:0/18:1-alkyl/lipoprotein(a), Gb3(d18:1/18:0)/lipoprotein(a), SM (d18:1/23:1) (d18:1/22:2-OH)/lipoprotein(a), Gb3(d18:1/24:1)/lipoprotein(a), Gb3(d18:1/16:0)/lipoprotein(a), PE 18:0/18:2/lipoprotein(a), LacCer(d18:1/24:1)/lipoprotein(a), LacCer(d18:1/22:0)/lipoprotein(a), Gb3(d18:1/22:0)/lipoprotein(a), CE 17:1/lipoprotein(a), Gb3(d18:1/24:0)/lipoprotein(a), PC 16:0/18:2/lipoprotein(a), PC O-18:0/18:2-alkyl/lipoprotein(a), LacCer(d18:1/24:0)/lipoprotein(a), PC 17:0/18:2/lipoprotein(a), SM (d18:1/18:0)/lipoprotein(a), CE 15:0/lipoprotein(a), PC O-16:0/18:2-alkyl/lipoprotein(a), Gb3(d18:1/24:1)/LDL cholesterol, Gb3(d18:1/24:1)/apolipoprotein B, Gb3(d18:1/24:1)/total cholesterol, Gb3(d18:1/24:1)/apolipoprotein A-I, PC O-16:0/18:1-alkyl/LDL cholesterol, Gb3(d18:1/16:0)/LDL cholesterol, Gb3(d18:1/24:1)/HDL cholesterol, Gb3(d18:1/22:0)/LDL cholesterol, Gb3(d18:1/18:0)/LDL cholesterol, Gb3(d18:1/24:0)/LDL cholesterol, Gb3(d18:1/16:0)/apolipoprotein B, PC O-16:0/18:1-alkyl/apolipoprotein B, PC O-16:0/18:1-alkyl/triglycerides, Gb3(d18:1/16:0)/total cholesterol, Gb3(d18:1/22:0)/apolipoprotein B, PC 16:0/16:0/LDL cholesterol, Gb3(d18:1/18:0)/apolipoprotein B, PC O-16:0/18:1-alkyl/total cholesterol, SM (d18:1/24:1) (d18 1/23:2-OH)/LDL cholesterol, Gb3(d18:1/16:0)/triglycerides, PE 18:0/18:2/LDL cholesterol, Gb3(d18:1/22:0)/total cholesterol, PE 18:0/18:2/triglycerides, Gb3(d18:1/18:0)/total cholesterol, PE 18:0/18:2/total cholesterol, PC 16:0/18:2/LDL cholesterol, PC 16:0/16:0/total cholesterol, PE 18:0/18:2/apolipoprotein B and SM (d18:1/14:0) (d18:1/13:1-OH)/total cholesterol (Table 5c);
and wherein the one or more lipid-clinical concentration ratio(s) whose decrease(s) is (are) compared to the control is (are) selected from: CE 14:0/HDL cholesterol and CE 14:0/supersensitive C-reactive protein (Table 5c).

In a preferred embodiment, the one or more lipid-clinical concentration ratio(s) whose increase(s) is (are) compared to the control is (are) selected from: PC 18:1/18:1/lipoprotein(a), Gb3(d18:1/18:0)/lipoprotein(a), Gb3(d18:1/16:0)/lipoprotein(a) and LacCer(d18:1/24:1)/lipoprotein(a) (Table 7); and the one or more lipid-clinical concentration ratio(s) whose decrease(s) is (are) compared to the control is: CE 14:0/supersensitive C-reactive protein (Table 7).

In another aspect, the present invention relates to a method for evaluating the effectiveness of a treatment of CVD and/or one or more of its complications, such as AMI or CVD death, in a subject not undergoing statin treatment, said method comprising determining in a sample from said subject one or more lipid-lipid concentration ratio(s), wherein (an) increased or decreased lipid-lipid concentration ratio(s) in said sample, when compared to a control sample, is (are) indicative of effectiveness of said treatment, wherein the one or more lipid-lipid concentration ratio(s) whose increase(s) is (are) compared to the control is (are) selected from: Gb3(d18:1/16:0)/PC 18:0/22:6, Cer(d18:1/18:0)/Cer(d18:1/24:0), Cer(d18:1/20:0)/Cer(d18:1/24:0), SM (d18:1/16:0) (d18:1/15:1-OH)/SM (d18:1/24:0) (d18:1/23:1-OH) and Cer(d18:1/22:0)/Cer(d18:1/24:0) (Table 3);
and wherein the one or more lipid-lipid concentration ratio(s) whose decrease(s) is (are) compared to the control is (are) selected from: Cer(d18:1/24:0)/PC 16:0/18:2, SM (d18:1/24:0) (d18:1/23:1-OH)/SM (d18:1/24:1) (d18:1/23:

2-OH), Cer(d18:1/24:0)/Cer(d18:1/24:1), Cer(d18:1/24:0)/ SM (d18:1/14:0) (d18:1/13:1-OH), Cer(d18:1/24:0)/Gb3 (d18:1/16:0) and Cer(d18:1/24:0)/SM (d18:1/16:1) (d18:1/ 15:2-OH) (Table 3).

In one particular embodiment, the one or more lipid-lipid concentration ratio(s) whose decrease(s) is (are) compared to the control is (are) selected from: Cer(d18:1/24:0)/PC 16:0/18:2, SM (d18:1/24:0) (d18:1/23:1-OH)/SM (d18:1/24: 1) (d18:1/23:2-OH), Cer(d18:1/24:0)/SM (d18:1/14:0) (d18: 1/13:1-OH), Cer(d18:1/24:0)/Gb3(d18:1/16:0) and Cer(d18: 1/24:0)/SM (d18:1/16:1) (d18:1/15:2-OH) (Table 3).

In yet another alternative embodiment the present invention relates to method for evaluating the effectiveness of a treatment of CVD and/or one or more of its complications, such as AMI or CVD death, in a subject not undergoing statin treatment, said method comprising determining in a sample from said subject one or more lipid-clinical concentration ratio(s), wherein (an) increased or decreased lipid-clinical concentration ratio(s) in said sample, when compared to a control sample, is (are) indicative of effectiveness of said treatment, wherein the one or more lipid-clinical concentration ratio(s) whose increase(s) is (are) compared to the control is (are) selected from: GlcCer(d18:1/16:0)/total cholesterol, Gb3(d18:1/16:0)/apolipoprotein A-I, Gb3(d18: 1/18:0)/apolipoprotein A-I, Gb3(d18:1/16:0)/HDL cholesterol and PC 16:0/18:2/total cholesterol (Table 3);
and wherein the one or more lipid-clinical concentration ratio(s) whose decrease(s) is (are) compared to the control is (are) selected from: Cer(d18:1/24:0)/supersensitive C-reactive protein and PC 18:0/22:6/supersensitive C-reactive protein (Table 3).

For the purposes of the invention, and particularly for lipid-clinical concentration ratios, an Apolipoprotein A-I measurement may alternatively be an Apolipoprotein A-II measurement.

In another aspect the present invention relates to a method for evaluating the effectiveness of a treatment of CVD and/or one or more of its complications, such as AMI or CVD death, in a subject not undergoing statin treatment and not suffering from type 2 diabetes mellitus said method comprising determining in a sample from said subject the concentration(s) of one or more lipid(s), wherein (an) increased or decreased concentration(s) in said sample, when compared to a control sample, is (are) indicative of effectiveness of said treatment, wherein the one or more lipid(s) whose increase(s) in concentration is (are) compared to the control is (are) selected from: CE 19:1 oxCE 682.6, GlcCer(d18:1/16:0), SM (d18:1/18:1), CE 20:4, LacCer (d18:1/16:0), Cer 18:1/16:0, SM 18:1/16:0 and CE 16:0 (Tables 4a, 6 and 8);
and wherein the one or more lipid(s) whose decrease(s) in concentration is (are) compared to the control is (are) selected from: PC 18:0/22:6, SM (d18:1/23:1) (d18:1/22:2-OH), PC 16:0/22:6, SM 18:1/24:0 and LPC 16:0 (Tables 4a, 6 and 8).

In one particular embodiment, the one or more lipid(s) whose increase(s) in concentration is (are) compared to the control is (are) selected from: CE 19:1 (oxCE 682.6), CE 20:4, Cer 18:1/16:0 and SM 18:1/16:0 (Tables 4a, 6 and 8);
and wherein the one or more lipid(s) whose decrease(s) in concentration is (are) compared to the control is (are) selected from: PC 18:0/22:6 and SM 18:1/24:0 and LPC 16:0 (Tables 4a, 6 and 8).

In a preferred embodiment, the one or more lipid(s) whose increase(s) in concentration is (are) compared to the control is (are) selected from: GlcCer(d18:1/16:0), CE 20:4, LacCer (d18:1/16:0), Cer 18:1/16:0, SM 18:1/16:0 and CE 16:0 (Table 8);
and the one or more lipid(s) whose decrease(s) in concentration is (are) compared to the control is (are) selected from: PC 16:0/22:6, SM 18:1/24:0 and LPC 16:0 (Table 8).

In one particularly preferred embodiment, the one or more lipid(s) whose increase(s) in concentration is (are) compared to the control is (are) selected from: CE 20:4, Cer 18:1/16:0 and SM 18:1/16:0 (Table 8);
and the one or more lipid(s) whose decrease(s) in concentration is (are) compared to the control is (are) selected from: SM 18:1/24:0 and LPC 16:0 (Table 8).

In an alternative embodiment, the present invention relates to a method for evaluating the effectiveness of a treatment of CVD and/or one or more of its complications, such as AMI or CVD death, in a subject not undergoing statin treatment and not suffering from type 2 diabetes mellitus said method comprising determining in a sample from said subject one or more lipid-lipid concentration ratio(s), wherein (an) increased or decreased lipid-lipid concentration ratio(s) in said sample, when compared to a control sample, is (are) indicative of effectiveness of said treatment, wherein the one or more lipid-lipid concentration ratio(s) whose increase(s) is (are) compared to the control is (are) selected from: Cer(d18:1/18:0)/SM (d18:1/23:1) (d18: 1/22:2-OH), Cer(d18:1/16:0)/PC 18:0/22:6, Cer(d18:1/18: 0)/PC 16:0/22:6, GlcCer(d18:1/16:0)/PC 18:0/22:6, GlcCer (d18:1/18:0)/SM (d18:1/23:1) (d18:1/22:2-OH), Cer(d18:1/ 16:0)/PC 16:0/22:6, Cer(d18:1/20:0)/SM (d18:1/23:1) (d18: 1/22:2-OH), GlcCer(d18:1/18:0)/PC 16:0/22:6, SM (d18:1/ 18:1)/SM (d18:1/23:1) (d18:1/22:2-OH), Cer(d18:1/20:0)/ PC 16:0/22:6, SM (d18:1/16:0) (d18:1/15:1-OH)/SM (d18: 1/23:1) (d18:1/22:2-OH), SM (d18:1/15:0) (d18:1/14:1-OH)/SM (d18:1/23:1) (d18:1/22:2-OH), GlcCer(d18:1/20: 0)/SM (d18:1/23:1) (d18:1/22:2-OH), Cer(d18:1/24:1)/PC 18:0/22:6, SM (d18:1/16:1) (d18:1/15:2-OH)/SM (d18:1/23: 1) (d18:1/22:2-OH), GlcCer(d18:1/16:0)/PC 16:0/22:6, LacCer(d18:1/22:0)/PC 16:0/22:6, LacCer(d18:1/22:0)/SM (d18:1/23:1) (d18:1/22:2-OH), GlcCer(d18:1/20:0)/PC 16:0/22:6, CE 16:0/PC 18:0/22:6, Cer(d18:1/22:0)/PC 18:0/ 22:6, CE 18:2/PC 18:0/22:6, CE 18:1/PC 18:0/22:6, Cer (d18:1/16:0)/Cer(d18:1/24:0), Gb3(d18:1/16:0)/PC 16:0/22: 6, CE 20:4/PC 18:0/22:6, CE 22:6/PC 18:0/22:6, PC 16:0/ 16:0/PC 16:0/22:6, CE 16:0/PC 16:0/22:6, CE 18:2/PC 16:0/22:6, Gb3(d18:1/24:0)/PC 16:0/22:6, CE 18:1/PC 16:0/ 22:6, CE 20:4/PC 16:0/22:6, SM (d18:1/16:1) (d18:1/15:2-OH)/SM (d18:1/24:0) (d18:1/23:1-OH), Cer(d18:1/16:0)/ Cer(d18:1/22:0), CE 16:0/Cer(d18:1/24:0), SM (d18:1/18: 1)/SM (d18:1/24:0) (d18:1/23:1-OH), GlcCer(d18:1/18:0)/ SM (d18:1/24:0) (d18:1/23:1-OH) and SM (d18:1/15:0) (d18:1/14:1-OH)/SM (d18:1/24:0) (d18:1/23:1-OH) (Table 4b);
and wherein the one or more lipid-lipid concentration ratio (s) whose decrease(s) is (are) compared to the control is (are) selected from: Cer(d18:1/24:0)/GlcCer(d18:1/18:0), Cer (d18:1/24:0)/GlcCer(d18:1/16:0), PC 16:0/22:6/SM (d18:1/ 16:0) (d18:1/15:1-OH), PC 18:0/22:6/SM (d18:1/14:0) (d18:1/13:1-OH), PC 16:0/22:6/SM (d18:1/16:1) (d18:1/15: 2-OH), PC 18:0/22:6/SM (d18:1/16:0) (d18:1/15:1-OH), PC 18:0/22:6/SM (d18:1/15:0) (d18:1/14:1-OH), PC 18:0/22:6/ SM (d18:1/18:0), PC 18:0/22:6/SM (d18:1/16:1) (d18:1/15: 2-OH) and PC 18:0/22:6/SM (d18:1/18:1) (Table 4b).

In a preferred embodiment, the one or more lipid-lipid concentration ratio(s) whose increase(s) is (are) compared to the control is (are) selected from: Cer(d18:1/18:0)/SM (d18: 1/23:1) (d18:1/22:2-OH), Cer(d18:1/16:0)/PC 18:0/22:6, Cer(d18:1/18:0)/PC 16:0/22:6, GlcCer(d18:1/16:0)/PC 18:0/22:6, GlcCer(d18:1/18:0)/SM (d18:1/23:1) (d18:1/22:2-OH), Cer(d18:1/16:0)/PC 16:0/22:6, Cer(d18:1/20:0)/SM (d18:1/23:1) (d18:1/22:2-OH), GlcCer(d18:1/18:0)/PC 16:0/22:6, SM (d18:1/18:1)/SM (d18:1/23:1) (d18:1/22:2-OH), Cer(d18:1/20:0)/PC 16:0/22:6, SM (d18:1/16:0) (d18:1/15:1-OH)/SM (d18:1/23:1) (d18:1/22:2-OH), SM (d18:1/15:0) (d18:1/14:1-OH)/SM (d18:1/23:1) (d18:1/22:2-OH), GlcCer(d18:1/20:0)/SM (d18:1/23:1) (d18:1/22:2-OH), Cer (d18:1/24:1)/PC 18:0/22:6, SM (d18:1/16:1) (d18:1/15:2-OH)/SM (d18:1/23:1) (d18:1/22:2-OH), GlcCer(d18:1/16:0)/PC 16:0/22:6, LacCer(d18:1/22:0)/PC 16:0/22:6, CE 16:0/PC 18:0/22:6, CE 18:2/PC 18:0/22:6 and Cer(d18:1/16:0)/Cer(d18:1/24:0) (Table 6);
and the one or more lipid-lipid concentration ratio(s) whose decrease(s) is (are) compared to the control is (are) selected from: PC 18:0/22:6/SM (d18:1/16:1) (d18:1/15:2-OH) and PC 18:0/22:6/SM (d18:1/18:1) (Table 6).

In yet another alternative embodiment, a method is provided for evaluating the effectiveness of a treatment of CVD and/or one or more of its complications, such as AMI or CVD death, in a subject not undergoing statin treatment and not suffering from type 2 diabetes mellitus, said method comprising determining in a sample from said subject one or more lipid-clinical concentration ratio(s), wherein (an) increased or decreased lipid-clinical concentration ratio(s) in said sample, when compared to a control sample, is (are) indicative of effectiveness of said treatment, wherein the one or more lipid-clinical concentration ratio(s) whose increase(s) is (are) compared to the control is (are) selected from: Cer(d18:1/16:0)/HDL cholesterol, GlcCer(d18:1/16:0)/apolipoprotein A-I, CE 19:1 oxCE 682.6/apolipoprotein A-I, GlcCer(d18:1/18:0)/apolipoprotein A-I, GlcCer(d18:1/18:0)/HDL cholesterol, GlcCer(d18:1/16:0)/HDL cholesterol, GlcCer(d18:1/20:0)/apolipoprotein A-I, GlcCer(d18:1/18:0)/total cholesterol and Cer(d18:1/16:0)/apolipoprotein B
(Table 4c);
and wherein the one or more lipid-clinical concentration ratio(s) whose decrease(s) is (are) compared to the control is (are) selected from: LacCer(d18:1/24:0)/supersensitive C-reactive protein, CE 17:1/supersensitive C-reactive protein, SM (d18:1/16:0) (d18:1/15:1-OH)/supersensitive C-reactive protein, GlcCer(d18:1/24:0)/supersensitive C-reactive protein, Gb3(d18:1/22:0)/supersensitive C-reactive protein, PC 18:0/20:3/apolipoprotein B, PC 16:0/16:1/supersensitive C-reactive protein, PC 16:0/22:6/total cholesterol, PC 16:0/22:6/apolipoprotein B, PC 18:1/18:1/supersensitive C-reactive protein, SM (d18:1/24:1) (d18:1/23:2-OH)/supersensitive C-reactive protein, PC 18:0/18:2/supersensitive C-reactive protein, Cer(d18:1/24:1)/supersensitive C-reactive protein, Cer(d18:1/22:0)/supersensitive C-reactive protein, PC 18:0/22:6/triglycerides, SM (d18:1/18:0)/supersensitive C-reactive protein, PC 18:0/20:3/supersensitive C-reactive protein, SM (d18:1/24:0) (d18:1/23:1-OH)/supersensitive C-reactive protein, PC 16:0/18:1/supersensitive C-reactive protein, SM (d18:1/23:1) (d18:1/22:2-OH)/total cholesterol, PC 18:0/22:6/LDL cholesterol, PC 18:0/22:6/total cholesterol, SM (d18:1/23:1) (d18:1/22:2-OH)/LDL cholesterol, SM (d18:1/23:1) (d18:1/22:2-OH)/apolipoprotein B, PC 18:0/22:6/apolipoprotein B, SM (d18:1/23:0) (d18:1/22:1-OH)/supersensitive C-reactive protein, PC 18:0/18:1/supersensitive C-reactive protein, LPC 16:0/supersensitive C-reactive protein, PC 16:0/22:6/supersensitive C-reactive protein, SM (d18:1/23:1) (d18:1/22:2-OH)/supersensitive C-reactive protein, PC 18:0/22:6/lipoprotein(a) and PC 16:0/18:0/supersensitive C-reactive protein (Table 4c).

In one particular embodiment, the one or more lipid-clinical concentration ratio(s) whose increase(s) is (are) compared to the control is (are) selected from: CE 19:1 oxCE 682.6/apolipoprotein A-I, GlcCer(d18:1/18:0)/HDL cholesterol, GlcCer(d18:1/16:0)/HDL cholesterol, GlcCer (d18:1/20:0)/apolipoprotein A-I and GlcCer(d18:1/18:0)/total cholesterol (Table 4c).

In a preferred embodiment, the one or more lipid-clinical concentration ratio(s) whose increase(s) is (are) compared to the control is: Cer(d18:1/16:0)/HDL cholesterol (Table 6); and/or the one or more lipid-clinical concentration ratio(s) whose decrease(s) is (are) compared to the control is (are) selected from: PC 18:0/22:6/LDL cholesterol, PC 18:0/22:6/total cholesterol and PC 18:0/22:6/apolipoprotein B (Table 6).

In another aspect, the present invention relates to a method for evaluating the effectiveness of a treatment of CVD and/or one or more of its complications, such as AMI or CVD death, in a subject not undergoing statin treatment and suffering from type 2 diabetes mellitus said method comprising determining in a sample from said subject the concentration(s) of one or more lipid(s), wherein (an) increased or decreased concentration(s) in said sample, when compared to a control sample, is (are) indicative of effectiveness of said treatment, wherein the one or more lipid(s) whose increase(s) in concentration is (are) compared to the control is (are) selected from: Gb3(d18:1/24:1), Gb3 (d18:1/16:0), GlcCer 18:1/16:0, LacCer 18:1/16:0 and PC 16:0/22:6 (Tables 5a, 7 and 8);
and wherein the one or more lipid(s) whose decrease(s) in concentration is (are) compared to the control is (are) selected from: PC O-16:0/20:4-alkyl, CE 20:4, CE 18:0, CE 14:0, CE 22:6, CE 18:3, GlcCer 18:1/18:0 and SM 18:1/24:0 (Tables 5a, 7 and 8).

In one particular embodiment, the one or more lipid(s) whose increase(s) in concentration is (are) compared to the control is (are) selected from: Gb3(d18:1/24:1), Gb3(d18:1/16:0), GlcCer 18:1/16:0 and LacCer 18:1/16:0 (Tables 5a, 7 and 8);
and wherein the one or more lipid(s) whose decrease(s) in concentration is (are) compared to the control is (are) selected from: PC O-16:0/20:4-alkyl, CE 20:4, CE 22:6, GlcCer 18:1/18:0 and SM 18:1/24:0 (Tables 5a, 7 and 8).

In a preferred embodiment, the one or more lipid(s) whose increase(s) in concentration is (are) compared to the control is (are) selected from: Gb3 18:1/16:0, GlcCer 18:1/16:0, LacCer 18:1/16:0 and PC 16:0/22:6 (Table 8);
and the one or more lipid(s) whose decrease(s) in concentration is (are) compared to the control is (are) selected from: CE 14:0, CE 22:6, CE 18:3, GlcCer 18:1/18:0 and SM 18:1/24:0 (Table 8).

In one particularly preferred embodiment, the one or more lipid(s) whose increase(s) in concentration is (are) compared to the control is (are) selected from: Gb3 18:1/16:0, GlcCer 18:1/16:0 and LacCer 18:1/16:0 (Table 8);
and the one or more lipid(s) whose decrease(s) in concentration is (are) compared to the control is (are) selected from: CE 22:6, GlcCer 18:1/18:0 and SM 18:1/24:0 (Table 8).

In an alternative embodiment, the present invention relates to a method for evaluating the effectiveness of a treatment of CVD and/or one or more of its complications, such as AMI or CVD death, in a subject not undergoing statin treatment and suffering from type 2 diabetes mellitus said method comprising determining in a sample from said subject one or more lipid-lipid concentration ratio(s), wherein (an) increased or decreased lipid-lipid concentration ratio(s) in said sample, when compared to a control sample, is (are) indicative of effectiveness of said treatment, wherein the one or more lipid-lipid concentration ratio(s) whose increase(s) is (are) compared to the control is (are) selected from: Gb3(d18:1/24:1)/SM (d18:1/17:0) (d18:1/16:1-OH), Gb3(d18:1/24:1)/PC O-16:0/20:4-alkyl, Gb3(d18:1/16:0)/SM (d18:1/17:0) (d18:1/16:1-OH), Gb3(d18:1/24:1)/GlcCer(d18:1/24:0), Gb3(d18:1/24:1)/GlcCer(d18:1/22:0) and Gb3(d18:1/22:0)/SM (d18:1/17:0) (d18:1/16:1-OH) (Table 5b);

and wherein the one or more lipid-lipid concentration ratio(s) whose decrease(s) is (are) compared to the control is (are) selected from: CE 18:0/PC 18:0/18:2, PC 18:0/18:2/PE 18:0/18:2, Cer(d18:1/24:0)/PE 18:0/18:2, CE 18:0/CE 18:1, CE 18:2/Gb3(d18:1/16:0), CE 16:0/Gb3(d18:1/16:0), CE 18:0/PC 16:0/22:6, CE 14:0/Gb3(d18:1/24:0), CE 18:0/SM (d18:1/16:0) (d18:1/15:1-OH), CE 18:3/SM (d18:1/14:0) (d18:1/13:1-OH), CE 18:0/PC 16:0/18:2, Cer(d18:1/24:0)/PC O-16:0/18:1-alkyl, CE 18:0/Gb3(d18:1/24:0), CE 18:3/PC 16:0/18:1, PC 18:0/20:3/PC O-16:0/18:1-alkyl, CE 14:0/PC 16:0/16:0, CE 17:1/Gb3(d18:1/16:0), CE 14:0/SM (d18:1/14:0) (d18:1/13:1-OH), PC 18:0/20:3/PE 18:0/18:2, CE 18:0/SM (d18:1/14:0) (d18:1/13:1-OH), CE 14:0/PC 16:0/18:1, CE 18:0/SM (d18:1/24:1) (d18:1/23:2-OH), CE 18:0/Cer(d18:1/16:0), CE 18:0/Cer(d18:1/24:1), CE 18:0/PC 16:0/16:0, CE 18:0/PC 18:1/18:1, CE 18:0/PC 16:0/18:1, CE 20:4/PC O-16:0/18:1-alkyl, CE 18:3/PE 18:0/18:2, CE 20:4/Gb3(d18:1/16:0), CE 14:0/PE 18:0/18:2, CE 18:0/Cer(d18:1/26:1), CE 18:3/Gb3(d18:1/22:0), CE 14:0/Gb3(d18:1/16:0), CE 18:3/PC O-16:0/18:1-alkyl, CE 18:3/Gb3(d18:1/16:0), CE 14:0/PC O-16:0/18:1-alkyl, CE 20:4/Gb3(d18:1/18:0), CE 18:3/Gb3(d18:1/24:1), CE 14:0/Gb3(d18:1/24:1), CE 20:5/PC O-16:0/18:1-alkyl, CE 18:0/Gb3(d18:1/18:0), CE 18:0/Gb3(d18:1/16:0) and CE 18:0/Gb3(d18:1/24:1) (Table 5b).

In one particular embodiment, the one or more lipid-lipid concentration ratio(s) whose decrease(s) is (are) compared to the control is (are) selected from: CE 18:0/PC 18:0/18:2, PC 18:0/18:2/PE 18:0/18:2, Cer(d18:1/24:0)/PE 18:0/18:2, CE 18:0/CE 18:1, CE 18:2/Gb3(d18:1/16:0), CE 16:0/Gb3 (d18:1/16:0), CE 18:0/PC 16:0/22:6, CE 14:0/Gb3(d18:1/24:0), CE 18:0/SM (d18:1/16:0) (d18:1/15:1-OH), CE 18:3/SM (d18:1/14:0) (d18:1/13:1-OH), CE 18:0/PC 16:0/18:2, Cer(d18:1/24:0)/PC O-16:0/18:1-alkyl, CE 18:0/Gb3(d18:1/24:0), CE 18:3/PC 16:0/18:1, PC 18:0/20:3/PC O-16:0/18:1-alkyl, CE 14:0/PC 16:0/16:0, CE 17:1/Gb3(d18:1/16:0), CE 14:0/SM (d18:1/14:0) (d18:1/13:1-OH), PC 18:0/20:3/PE 18:0/18:2, CE 18:0/SM (d18:1/14:0) (d18:1/13:1-OH), CE 14:0/PC 16:0/18:1, CE 18:0/SM (d18:1/24:1) (d18:1/23:2-OH), CE 18:0/Cer(d18:1/24:1), CE 18:0/PC 16:0/16:0, CE 18:0/PC 18:1/18:1, CE 18:0/PC 16:0/18:1, CE 20:4/PC O-16:0/18:1-alkyl, CE 18:3/PE 18:0/18:2, CE 20:4/Gb3 (d18:1/16:0), CE 14:0/PE 18:0/18:2, CE 18:0/Cer(d18:1/26:1), CE 18:3/Gb3(d18:1/22:0), CE 14:0/Gb3(d18:1/16:0), CE 18:3/PC O-16:0/18:1-alkyl, CE 18:3/Gb3(d18:1/16:0), CE 14:0/PC O-16:0/18:1-alkyl, CE 20:4/Gb3(d18:1/18:0), CE 18:3/Gb3(d18:1/24:1), CE 14:0/Gb3(d18:1/24:1), CE 20:5/PC O-16:0/18:1-alkyl, CE 18:0/Gb3(d18:1/18:0), CE 18:0/Gb3(d18:1/16:0) and CE 18:0/Gb3(d18:1/24:1) (Table 5b).

In a preferred embodiment, the one or more lipid-lipid concentration ratio(s) whose increase(s) is (are) compared to the control is (are) selected from: Gb3(d18:1/24:1)/SM (d18:1/17:0) (d18:1/16:1-OH), Gb3(d18:1/16:0)/SM (d18:1/17:0) (d18:1/16:1-OH) and Gb3(d18:1/24:1)/GlcCer(d18:1/24:0) (Table 7); and the one or more lipid-lipid concentration ratio(s) whose decrease(s) is (are) compared to the control is (are) selected from: CE 18:3/PC 16:0/18:1, CE 18:0/SM (d18:1/14:0) (d18:1/13:1-OH), CE 14:0/PE 18:0/18:2, CE 18:3/PC O-16:0/18:1-alkyl, CE 18:0/Gb3(d18:1/16:0) and CE 18:0/Gb3(d18:1/24:1) (Table 7).

In yet another alternative embodiment, a method is provided for evaluating the effectiveness of a treatment of CVD and/or one or more of its complications, such as AMI or CVD death, in a subject not undergoing statin treatment and suffering from type 2 diabetes mellitus, said method comprising determining in a sample from said subject one or more lipid-clinical concentration ratio(s), wherein (an) increased or decreased lipid-clinical concentration ratio(s) in said sample, when compared to a control sample, is (are) indicative of effectiveness of said treatment, wherein the one or more lipid-clinical concentration ratio(s) whose increase(s) is (are) compared to the control is (are) selected from: PC 18:1/18:1/lipoprotein(a), PC O-16:0/18:1-alkyl/lipoprotein(a), Gb3(d18:1/18:0)/lipoprotein(a), SM (d18:1/23:1) (d18:1/22:2-OH)/lipoprotein(a), Gb3(d18:1/24:1)/lipoprotein(a), Gb3(d18:1/16:0)/lipoprotein(a), PE 18:0/18:2/lipoprotein(a), LacCer(d18:1/24:1)/lipoprotein(a), LacCer(d18:1/22:0)/lipoprotein(a), Gb3(d18:1/22:0)/lipoprotein(a), CE 17:1/lipoprotein(a), Gb3(d18:1/24:0)/lipoprotein(a), PC 16:0/18:2/lipoprotein(a), PC O-18:0/18:2-alkyl/lipoprotein(a), LacCer(d18:1/24:0)/lipoprotein(a), PC 17:0/18:2/lipoprotein(a), SM (d18:1/18:0)/lipoprotein(a), CE 15:0/lipoprotein(a), PC O-16:0/18:2-alkyl/lipoprotein(a), Gb3(d18:1/24:1)/LDL cholesterol, Gb3(d18:1/24:1)/apolipoprotein B, Gb3(d18:1/24:1)/total cholesterol, Gb3(d18:1/24:1)/apolipoprotein A-I, PC O-16:0/18:1-alkyl/LDL cholesterol, Gb3 (d18:1/16:0)/LDL cholesterol, Gb3(d18:1/24:1)/HDL cholesterol, Gb3(d18:1/22:0)/LDL cholesterol, Gb3(d18:1/18:0)/LDL cholesterol, Gb3(d18:1/24:0)/LDL cholesterol, Gb3 (d18:1/16:0)/apolipoprotein B, PC O-16:0/18:1-alkyl/apolipoprotein B, PC O-16:0/18:1-alkyl/triglycerides, Gb3 (d18:1/16:0)/total cholesterol, Gb3(d18:1/22:0)/apolipoprotein B, PC 16:0/16:0/LDL cholesterol, Gb3(d18:1/18:0)/apolipoprotein B, PC O-16:0/18:1-alkyl/total cholesterol, SM (d18:1/24:1) (d18:1/23:2-OH)/LDL cholesterol, Gb3(d18:1/16:0)/triglycerides, PE 18:0/18:2/LDL cholesterol, Gb3(d18:1/22:0)/total cholesterol, PE 18:0/18:2/triglycerides, Gb3(d18:1/18:0)/total cholesterol, PE 18:0/18:2/total cholesterol, PC 16:0/18:2/LDL cholesterol, PC 16:0/16:0/total cholesterol, PE 18:0/18:2/apolipoprotein B and SM (d18:1/14:0) (d18:1/13:1-OH)/total cholesterol (Table 5c); and wherein the one or more lipid-clinical concentration ratio(s) whose decrease(s) is (are) compared to the control is (are) selected from: CE 14:0/HDL cholesterol and CE 14:0/supersensitive C-reactive protein (Table 5c).

In a preferred embodiment, the one or more lipid-clinical concentration ratio(s) whose increase(s) is (are) compared to the control is (are) selected from: PC 18:1/18:1/lipoprotein (a), Gb3(d18:1/18:0)/lipoprotein(a), Gb3(d18:1/16:0)/lipoprotein(a) and LacCer(d18:1/24:1)/lipoprotein(a) (Table 7); and the one or more lipid-clinical concentration ratio(s) whose decrease(s) is (are) compared to the control is: CE 14:0/supersensitive C-reactive protein (Table 7).

In yet another aspect the present invention relates to a method of choosing an appropriate treatment of CVD and/or one or more of its complications, such as AMI or CVD death, in a subject not undergoing statin treatment, said method comprising determining in a sample from said subject one or more lipid-lipid concentration ratio(s), wherein (an) increased or decreased lipid-lipid concentration ratio(s) in said sample, when compared to a control sample, is (are) indicative of said subject being in need of treatment or a change in, or supplementation of, an already administered treatment, wherein the one or more lipid-lipid concentration ratio(s) whose increase(s) is (are) compared to the control is (are) selected from: Gb3(d18:1/16:0)/PC 18:0/ 22:6, Cer(d18:1/18:0)/Cer(d18:1/24:0), Cer(d18:1/20:0)/ Cer(d18:1/24:0), SM (d18:1/16:0) (d18:1/15:1-OH)/SM (d18:1/24:0) (d18:1/23:1-OH) and Cer(d18:1/22:0)/Cer (d18:1/24:0) (Table 3);
and wherein the one or more lipid-lipid concentration ratio(s) whose decrease(s) is (are) compared to the control is (are) selected from: Cer(d18:1/24:0)/PC 16:0/18:2, SM (d18:1/24:0) (d18:1/23:1-OH)/SM (d18:1/24:1) (d18:1/23: 2-OH), Cer(d18:1/24:0)/Cer(d18:1/24:1), Cer(d18:1/24:0)/ SM (d18:1/14:0) (d18:1/13:1-OH), Cer(d18:1/24:0)/Gb3 (d18:1/16:0) and Cer(d18:1/24:0)/SM (d18:1/16:1) (d18:1/ 15:2-OH) (Table 3).

In one particular embodiment, the one or more lipid-lipid concentration ratio(s) whose decrease(s) is (are) compared to the control is (are) selected from: Cer(d18:1/24:0)/PC 16:0/18:2, SM (d18:1/24:0) (d18:1/23:1-OH)/SM (d18:1/24: 1) (d18:1/23:2-OH), Cer(d18:1/24:0)/SM (d18:1/14:0) (d18: 1/13:1-OH), Cer(d18:1/24:0)/Gb3(d18:1/16:0) and Cer(d18: 1/24:0)/SM (d18:1/16:1) (d18:1/15:2-OH) (Table 3).

In yet another alternative embodiment, the present invention relates to a method of choosing an appropriate treatment of CVD and/or one or more of its complications, such as AMI or CVD death, in a subject not undergoing statin treatment, said method comprising determining in a sample from said subject one or more lipid-clinical concentration ratio(s), wherein (an) increased or decreased lipid-clinical concentration ratio(s) in said sample, when compared to a control sample, is (are) indicative of said subject being in need of treatment or a change in, or supplementation of, an already administered treatment, wherein the one or more lipid-clinical concentration ratio(s) whose increase(s) is (are) compared to the control is (are) selected from: GlcCer (d18:1/16:0)/total cholesterol, Gb3(d18:1/16:0)/apolipoprotein A-I, Gb3(d18:1/18:0)/apolipoprotein A-I, Gb3(d18:1/ 16:0)/HDL cholesterol and PC 16:0/18:2/total cholesterol (Table 3);
and wherein the one or more lipid-clinical concentration ratio(s) whose decrease(s) is (are) compared to the control is (are) selected from: Cer(d18:1/24:0)/supersensitive C-reactive protein and PC 18:0/22:6/supersensitive C-reactive protein (Table 3).

For the purposes of the invention, and particularly for lipid-clinical concentration ratios, anApolipoprotein A-I measurement may alternatively be an Apolipoprotein A-II measurement.

In a further aspect, the invention relates to a method of choosing an appropriate treatment of CVD and/or one or more of its complications, such as AMI or CVD death, in a subject not undergoing statin treatment and not suffering from type 2 diabetes mellitus, said method comprising determining in a sample from said subject the concentration(s) of one or more lipid(s), wherein (an) increased or decreased concentration(s) in said sample, when compared to a control sample, is (are) indicative of said subject being in need of treatment or a change in, or supplementation of, an already administered treatment, wherein the one or more lipid(s) whose increase(s) in concentration is (are) compared to the control is (are) selected from: CE 19:1 (oxCE 682.6), GlcCer(d18:1/16:0), SM (d18:1/18:1), CE 20:4, LacCer(d18:1/16:0), Cer 18:1/ 16:0, SM 18:1/16:0 and CE 16:0 (Tables 4a, 6 and 8);
and wherein the one or more lipid(s) whose decrease(s) in concentration is (are) compared to the control is (are) selected from: PC 18:0/22:6, SM (d18:1/23:1) (d18:1/22:2-OH), PC 16:0/22:6, SM 18:1/24:0 and LPC 16:0 (Tables 4a, 6 and 8).

In one particular embodiment, the one or more lipid(s) whose increase(s) in concentration is (are) compared to the control is (are) selected from: CE 19:1 (oxCE 682.6), CE 20:4, Cer 18:1/16:0 and SM 18:1/16:0 (Tables 4a, 6 and 8); and wherein the one or more lipid(s) whose decrease(s) in concentration is (are) compared to the control is (are) selected from: PC 18:0/22:6, SM 18:1/24:0 and LPC 16:0 (Tables 4a, 6 and 8).

In a preferred embodiment, the one or more lipid(s) whose increase(s) in concentration is (are) compared to the control is (are) selected from: GlcCer(d18:1/16:0), CE 20:4, LacCer (d18:1/16:0), Cer 18:1/16:0, SM 18:1/16:0 and CE 16:0 (Table 8);
and the one or more lipid(s) whose decrease(s) in concentration is (are) compared to the control is (are) selected from: PC 16:0/22:6, SM 18:1/24:0 and LPC 16:0 (Table 8).

In one particularly preferred embodiment, the one or more lipid(s) whose increase(s) in concentration is (are) compared to the control is (are) selected from: CE 20:4, Cer 18:1/16:0 and SM 18:1/16:0 (Table 8); and the one or more lipid(s) whose decrease(s) in concentration is (are) compared to the control is (are) selected from: SM 18:1/24:0 and LPC 16:0 (Table 8).

In an alternative embodiment, the present invention relates to a method of choosing an appropriate treatment of CVD and/or one or more of its complications, such as AMI or CVD death, in a subject not undergoing statin treatment and not suffering from type 2 diabetes mellitus, said method comprising determining in a sample from said subject one or more lipid-lipid concentration ratio(s), wherein (an) increased or decreased lipid-lipid concentration ratio(s) in said sample, when compared to a control sample, is (are) indicative of said subject being in need of treatment or a change in, or supplementation of, an already administered treatment, wherein the one or more lipid-lipid concentration ratio(s) whose increase(s) is (are) compared to the control is (are) selected from: Cer(d18:1/18:0)/SM (d18:1/23:1) (d18: 1/22:2-OH), Cer(d18:1/16:0)/PC 18:0/22:6, Cer(d18:1/18: 0)/PC 16:0/22:6, GlcCer(d18:1/16:0)/PC 18:0/22:6, GlcCer (d18:1/18:0)/SM (d18:1/23:1) (d18:1/22:2-OH), Cer(d18:1/ 16:0)/PC 16:0/22:6, Cer(d18:1/20:0)/SM (d18:1/23:1) (d18: 1/22:2-OH), GlcCer(d18:1/18:0)/PC 16:0/22:6, SM (d18:1/ 18:1)/SM (d18:1/23:1) (d18:1/22:2-OH), Cer(d18:1/20:0)/ PC 16:0/22:6, SM (d18:1/16:0) (d18:1/15:1-OH)/SM (d18: 1/23:1) (d18:1/22:2-OH), SM (d18:1/15:0) (d18:1/14:1-OH)/SM (d18:1/23:1) (d18:1/22:2-OH), GlcCer(d18:1/20: 0)/SM (d18:1/23:1) (d18:1/22:2-OH), Cer(d18:1/24:1)/PC 18:0/22:6, SM (d18:1/16:1) (d18:1/15:2-OH)/SM (d18:1/23: 1) (d18:1/22:2-OH), GlcCer(d18:1/16:0)/PC 16:0/22:6, LacCer(d18:1/22:0)/PC 16:0/22:6, LacCer(d18:1/22:0)/SM (d18:1/23:1) (d18:1/22:2-OH), GlcCer(d18:1/20:0)/PC 16:0/22:6, CE 16:0/PC 18:0/22:6, Cer(d18:1/22:0)/PC 18:0/ 22:6, CE 18:2/PC 18:0/22:6, CE 18:1/PC 18:0/22:6, Cer (d18:1/16:0)/Cer(d18:1/24:0), Gb3(d18:1/16:0)/PC 16:0/22: 6, CE 20:4/PC 18:0/22:6, CE 22:6/PC 18:0/22:6, PC 16:0/ 16:0/PC 16:0/22:6, CE 16:0/PC 16:0/22:6, CE 18:2/PC 16:0/22:6, Gb3(d18:1/24:0)/PC 16:0/22:6, CE 18:1/PC 16:0/ 22:6, CE 20:4/PC 16:0/22:6, SM (d18:1/16:1) (d18:1/15:2-OH)/SM (d18:1/24:0) (d18:1/23:1-OH), Cer(d18:1/16:0)/ Cer(d18:1/22:0), CE 16:0/Cer(d18:1/24:0), SM (d18:1/18: 1)/SM (d18:1/24:0) (d18:1/23:1-OH), GlcCer(d18:1/18:0)/ SM (d18:1/24:0) (d18:1/23:1-OH) and SM (d18:1/15:0) (d18:1/14:1-OH)/SM (d18:1/24:0) (d18:1/23:1-OH) (Table 4b);
and wherein the one or more lipid-lipid concentration ratio(s) whose decrease(s) is (are) compared to the control is (are) selected from: Cer(d18:1/24:0)/GlcCer(d18:1/18:0), Cer(d18:1/24:0)/GlcCer(d18:1/16:0), PC 16:0/22:6/SM (d18:1/16:0) (d18:1/15:1-OH), PC 18:0/22:6/SM (d18:1/14:0) (d18:1/13:1-OH), PC 16:0/22:6/SM (d18:1/16:1) (d18:1/15:2-OH), PC 18:0/22:6/SM (d18:1/16:0) (d18:1/15:1-OH), PC 18:0/22:6/SM (d18:1/15:0) (d18:1/14:1-OH), PC 18:0/22:6/SM (d18:1/18:0), PC 18:0/22:6/SM (d18:1/16:1) (d18:1/15:2-OH) and PC 18:0/22:6/SM (d18:1/18:1) (Table 4b).

In a preferred embodiment, the one or more lipid-lipid concentration ratio(s) whose increase(s) is (are) compared to the control is (are) selected from: Cer(d18:1/18:0)/SM (d18:1/23:1) (d18:1/22:2-OH), Cer(d18:1/16:0)/PC 18:0/22:6, Cer(d18:1/18:0)/PC 16:0/22:6, GlcCer(d18:1/16:0)/PC 18:0/22:6, GlcCer(d18:1/18:0)/SM (d18:1/23:1) (d18:1/22:2-OH), Cer(d18:1/16:0)/PC 16:0/22:6, Cer(d18:1/20:0)/SM (d18:1/23:1) (d18:1/22:2-OH), GlcCer(d18:1/18:0)/PC 16:0/22:6, SM (d18:1/18:1)/SM (d18:1/23:1) (d18:1/22:2-OH), Cer(d18:1/20:0)/PC 16:0/22:6, SM (d18:1/16:0) (d18:1/15:1-OH)/SM (d18:1/23:1) (d18:1/22:2-OH), SM (d18:1/15:0) (d18:1/14:1-OH)/SM (d18:1/23:1) (d18:1/22:2-OH), GlcCer(d18:1/20:0)/SM (d18:1/23:1) (d18:1/22:2-OH), Cer (d18:1/24:1)/PC 18:0/22:6, SM (d18:1/16:1) (d18:1/15:2-OH)/SM (d18:1/23:1) (d18:1/22:2-OH), GlcCer(d18:1/16:0)/PC 16:0/22:6, LacCer(d18:1/22:0)/PC 16:0/22:6, CE 16:0/PC 18:0/22:6, CE 18:2/PC 18:0/22:6 and Cer(d18:1/16:0)/Cer(d18:1/24:0) (Table 6);
and the one or more lipid-lipid concentration ratio(s) whose decrease(s) is (are) compared to the control is (are) selected from: PC 18:0/22:6/SM (d18:1/16:1) (d18:1/15:2-OH) and PC 18:0/22:6/SM (d18:1/18:1) (Table 6).

In yet another alternative embodiment the present invention relates a method of choosing an appropriate treatment of CVD and/or one or more of its complications, such as AMI or CVD death, in a subject not undergoing statin treatment and not suffering from type 2 diabetes mellitus, said method comprising determining in a sample from said subject one or more lipid-clinical concentration ratio(s), wherein (an) increased or decreased lipid-clinical concentration ratio(s) in said sample, when compared to a control sample, is (are) indicative of said subject being in need of treatment or a change in, or supplementation of, an already administered treatment, wherein the one or more lipid-clinical concentration ratio(s) whose increase(s) is (are) compared to the control is (are) selected from: Cer(d18:1/16:0)/HDL cholesterol, GlcCer(d18:1/16:0)/apolipoprotein A-I, CE 19:1 oxCE 682.6/apolipoprotein A-I, GlcCer(d18:1/18:0)/apolipoprotein A-I, GlcCer(d18:1/18:0)/HDL cholesterol, GlcCer(d18:1/16:0)/HDL cholesterol, GlcCer(d18:1/20:0)/apolipoprotein A-I, GlcCer(d18:1/18:0)/total cholesterol and Cer(d18:1/16:0)/apolipoprotein B (Table 4c);
and wherein the one or more lipid-clinical concentration ratio(s) whose decrease(s) is (are) compared to the control is (are) selected from: LacCer(d18:1/24:0)/supersensitive C-reactive protein, CE 17:1/supersensitive C-reactive protein, SM (d18:1/16:0) (d18:1/15:1-OH)/supersensitive C-reactive protein, GlcCer(d18:1/24:0)/supersensitive C-reactive protein, Gb3(d18:1/22:0)/supersensitive C-reactive protein, PC 18:0/20:3/apolipoprotein B, PC 16:0/16:1/supersensitive C-reactive protein, PC 16:0/22:6/total cholesterol, PC 16:0/22:6/apolipoprotein B, PC 18:1/18:1/supersensitive C-reactive protein, SM (d18:1/24:1) (d18:1/23:2-OH)/supersensitive C-reactive protein, PC 18:0/18:2/supersensitive C-reactive protein, Cer(d18:1/24:1)/supersensitive C-reactive protein, Cer(d18:1/22:0)/supersensitive C-reactive protein, PC 18:0/22:6/triglycerides, SM (d18:1/18:0)/supersensitive C-reactive protein, PC 18:0/20:3/supersensitive C-reactive protein, SM (d18:1/24:0) (d18:1/23:1-OH)/supersensitive C-reactive protein, PC 16:0/18:1/supersensitive C-reactive protein, SM (d18:1/23:1) (d18:1/22:2-OH)/total cholesterol, PC 18:0/22:6/LDL cholesterol, PC 18:0/22:6/total cholesterol, SM (d18:1/23:1) (d18:1/22:2-OH)/LDL cholesterol, SM (d18:1/23:1) (d18:1/22:2-OH)/apolipoprotein B, PC 18:0/22:6/apolipoprotein B, SM (d18:1/23:0) (d18:1/22:1-OH)/supersensitive C-reactive protein, PC 18:0/18:1/supersensitive C-reactive protein, LPC 16:0/supersensitive C-reactive protein, PC 16:0/22:6/supersensitive C-reactive protein, SM (d18:1/23:1) (d18:1/22:2-OH)/supersensitive C-reactive protein, PC 18:0/22:6/lipoprotein(a) and PC 16:0/18:0/supersensitive C-reactive protein (Table 4c).

In one particular embodiment, the one or more lipid-clinical concentration ratio(s) whose increase(s) is (are) compared to the control is (are) selected from: CE 19:1 (oxCE 682.6)/apolipoprotein A-I, GlcCer(d18:1/18:0)/HDL cholesterol, GlcCer(d18:1/16:0)/HDL cholesterol, GlcCer (d18:1/20:0)/apolipoprotein A-I and GlcCer(d18:1/18:0)/total cholesterol (Table 4c).

In a preferred embodiment, the one or more lipid-clinical concentration ratio(s) whose increase(s) is (are) compared to the control is: Cer(d18:1/16:0)/HDL cholesterol (Table 6); and/or the one or more lipid-clinical concentration ratio(s) whose decrease(s) is (are) compared to the control is (are) selected from: PC 18:0/22:6/LDL cholesterol, PC 18:0/22:6/total cholesterol and PC 18:0/22:6/apolipoprotein B (Table 6).

In another aspect, the present invention relates a method of choosing an appropriate treatment of CVD and/or one or more of its complications, such as AMI or CVD death, in a subject not undergoing statin treatment who is suffering from type 2 diabetes mellitus, said method comprising determining in a sample from said subject the concentration(s) of one or more lipid(s), wherein (an) increased or decreased concentration(s) in said sample, when compared to a control sample, is (are) indicative of said subject being in need of treatment or a change in, or supplementation of, an already administered treatment, wherein the one or more lipid(s) whose increase(s) in concentration is (are) compared to the control is (are) selected from: Gb3(d18:1/24:1), Gb3(d18:1/16:0), GlcCer 18:1/16:0, LacCer 18:1/16:0 and PC 16:0/22:6 (Tables 5a, 7 and 8);
and wherein the one or more lipid(s) whose decrease(s) in concentration is (are) compared to the control is (are) selected from: PC O-16:0/20:4-alkyl, CE 20:4, CE 18:0, CE 14:0, CE 22:6, CE 18:3, GlcCer 18:1/18:0 and SM 18:1/24:0 (Tables 5a, 7 and 8).

In one particular embodiment, the one or more lipid(s) whose increase(s) in concentration is (are) compared to the control is (are) selected from: Gb3(d18:1/24:1), Gb3(d18:1/16:0), GlcCer 18:1/16:0 and LacCer 18:1/16:0 (Tables 5a, 7 and 8);
and wherein the one or more lipid(s) whose decrease(s) in concentration is (are) compared to the control is (are) selected from: PC O-16:0/20:4-alkyl, CE 20:4, CE 22:6, GlcCer 18:1/18:0 and SM 18:1/24:0 (Tables 5a, 7 and 8).

In a preferred embodiment, the one or more lipid(s) whose increase(s) in concentration is (are) compared to the control is (are) selected from: Gb3 18:1/16:0, GlcCer 18:1/16:0, LacCer 18:1/16:0 and PC 16:0/22:6 (Table 8);
and the one or more lipid(s) whose decrease(s) in concentration is (are) compared to the control is (are) selected from: CE 14:0, CE 22:6, CE 18:3, GlcCer 18:1/18:0 and SM 18:1/24:0 (Table 8).

In one particularly preferred embodiment, the one or more lipid(s) whose increase(s) in concentration is (are) compared to the control is (are) selected from: Gb3 18:1/16:0, GlcCer 18:1/16:0 and LacCer 18:1/16:0 (Table 8);
and the one or more lipid(s) whose decrease(s) in concentration is (are) compared to the control is (are) selected from: CE 22:6, GlcCer 18:1/18:0 and SM 18:1/24:0 (Table 8).

In an alternative embodiment, the present invention relates to a method of choosing an appropriate treatment of CVD and/or one or more of its complications, such as AMI or CVD death, in a subject not undergoing statin treatment who is suffering from type 2 diabetes mellitus, said method comprising determining in a sample from said subject one or more lipid-lipid concentration ratio(s), wherein (an) increased or decreased lipid-lipid concentration ratio(s) in said sample, when compared to a control sample, is (are) indicative of said subject being in need of treatment or a change in, or supplementation of, an already administered treatment, wherein the one or more lipid-lipid concentration ratio(s) whose increase(s) is (are) compared to the control is (are) selected from: Gb3(d18:1/24:1)/SM (d18:1/17:0) (d18:1/16:1-OH), Gb3(d18:1/24:1)/PC O-16:0/20:4-alkyl, Gb3 (d18:1/16:0)/SM (d18:1/17:0) (d18:1/16:1-OH), Gb3(d18:1/24:1)/GlcCer(d18:1/24:0), Gb3(d18:1/24:1)/GlcCer(d18:1/22:0) and Gb3(d18:1/22:0)/SM (d18:1/17:0) (d18:1/16:1-OH) (Table 5b);
and wherein the one or more lipid-lipid concentration ratio(s) whose decrease(s) is (are) compared to the control is (are) selected from: CE 18:0/PC 18:0/18:2, PC 18:0/18:2/PE 18:0/18:2, Cer(d18:1/24:0)/PE 18:0/18:2, CE 18:0/CE 18:1, CE 18:2/Gb3(d18:1/16:0), CE 16:0/Gb3(d18:1/16:0), CE 18:0/PC 16:0/22:6, CE 14:0/Gb3(d18:1/24:0), CE 18:0/SM (d18:1/16:0) (d18:1/15:1-OH), CE 18:3/SM (d18:1/14:0) (d18:1/13:1-OH), CE 18:0/PC 16:0/18:2, Cer(d18:1/24:0)/PC O-16:0/18:1-alkyl, CE 18:0/Gb3(d18:1/24:0), CE 18:3/PC 16:0/18:1, PC 18:0/20:3/PC O-16:0/18:1-alkyl, CE 14:0/PC 16:0/16:0, CE 17:1/Gb3(d18:1/16:0), CE 14:0/SM (d18:1/14:0) (d18:1/13:1-OH), PC 18:0/20:3/PE 18:0/18:2, CE 18:0/SM (d18:1/14:0) (d18:1/13:1-OH), CE 14:0/PC 16:0/18:1, CE 18:0/SM (d18:1/24:1) (d18:1/23:2-OH), CE 18:0/Cer(d18:1/16:0), CE 18:0/Cer(d18:1/24:1), CE 18:0/PC 16:0/16:0, CE 18:0/PC 18:1/18:1, CE 18:0/PC 16:0/18:1, CE 20:4/PC O-16:0/18:1-alkyl, CE 18:3/PE 18:0/18:2, CE 20:4/Gb3(d18:1/16:0), CE 14:0/PE 18:0/18:2, CE 18:0/Cer (d18:1/26:1), CE 18:3/Gb3(d18:1/22:0), CE 14:0/Gb3(d18:1/16:0), CE 18:3/PC O-16:0/18:1-alkyl, CE 18:3/Gb3(d18:1/16:0), CE 14:0/PC O-16:0/18:1-alkyl, CE 20:4/Gb3(d18:1/18:0), CE 18:3/Gb3(d18:1/24:1), CE 14:0/Gb3(d18:1/24:1), CE 20:5/PC O-16:0/18:1-alkyl, CE 18:0/Gb3(d18:1/18:0), CE 18:0/Gb3(d18:1/16:0) and CE 18:0/Gb3(d18:1/24:1) (Table 5b).

In one particular embodiment, the one or more lipid-lipid concentration ratio(s) whose decrease(s) is (are) compared to the control is (are) selected from: CE 18:0/PC 18:0/18:2, PC 18:0/18:2/PE 18:0/18:2, Cer(d18:1/24:0)/PE 18:0/18:2, CE 18:0/CE 18:1, CE 18:2/Gb3(d18:1/16:0), CE 16:0/Gb3 (d18:1/16:0), CE 18:0/PC 16:0/22:6, CE 14:0/Gb3(d18:1/24:0), CE 18:0/SM (d18:1/16:0) (d18:1/15:1-OH), CE 18:3/SM (d18:1/14:0) (d18:1/13:1-OH), CE 18:0/PC 16:0/18:2, Cer(d18:1/24:0)/PC O-16:0/18:1-alkyl, CE 18:0/Gb3(d18:1/24:0), CE 18:3/PC 16:0/18:1, PC 18:0/20:3/PC O-16:0/18:1-alkyl, CE 14:0/PC 16:0/16:0, CE 17:1/Gb3(d18:1/16:0), CE 14:0/SM (d18:1/14:0) (d18:1/13:1-OH), PC 18:0/20:3/PE 18:0/18:2, CE 18:0/SM (d18:1/14:0) (d18:1/13:1-OH), CE 14:0/PC 16:0/18:1, CE 18:0/SM (d18:1/24:1) (d18:1/23:2-OH), CE 18:0/Cer(d18:1/16:0), CE 18:0/Cer(d18:1/16:0), CE 18:0/PC 18:1/18:1, CE 18:0/PC 16:0/18:1, CE 20:4/PC O-16:0/18:1-alkyl, CE 18:3/PE 18:0/18:2, CE 20:4/Gb3 (d18:1/16:0), CE 14:0/PE 18:0/18:2, CE 18:0/Cer(d18:1/26: 1), CE 18:3/Gb3(d18:1/22:0), CE 14:0/Gb3(d18:1/16:0), CE 18:3/PC O-16:0/18:1-alkyl, CE 18:3/Gb3(d18:1/16:0), CE 14:0/PC O-16:0/18:1-alkyl, CE 20:4/Gb3(d18:1/18:0), CE 18:3/Gb3(d18:1/24:1), CE 14:0/Gb3(d18:1/24:1), CE 20:5/ PC O-16:0/18:1-alkyl, CE 18:0/Gb3(d18:1/18:0), CE 18:0/ Gb3(d18:1/16:0) and CE 18:0/Gb3(d18:1/24:1) (Table 5b).

In a preferred embodiment, the one or more lipid-lipid concentration ratio(s) whose increase(s) is (are) compared to the control is (are) selected from: Gb3(d18:1/24:1)/SM (d18:1/17:0) (d18:1/16:1-OH), Gb3(d18:1/16:0)/SM (d18:1/17:0) (d18:1/16:1-OH) and Gb3(d18:1/24:1)/GlcCer(d18:1/24:0) (Table 7); and the one or more lipid-lipid concentration ratio(s) whose decrease(s) is (are) compared to the control is (are) selected from: CE 18:3/PC 16:0/18:1, CE 18:0/SM (d18:1/14:0) (d18:1/13:1-OH), CE 14:0/PE 18:0/18:2, CE 18:3/PC O-16:0/18:1-alkyl, CE 18:0/Gb3(d18:1/16:0) and CE 18:0/Gb3(d18:1/24:1) (Table 7).

In yet another alternative embodiment the present invention relates to a method of choosing an appropriate treatment of CVD and/or one or more of its complications, such as AMI or CVD death, in a subject not undergoing statin treatment who is suffering from type 2 diabetes mellitus, said method comprising determining in a sample from said subject one or more lipid-clinical concentration ratio(s), wherein (an) increased or decreased lipid-clinical concentration ratio(s) in said sample, when compared to a control sample is (are) indicative of said subject being in need of treatment or a change in, or supplementation of, an already administered treatment, wherein the one or more lipid-clinical concentration ratio(s) whose increase(s) is (are) compared to the control is (are) selected from: PC 18:1/18:1/lipoprotein(a), PC O-16:0/18:1-alkyl/lipoprotein(a), Gb3 (d18:1/18:0)/lipoprotein(a), SM (d18:1/23:1) (d18:1/22:2-OH)/lipoprotein(a), Gb3(d18:1/24:1)/lipoprotein(a), Gb3 (d18:1/16:0)/lipoprotein(a), PE 18:0/18:2/lipoprotein(a), LacCer(d18:1/24:1)/lipoprotein(a), LacCer(d18:1/22:0)/lipoprotein(a), Gb3(d18:1/22:0)/lipoprotein(a), CE 17:1/lipoprotein(a), Gb3(d18:1/24:0)/lipoprotein(a), PC 16:0/18:2/lipoprotein(a), PC O-18:0/18:2-alkyl/lipoprotein(a), LacCer (d18:1/24:0)/lipoprotein(a), PC 17:0/18:2/lipoprotein(a), SM (d18:1/18:0)/lipoprotein(a), CE 15:0/lipoprotein(a), PC O-16:0/18:2-alkyl/lipoprotein(a), Gb3(d18:1/24:1)/LDL cholesterol, Gb3(d18:1/24:1)/apolipoprotein B, Gb3(d18:1/24:1)/total cholesterol, Gb3(d18:1/24:1)/apolipoprotein A-I, PC O-16:0/18:1-alkyl/LDL cholesterol, Gb3(d18:1/16:0)/ LDL cholesterol, Gb3(d18:1/24:1)/HDL cholesterol, Gb3 (d18:1/22:0)/LDL cholesterol, Gb3(d18:1/18:0)/LDL cholesterol, Gb3(d18:1/24:0)/LDL cholesterol, Gb3(d18:1/16: 0)/apolipoprotein B, PC O-16:0/18:1-alkyl/apolipoprotein B, PC O-16:0/18:1-alkyl/triglycerides, Gb3(d18:1/16:0)/total cholesterol, Gb3(d18:1/22:0)/apolipoprotein B, PC 16:0/ 16:0/LDL cholesterol, Gb3(d18:1/18:0)/apolipoprotein B, PC O-16:0/18:1-alkyl/total cholesterol, SM (d18:1/24:1) (d18:1/23:2-OH)/LDL cholesterol, Gb3(d18:1/16:0)/triglycerides, PE 18:0/18:2/LDL cholesterol, Gb3(d18:1/22:0)/total cholesterol, PE 18:0/18:2/triglycerides, Gb3(d18:1/18:0)/ total cholesterol, PE 18:0/18:2/total cholesterol, PC 16:0/ 18:2/LDL cholesterol, PC 16:0/16:0/total cholesterol, PE 18:0/18:2/apolipoprotein B and SM (d18:1/14:0) (d18:1/13: 1-OH)/total cholesterol (Table 5c);
and wherein the one or more lipid-clinical concentration ratio(s) whose decrease(s) is (are) compared to the control is (are) selected from: CE 14:0/HDL cholesterol and CE 14:0/ supersensitive C-reactive protein (Table 5c).

In a preferred embodiment, the one or more lipid-clinical concentration ratio(s) whose increase(s) is (are) compared to the control is (are) selected from: PC 18:1/18:1/lipoprotein (a), Gb3(d18:1/18:0)/lipoprotein(a), Gb3(d18:1/16:0)/lipoprotein(a) and LacCer(d18:1/24:1)/lipoprotein(a) (Table 7); and the one or more lipid-clinical concentration ratio(s) whose decrease(s) is (are) compared to the control is: CE 14:0/supersensitive C-reactive protein (Table 7).

In connection with all aspects and embodiments of the invention described and claimed herein, the determination of the lipid concentration(s), the lipid-lipid concentration ratio(s) or the lipid-clinical concentration ratio(s) is typically performed using an assay.

In one embodiment of the invention, in which the treatment effectiveness is to be evaluated or the treatment is to be chosen as appropriate in accordance with the methods described and claimed herein, said treatment is a lipid modifying treatment.

The invention further encompasses the analysis of lipid concentrations, lipid-lipid concentration ratios and/or lipid-clinical concentration ratios in samples from a subject that has been previously treated with one or more statins and/or any other HMG-CoA reductase inhibitor.

For the purposes of the invention, at least one lipid concentration, lipid-lipid concentration ratio or lipid-clinical concentration ratio from Tables 3-8, or combinations thereof, may be determined to assess whether the patient is at risk to develop one or more of CVD complications, such as AMI or CVD death; to evaluate the effectiveness of the treatment of CVD and/or one or more of its complications, such as AMI or CVD death in a subject; or to choose an appropriate treatment of CVD and/or one or more of its complications, such as AMI or CVD death in a subject. However, it is also possible, and may be advantageous, to determine at least 2, at least 3, at least 4, at least 5, at least 6, at least 7, or at least 8 lipid concentrations, lipid-lipid concentration ratios or lipid-clinical concentration ratios from Tables 3-8, or combinations thereof, in this regard. Where more than one lipidomic markers are determined and used for the assessment, it may be advantageous that a specific lipid concentration, lipid-lipid concentration ratio, lipid-clinical concentration ratio or combination thereof, is given greater weight than others in the above-mentioned assessment, evaluation or choice.

In the context of the present invention, CVD is typically characterized by coronary artery disease, peripheral artery disease, a stroke and/or CVD death. The CVD in the subject whose sample is analyzed in accordance with the invention may be atherosclerosis-induced. Generally, the invention embodies methods involving subjects who are at risk of developing CVD, and have atherosclerosis. Alternatively, the invention embodies methods involving subjects who are at risk of developing CVD, and do not have atherosclerosis.

In a further embodiment, the methods of the invention may further comprise determining the serum or plasma level of total cholesterol, low-density lipoprotein cholesterol (LDL-C), high-density lipoprotein cholesterol (HDL-C), Apolipoprotein B (ApoB) and/or Apolipoprotein C-III in the subject's sample. In one embodiment of the invention, the subject does not have elevated serum or plasma levels of one or more of total cholesterol, low-density lipoprotein cholesterol (LDL-C), Apolipoprotein C-III or Apolipoprotein B (ApoB), or a decreased serum level of HDL-cholesterol (HDL-C).

In accordance with all aspects and embodiments described and claimed herein, both the sample from the subject and the control sample is preferably a blood sample, more preferably a blood plasma sample, or also preferably a blood serum sample. It may also be urine or tissue or a fraction of blood, blood plasma, blood serum, urine or tissue e.g., a lipoprotein fraction. A blood sample can be prepared and plasma or serum, or fractions thereof, can be separated therefrom with techniques well known to the person skilled in the art. Alternatively, both the sample from the subject and the control sample may also be a tissue sample, e.g., artery tissue, such as carotid artery tissue, or artery plaque material, such as carotid artery plaque material.

Collecting information on a lipidomic marker (i.e., the concentration(s) of (a) lipid(s), lipid-lipid concentration ratio(s), or lipid-clinical concentration ratio(s) or combinations thereof, i.e., corresponding profile(s)) from the sample of a patient and, where appropriate, a corresponding control sample, can be performed with various chemical and high-resolution analytical techniques. Suitable analytical techniques include, but are not limited to, mass spectrometry and nuclear resonance spectroscopy. Any high-resolution technique capable of resolving individual lipids or lipid classes and providing structural information of the same can be used to collect the information on the lipidomic marker in question, e.g., lipid profile from the biological sample. For methods of the present invention the level of the lipid is determined by using mass spectrometry, nuclear magnetic resonance spectroscopy, fluorescence spectroscopy or dual polarisation interferometry, a high performance separation method such as HPLC, UHPLC or UPLC and/or an immunoassay such as an ELISA. According to an alternative or further embodiment an analyte in a sample can be detected and/or quantified by combining the analyte with a binding moiety capable of specifically binding the analyte. The binding moiety can include, for example, a member of a ligand-receptor pair, i.e., a pair of molecules capable of having a specific binding interaction. The binding moiety can also include, for example, a member of a specific binding pair, such as antibody-antigen, enzyme-substrate, nucleic acid-based ligands, other protein ligands, or other specific binding pairs known in the art. In a preferred embodiment, the lipidomic profile is collected with mass spectrometry (MS), wherein the MS instrument may be coupled to direct infusion methods and high performance separation methods such as HPLC, UHPLC or UPLC. The amount of the individual lipids or lipid classes in the collected lipidomic profile is used when comparing the collected lipid profile to a control.

Collecting the information on the lipidomic marker with mass spectrometry (MS) is one of the preferred embodiments of the current invention. The MS instrument can be coupled to a direct sample infusion method, such as a robotic nanoflow ion source device, or to a high performance separation method such as high performance liquid chromatography (HPLC), ultra high pressure liquid chromatography (UHPLC) or ultra performance liquid chromatography (UPLC).

The methods of the present invention may be used for determining a risk of said patient to develop CVD complications, particularly severe CVD complications such as death and myocardial infarction (MI), including acute myocardial infarction (AMI).

In one embodiment of the invention, a method for treating or preventing CVD complications, such as AMI or CVD death, in a subject in need thereof is provided. The method comprises administering a therapeutically effective dose of a drug capable of modulating one or more of the lipid concentration(s), lipid-lipid concentration ratio(s) or lipid-clinical concentration ratio(s) described in Tables 3-8, wherein the dose is such that said one or more lipid concentration(s), lipid-lipid concentration ratio(s) or lipid-clinical concentration ratio(s) in a sample of said subject does not significantly differ when compared to (a) corresponding lipid concentration(s), (a) corresponding lipid-lipid concentration ratio(s) or (a) corresponding lipid-clinical concentration ratio(s) in a control, e.g., a control sample. In a preferred embodiment, the drug is a statin or another HMG-CoA reductase inhibitor. Particularly preferred statins in this regard are atorvastatin, cerivastatin, fluvastatin, fluvastatin XL, lovastatin, pitavastatin, pravastatin, rosuvastatin or simvastatin. In another preferred embodiment, the drug is niacin (nicotinic acid); a cholesterol absorption inhibitor, such as ezetimibe or SCH-48461; a cholesteryl ester transfer protein (CETP) inhibitor, such as torcetrapib, anacetrapib or JTT-705; a bile acids sequestrant, such as colesevelam, cholestyramine or colestipol; or a fibrate, such as fenofibrate, gemfibrozil, clofibrate, or bezafibrate. Alternatively, it may also be a phytosterol or a PCSK9 inhibitor.

Also part of the present invention is a lipid as described herein, e.g. a lipid from any of Tables 3, 4, 5, 6, 7 or 8, for use in preventing or treating a subject at risk to develop CVD complications such as AMI or CVD death. The said lipid may be taken as a dietary supplement or a medicament. A corresponding method of treatment is likewise encompassed. Likewise, the invention also encompasses a modulator for use for modulating a lipid concentration, lipid-lipid concentration ratio or lipid-clinical concentration ratio as described and/or claimed herein, e.g., in Tables 3-8, in a subject at risk to develop CVD and/or one or more of its complications such as AMI or CVD death. A corresponding method of treatment is likewise encompassed. In a further embodiment, the said modulator is a small molecule, an antisense RNA, a small interfering RNA (siRNA) or a natural or modified lipid.

Alternatively, the modulator affects the activity, functionality or concentration of an enzyme, wherein said enzyme catalyzes a reaction that produces or degrades any one of the lipids in Tables 3-8. Similarly, the present invention relates to a preventing or treating a subject at risk to develop CVD complications such as AMI or CVD death, using, or administering a modulator, wherein the modulator affects the activity, functionality or concentration of an enzyme, wherein said enzyme catalyzes a reaction that produces or degrades any one of the lipids in Tables 3-8.

In one embodiment of the present invention, an antibody against any one of the lipids in Tables 3-8 is used for predicting one or more CVD complications such as AMI or CVD death. In another embodiment of the invention, the antibody may be used for preventing or treating one or more of the above complications in a subject.

Any of the methods, drugs, lipids, modulators or antibodies of the present invention may be used for a subject which is at risk to develop or has suffered from one or more CVD complications such as acute myocardial infarction and/or is at risk of cardiovascular death. For the purposes of the invention, CVD complication(s) includes severe CVD complication(s), particularly death.

Also encompassed by the present invention is a kit for predicting CVD and/or one or more of it complications, or for performing the methods or uses described and/or claimed herein, wherein the kit comprises reagents and reference compounds. The reference compounds may be one or more of the following, but are not limited to: (a) (a) lipid standard(s) chosen from the lipids in Tables 3 to 8, (b) one or more control markers (for example, a lipid or lipids, preferably a lipid corresponding to any of the lipidomic markers described and/or claimed herein, or (an) other lipid(s), e.g., total PC, or another molecule, e.g., a protein; c) positive and/or negative controls; d) internal and/or external stan- dards; e) calibration line controls; (f) an antibody or other binding moiety capable of binding any one of the lipids in Tables 3 to 8. The reagents are solution(s), solvent(s), and/or buffer(s) useful for performing said methods or uses.

In one embodiment of the invention, a kit is provided for predicting CVD and/or one or more of its complications, or for performing the methods of the invention, wherein the kit comprises (a) (a) lipid standard(s) chosen from the lipids in Tables 3 to 8, and optionally one or more further reference compound(s) selected from: (b) one or more control markers (for example, a lipid or lipids, preferably a lipid corresponding to any of the lipidomic markers described and/or claimed herein, or another lipid(s), e.g., total PC, or another molecule, e.g., a protein); c) positive and/or negative controls; d) internal and/or external standards, which may or may not be chemically modified, tagged or non-endogenously occurring molecules in human; e) calibration line controls; and (f) an agent, optionally an antibody, capable of binding any one of the lipids in Tables 3 to 8, and (g) (a) reagent(s) for performing said methods or uses.

Preferred kits according to the invention comprise, for example, the following combinations of the above listed constituents: (a) and (b), and optionally (g); (a) and (c), and optionally (g); (a) and (d), and optionally (g); (a) and (e), and optionally (g); (a) and (f), and optionally (g); (a), (b) and (c), and optionally (g); (a), (c) and (d), and optionally (g); (a), (d) and (e), and optionally (g); or (a), (e) and (f), and optionally (g).

In one preferred embodiment, the one or more control marker(s) of the claimed kit is/are (a) molecule(s) that is/are regularly measured in a clinical setting. For example, preferred are embodiments wherein the one or more said control marker(s) is CK.

Preferably, the kit is used for predicting CVD complications, wherein the lipid concentration(s), lipid ratio(s) or (a) lipid combination(s) thereof in a sample from a subject is (are) determined by using mass spectrometry. The sample may be subjected to purification and/or other sample pre-preparation step(s) before mass spectrometry analysis. The purification step may be, but is not limited to chromatography, for example, high performance liquid chromatography (HPLC) and/or ultra high performance liquid chromatography (UHPLC). The sample pre-preparation step may be, but is not limited to solid-phase extraction (SPE), derivatization, liquid-liquid extraction and/or lipoprotein fractionation. The said mass spectrometry determination may be done by tandem mass spectrometry.

As mentioned above, for the purposes of the present invention, a control sample may be obtained from (a) CAD patient(s) or a group of CAD patients that has/have remained free of any major CVD complications e.g., by mixing a variety of samples from said population. If a group of CAD patients is used then several lipid profiles from a population are combined and the lipidomic marker is created from this combination. The levels or amounts of the individual lipids or the lipid-lipid concentration ratios or lipid-clinical concentration ratios in the sample from a subject are compared to the levels or amounts of the lipids or lipid ratios in the control for determining the risk of one or more of CVD complications, such as AMI or CVD death, in said subject.

In one embodiment, the control is a sample from (a) CAD patient(s) wherein the control sample is from (a) CAD patient(s) or a group of CAD patients with no history of major CVD events and who is/are not undergoing statin treatment. The control CAD patient(s) not undergoing statin treatment may or may not have a type 2 diabetes mellitus. It may also be a sample that represents a combination of samples from a CAD patient population not undergoing statin treatment with no history of major CVD events. Alternatively, the control may be a set of data concerning a lipidomic marker in accordance with the present invention, e.g., information on the concentration of (a) lipid(s), lipid-lipid concentration ratio(s), or lipid-clinical concentration ratio(s) in accordance with the present invention in a sample when taken from (a) CAD patient(s) not undergoing statin treatment with no history of major CVD events, or in a combination of samples taken from a CAD patient population not undergoing statin treatment with no history of major CVD events. Said information, and thus the corresponding set of data, may have been previously determined, calculated or extrapolated, or may have yet to be determined, calculated or extrapolated, or may also be taken from the literature.

Alternatively, the control is a sample from (a) CAD patient(s) wherein the control sample is from (a) CAD patient(s) or a group of CAD patients with no history of major CVD events and who is/are undergoing statin treatment. The control CAD patient(s) undergoing statin treatment may or may not have a type 2 diabetes mellitus. It may also be a sample that represents a combination of samples from a CAD patient population undergoing statin treatment with no history of major CVD events. Alternatively, the control may be a set of data concerning a lipidomic marker in accordance with the present invention, e.g., information on the concentration of (a) lipid(s), lipid-lipid concentration ratio(s), or lipid-clinical concentration ratio(s) in accordance with the present invention in a sample when taken from (a) CAD patient(s) undergoing statin treatment with no history of major CVD events, or in a combination of samples taken from a CAD patient population undergoing statin treatment with no history of major CVD events. Said information, and thus the corresponding set of data, may have been previously determined, calculated or extrapolated, or may have yet to be determined, calculated or extrapolated, or may also be taken from the literature.

Preferably, the control sample is blood, plasma, serum, urine or tissue, or a lipoprotein fraction thereof.

In another aspect, the present invention relates to a statin or a lipid lowering drug for use in the treatment of a subject at risk to develop one or more CVD complications, such as acute myocardial infarction (AMI) and/or CVD death, wherein said subject would be identified as being at risk to develop one or more CVD complications when applying any of the methods, drugs, lipids, modulators, kits or uses described and/or claimed herein. Similarly, the present invention relates to a method of treating a subject at risk to develop one or more CVD complications with a statin or a lipid lowering drug, wherein said subject would be identified as being at risk to develop one or more CVD complications when applying any of the methods, drugs, lipids, modulators, kits or uses described and/or claimed herein.

In a further embodiment, the present invention relates to a statin or a lipid lowering drug for use in the treatment of a subject at risk to develop one or more CVD complications, such as AMI and/or CVD death, wherein said subject actually has been identified as being at risk to develop one or more CVD complications by any of the methods, drugs, lipids, modulators, kits or uses described and/or claimed herein. Similarly, the present invention relates to a method of treating a subject at risk to develop one or more CVD complications with a statin or a lipid lowering drug, wherein said subject actually has been identified as being at risk to develop one or more CVD complications by any of the methods, drugs, lipids, modulators, kits or uses described and/or claimed herein.

In yet another aspect, the present invention relates to a statin or a lipid lowering drug for use in the treatment of a subject at risk to develop one or more CVD complications, such as AMI and/or CVD death, wherein said subject would be identified as not being at risk to develop or as not suffering from one or more CVD complications when applying any of the methods, drugs, lipids, modulators, kits or uses described and/or claimed herein. Similarly, the present invention relates to a method of treating a subject at risk to develop one or more CVD complications with a statin or a lipid lowering drug, wherein said subject would be identified as not being at risk to develop one or more CVD complications when applying any of the methods, drugs, lipids, modulators, kits or uses described and/or claimed herein.

In a further embodiment, the present invention relates to a statin or a lipid lowering drug for use in the treatment of a subject at risk to develop one or more CVD complications, such as AMI and/or CVD death, wherein said subject actually has been identified as not being at risk to develop or as not suffering from statin-induced muscle toxicity by any of the methods, drugs, lipids, modulators, kits or uses described and/or claimed herein. Similarly, the present invention relates to a method of treating a subject at risk to develop one or more CVD complications with a statin or a lipid lowering drug, wherein said subject actually has been identified as not being at risk to develop one or more CVD complications by any of the methods, drugs, lipids, modulators, kits or uses described and/or claimed herein.

In the present invention herein, lipid biomarker concentrations have been measured and quantified in patients with documented CAD who did not show fatal outcomes during the follow-up period (3 years) and in high-risk CAD patients who died due to cardiovascular events during the follow-up period. This invention thus enables accurate usage of the lipid-based biomarkers to identify high risk CVD/CAD patients. Another layer of accuracy was reached through a careful patient selection since it is important to control for factors which may affect the lipid concentration read-outs. Unlike the previous efforts described above, we used specific targeted platforms on a singular technology set-up to analyze lipid species in particular.

The technology and the way it was applied in the context of the inventive teaching presented herein is set apart from similar efforts in the field inter alia due to the following criteria. In sample preparation, samples are strictly controlled and treated identically to avoid potential artifacts that could arise from improper handling. In connection with the present invention, samples were carefully thawed slowly on ice and directly thereafter subjected to a custom-made automated lipid extraction which possesses currently the highest precision in liquid handling, therefore minimizing potential errors. Furthermore, sample freeze-thaw cycles were strictly controlled since this can dramatically affect the lipid stabilities. The automated lipid extraction is based on the method by Folch and colleagues (Folch J, et al: *A simple method for the isolation and purification of total lipids from animal tissues. J Biol Chem* 1957, 226(1):497-509) which uses chloroform and methanol. This method is preferred when a wide range, from polar to non-polar, of lipid classes are to be extracted with optimal recoveries thus preventing the loss of lipid species. Lipid class specific non-endogenous lipids, when applicable, were used as internal standards to gain highest precision in identification (minimizing false positives) and quantification of monitored molecular lipid species. In this way absolute or semi-absolute amounts of endogenous molecular lipids were determined with the highest precision that can be achieved with today's technologies. The endogenous lipids and respective standards were monitored at the molecular lipid level. In this way, not only false positive identifications were minimized, but molecular lipids could be precisely determined and quantified. Analysis quality was strictly controlled using a novel quality control system. This was mainly controlled by multiple internal standards (IS), external standards (ES), IS/ES ratios, and instrument control samples. By stringently controlling these components, technical and biological outliers were readily identified and rejected from further analysis. To obtain best precision in sensitivity, selectivity and quantification for each molecular lipid different targeted platforms were used. Some lipids are best analyzed using high performance liquid chromatography (HPLC) or ultra high performance liquid chromatography (UHPLC) combined with mass spectrometry based multiple reaction monitoring (MRM) whereas others are best analyzed by direct infusion in combination with mass spectrometry-based precursor ion scanning and neutral loss scanning techniques.

DETAILED DESCRIPTION OF THE INVENTION

Definitions

Coronary vascular disease/cardiovascular disease (CVD) has its general meaning in the art and is used to classify numerous conditions that affect the heart, heart valves, blood, and vasculature of the body, including CAD. In the present invention the terms CVD and CAD may be used interchangeably. For the purposes of the invention, CVD/CAD patients, in one embodiment, exclude patients with Acute Coronary Syndrome (ACS). In an alternative embodiment, ACS is included in CVD/CAD. Cardiovascular diseases in accordance with the present invention include endothelial dysfunction, coronary artery disease, angina pectoris, myocardial infarction, atherosclerosis, congestive heart failure, hypertension, cerebrovascular disease, stroke, transient ischemic attacks, deep vein thrombosis, peripheral artery disease, cardiomyopathy, arrhythmias, aortic stenosis, and aneurysm. Such diseases frequently involve atherosclerosis. In a preferred embodiment of the invention, the cardiovascular disease is a cardiovascular disease associated with atherosclerosis.

CAD is coronary artery disease, AMI is acute myocardial infarction, ACS is acute coronary syndrome, CAC is coronary artery calcification, RCT is reverse cholesterol transport, LDL is low density lipoprotein, HDL is high density lipoprotein, LDL-C is low density lipoprotein cholesterol, HDL-C is high density lipoprotein cholesterol, ApoA is Apolipoprotein A, ApoB is Apolipoprotein B, ApoC is apolipoprotein C, MS is mass spectrometry, HPLC is high performance liquid chromatography, UHPLC is ultra high performance liquid chromatography and UPLC is ultra performance liquid chromatography.

As used herein, "a subject" includes all mammals, including without limitation humans, but also non-human primates, dogs, cats, horses, sheep, goats, cows, rabbits, pigs and rodents. A particularly preferred "subject" is a human.

A "sample" is defined as any biological sample obtained from a subject or a group or population of subjects. For the purposes of the present invention, the biological sample may be whole blood, blood serum, blood plasma or a fraction of blood; e.g., a lipoprotein fraction. It may also be a tissue sample. However, a preferred embodiment is wherein the biological sample is plasma or serum. Taking a blood sample of a patient is part of normal clinical practice. The blood sample can be taken in connection with e.g. measuring the cholesterol levels in the patients. The collected blood sample can be prepared and serum or plasma can be separated with techniques well known to a person skilled in the art. Vena blood samples can be collected from patients using a needle and a BD Vacutainer® Plastic Tubes or Vacutainer® Plus Plastic Tubes (BD Vacutainer® SST™ Tubes contain spray-coated silica and a polymer gel for serum separation). Serum can be separated by centrifugation at 1300 RCF for 10 min at room temperature and stored in small plastic tubes at −80° C. The lipoprotein fractions may be separated by precipitation, ultracentrifugation, by chromatography or by gel filtration with methods well known in the art.

For the purposes of the present invention, lipids from the Lipidomic analysis were named according to the following nomenclature: CE is cholesteryl ester, Cer is ceramide, DAG is diacylglycerol, PC O is ether-linked PC, Gb3 is globotriaosylceramide, GlcCer is galactosyl- and glucosylceramides, LacCer is lactosylceramides, LPC is lysophosphatidylcholine, PC is Phosphatidylcholine, PE is Phosphatidylethanolamine, PI is Phosphatidylinositol and SM is Sphingomyelin.

The nomenclature X:Y indicates, X number of total carbon atoms in the fatty acid(s) portions of the molecule, and Y the total number of double bonds in the fatty acid portion(s) of the molecule.

The nomenclature A/B indicates, for a molecule of DAG and PC, A and B types of fatty acid moieties attached to the glycerol backbone of the molecule.

The nomenclature (dC/A) indicates, for a molecule of Cer, Gb, GlcCer, LacCer and SM, C the type of long-chain base with an amide-linked, A, fatty acid moiety.

According to the invention, the treatment of CVD and/or one or more of its complications, such as AMI or CVD death, in a subject not undergoing statin treatment, does not involve treatment with a statin. For example, the said treatment may be one with a niacin (nicotinic acid); a cholesterol absorption inhibitor, such as ezetimibe or SCH-48461; a cholesteryl ester transfer protein (CETP) inhibitor, such as torcetrapib, anacetrapib or JTT-705; a bile acids sequestrant such as colesevelam, cholestyramine and colestipol; a fibrate, such as fenofibrate, gemfibrozil, clofibrate, and bezafibrate; a phytosterol, or a PCSK9 inhibitor.

The wording "compared to a control sample" as used herein will be understood to include embodiments where control samples are actually analyzed in respect of a lipidomic marker of interest, i.e., in respect of the concentration of one or more of the lipid(s), the lipid-lipid concentration ratios, or the lipid-clinical concentration ratios or combinations thereof as specifically described and/or claimed herein in connection with the various aspects and embodiments of the present invention. It will be appreciated, however, that the above wording also includes embodiments where the corresponding information on said lipidomic marker in said control sample is merely taken from the literature, or has been previously determined, calculated or extrapolated, or is yet to be determined, calculated or extrapolated.

As used herein, the term "antibody" includes monoclonal and polyclonal antibodies, whole antibodies, antibody fragments, and antibody sub-fragments that exhibit specific binding to a said lipid. Thus, suitable "antibodies" can be whole immunoglobulins of any class, e.g., IgG, IgM, IgA, IgD, IgE, chimeric antibodies or hybrid antibodies with dual or multiple antigen or epitope specificities, or fragments, e.g., F(ab')2, Fab', Fab and the like, including hybrid fragments, and additionally includes any immunoglobulin or any natural, synthetic or genetically engineered protein that acts like an antibody by binding to a specific antigen to form a complex. The term "antibody" encompasses antigen-binding fragments of antibodies (e.g., single chain antibodies, Fab fragments, F(ab')2, an Fd fragment, an Fv fragment, a dAb (single (variable) domain antibody), or a nanobody) as well as complete antibodies. For example, Fab molecules can be expressed and assembled in a genetically transformed host like *E. coli*. A lambda vector system is available thus to express a population of Fab's with a potential diversity equal to or exceeding that of the predecessor antibody. See Huse W D, et al., *Science* 1989, 246:1275-81. Such Fab's are included in the definition of "antibody." The ability of a given molecule, including an antibody fragment or sub-fragment, to act like an antibody and specifically bind to a specific antigen can be determined by binding assays known in the art, for example, using the antigen of interest as the binding partner.

Antibodies against lipids in accordance with the present invention may be prepared by methods well known to those skilled in the art. For example, mice may be immunized with a lipid with adjuvant. Splenocytes are harvested as a pool from the mice that were administered 3 immunizations at 2-week intervals with test bleeds performed on alternate weeks for serum antibody titers. Splenocytes are prepared as 3 aliquots that are either used immediately in fusion experiments or stored in liquid nitrogen for use in future fusions.

Fusion experiments are then performed according to the procedure of Stewart & Fuller, *J. Immunol. Methods* 1989, 123:45-53. Supernatants from wells with growing hybrids are screened by enzyme-linked immunosorbent assay (ELISA) for monoclonal antibody (MAb) secretors on 96-well ELISA plates coated with the said lipid. ELISA positive cultures are cloned by limiting dilutions, typically resulting in hybridomas established from single colonies after 2 serial cloning experiments.

EXAMPLES

Example 1

Materials and Methods

This study is a sub-cohort of the LURIC study that is a large scale prospective study on cardiovascular epidemiology. LURIC database contains clinical information over 3000 patients including baseline coronary angiography, clinically used biomarker data and also e.g. CVD mortality data for the follow-up period (3 years). In this biomarker study the inventors compared CAD cases not undergoing statin treatment (n=123) that died during the follow-up due to CVD with patients (n=96) having a stable CAD also not undergoing statin treatment. Subjects with a significant atherosclerosis level in the angiogram but no CVD related death during the follow-up were used as controls, while the case group had similarly a significant atherosclerosis based on the angiography at baseline and in addition they died during the follow-up due to acute cardiovascular events. A statistical analysis was performed separately for cases (n=55) and controls (n=46) without diabetes and for cases (n=68) and controls (n=50) having diabetes. The clinical characteristics for these two groups are described in Tables 1 and 2.

TABLE 1

Background characteristics of subjects not undergoing statin treatment and not having type 2 diabetes mellitus

| Clinical characteristics | Controls (n = 46) | Cases (n = 55) |
|---|---|---|
| DM2 patients | 0 | 0 |
| Hypertensive patients | 27 (58.7%) | 32 (58.2%) |
| Smokers (active or quit less than 3 years before sampling) | 13 (28.3%) | 17 (30.9%) |
| Statin users | 0 | 0 |
| Age | 66.9 | 67.6 |
| Apolipoprotein A-I | 134.0 | 125.2 |
| Apolipoprotein B | 104.0 | 106.8 |
| BMI | 27.2 | 26.3 |
| HDL cholesterol | 41.3 | 38.2 |
| LDL cholesterol | 121.8 | 124.8 |
| Lipoprotein(a) | 22.8 | 26.4 |
| Supersensitive C-reactive protein | 7.4 | 17.2 |
| Total cholesterol | 194.8 | 195.5 |
| Triglycerides | 138.0 | 145.6 |

TABLE 2

Background characteristics of subjects not undergoing statin treatment and having type 2 diabetes mellitus

| Clinical characteristics | Controls (n = 50) | Cases (n = 68) |
|---|---|---|
| DM2 patients | 50 (100%) | 68 (100%) |
| Hypertensive patients | 35 (70%) | 41 (60.4%) |
| Smokers (active or quit less than 3 years before sampling) | 18 (36%) | 21 (30.9%) |
| Statin users | 0 | 0 |
| Age | 65.1 | 69.0 |
| apolipoprotein A-I | 124.0 | 116.9 |
| apolipoprotein B | 115.5 | 106.7 |
| bmi | 27.8 | 28.0 |
| HDL cholesterol | 35.2 | 34.1 |
| LDL cholesterol | 126.0 | 114.4 |
| lipoprotein(a) | 32.0 | 15.6 |
| supersensitive C-reactive protein | 5.3 | 11.5 |
| total cholesterol | 205.6 | 189.9 |
| triglycerides | 194.4 | 183.3 |

Definition of Cases: All cases had significant artery disease (>=20% stenosis) in coronary angiogram and they all died due to CVD during the follow-up. Thus, these CAD patients have an elevated risk for CVD outcomes. Majority (75%) of cases, were non-ACS patients. Definition of Controls: All controls had significant artery disease (>=20% stenosis) in coronary angiogram, but they did not die due to CVD during the follow-up. The control subjects did not have any history of MI or stroke before the baseline evaluation. Thus, these patients can be considered to be CAD patients with a low risk for CVD outcomes.

Example 2

Analytical Methods

Mass Spectrometry Driven Lipidomics

Direct infusion coupled to tandem mass spectrometry, i.e. shotgun lipidomics, and two liquid chromatography tandem mass spectrometry (LC-MS/MS) approaches, i.e. ceramide and cerebroside lipidomics and ganglioside lipidomics, were used to identify lipid biomarkers for coronary artery disease (CVD) risk by analyzing molecular lipid species in human serum, plasma, and carotid artery plaques. The applied methods were optimized especially for quantification of molecular cholesteryl esters (CE), phosphatidylcholines (PC), lysophosphatidylcholines (LPC) and other lysophospholipids (LPL), ether-linked phosphatidylcholines (PC O) and other ether-linked phospholipids (PL O), phosphatidylserines (PS), phosphatidylethanolamines (PE), phosphatidylglycerols (PG), phosphatidylinositols (PI), phosphatidic acids (PA), diacylglycerols (DAG), ceramides (Cer), glucosylceramides (GlcCer), Globotriaosylceramide (Gb3) and lactosylceramides (LacCer).

The following materials were used according to the methods. HPLC or LC-MS grade of chloroform, methanol, water, acetonitrile, formic acid, methanol, isopropanol, ammonium acetate, acetic acid, potassium chloride and butylated hydroxytoluene (BHT) were purchased from Sigma-Aldrich (St. Louis, Mo., USA).

HPLC column (Acquity BEH C18, 2.1×50 mm id. 1.7 μm) was purchased from Waters (Milford, Mass., USA). HPLC pre-column (Widepore C18 4×2.0 mm) was purchased from Phenomenex (Torrance, Calif., USA). All labware used for the extraction were resistant to chloroform. Aerosol resistant filter tips (Molecular BioProducts) and Eppendorf 2 ml safe-lock tubes, 96-well twin.tec PCR plates, and Pierce-it-lite thermo-sealing foils were purchased from VWR International (West Chester, Pa., USA). CO-RE Filter Tips and 96-well 2 ml Whatman Uniplates were purchased from Hamilton Robotics (Bonaduz, Switzerland). Synthetic lipid standards were purchased from Avanti Polar Lipids (Alabaster, Ala., USA) and from Matreya (Pleasant Gap, Pa., USA).

Lipids were extracted in chloroform:methanol according to the following protocols. Samples were spiked with known amounts of non-endogenous synthetic internal standards for data normalization and endogenous lipid quantification. Post-extract spiked non-endogenous synthetic external standards were used for quality controlling. Stock solutions of standards were prepared by dissolving appropriately weighed amounts of each standard in chloroform:methanol (2:1, V:V) to achieve a final concentration of 500 μM. An internal standard mixture containing each of the standard stock was created and used in lipid extraction.

Samples and quality control samples for each extraction batch were thawed on ice. The carotid artery plaque samples were weighed on ice by using a cryo-box and homogenized in ice-cold 70% methanol in water. The Mixer Mill 301 Teflon adapters were kept at −20° C. Homogenization was performed at 15-25 Hz for 2-15 minutes with Mixer Mill 301 (Retch GmbH, Germany).

Lipid extraction of human samples was carried out in automated fashion using a Hamilton MICROLAB STAR system (Hamilton Robotics, Switzerland). Well-mixed samples were aliquoted into a 96-well 2 ml Whatman Uniplate containing ice-cold methanol and 0.1% BHT. 5 μl of serum and plasma and 30 μl of carotid artery plaques were used for shotgun- and ceramide and cerebroside lipidomics and 100 μl of serum and plasma and 200 μl of carotid artery plaques was used for ganglioside lipidomics. The samples were mixed thoroughly after each step in the extraction protocol. The extraction proceeded at room temperature by adding an appropriate volume of internal standard mixture and chloroform, and methanol and water in the case of ganglioside lipidomics. In shotgun and ceramide and cerebroside lipidomics, the organic phase separation was facilitated by adding 20 mM acetic acid and centrifuging the plate for 5 min at 500×g. The organic phase was transferred into a new 96-well 2 ml Whatman Uniplate. The remaining water-containing phase was washed by adding appropriate volume of chloroform followed by centrifugation. The two organic phases were pooled and evaporated under $N_2$ until dryness. The lipid extracts were then re-dissolved in chloroform:methanol (1:2, v:v) including the addition of the synthetic external standard.

In shotgun lipidomics, lipid extracts were analyzed on a hybrid triple quadrupole/linear ion trap mass spectrometer (QTRAP 5500, AB Sciex) equipped with a robotic nanoflow ion source (NanoMate HD, Advion Biosciences). The instruments were operated in positive and negative ion modes. In positive ion the spray voltage was set to 1.0 to 1.4 kV and in negative ion mode to −1.0 to −1.4 kV. A gas pressure of 0.3-0.8 psi was used and the interface heater was set at 60° C. The collision energy (CE) and declustering potential (DP) was optimized for each lipid class using synthetic standards. The mass spectrometer was operated in unit resolution mode using a scan speed of 200 Da/s. Molecular lipids were analyzed in both positive and negative ion modes using multiple precursor ion scanning (MPIS) and neutral loss scanning (NLS) as described by Ståhlman and colleagues (Ståhlman M, et al. High-throughput shotgun lipidomics by quadrupole time-of-flight mass spectrometry. J Chromatogr B Analyt Technol Biomed Life Sci 2009).

In ceramide and cerebroside lipidomics, the high performance liquid chromatography (HPLC) analyses were conducted in the following way. Chromatographic apparatus consisted of a CTC HTC PAL autosampler (CTC Analytics AG, Switzerland), a Rheos Allegro UHPLC pump (Flux Instruments AG, Switzerland), an external column heater set to 60° C. for ceramide and cerebroside lipidomics and 45° C. for ganglioside lipidomics, and the Acquity BEH C18 column with an in-line pre-column. The extracted samples, 10 μl of each, were injected into the pre-column followed by the analytical column and delivered to the mass spectrometer at a flow rate of 500 μl/min. In ceramide and cerebroside lipidomics, A gradient was used for lipid analyte separation with solvent A comprising 10 mM ammonium acetate in HPLC grade water containing 0.1% formic acid and solvent B of 10 mM ammonium acetate in acetonitrile:isopropanol (4:3, V:V) containing 0.1% formic acid. The gradient was constructed in the following way: 0 min—65% B; 2 min—65% B; 2.5 min—75% B; 17.5 min—100% B; 22.5 min—100% B; 22.6 min—65% B; 25 min—65% B.

The lipid extracts were analyzed by HPLC-MS/MS. The MS analysis was performed on a hybrid triple quadrupole/linear ion trap mass spectrometer equipped with the Turbo V™ Ion Source (4000 QTRAP, AB Sciex). The instrument was operating in positive and negative ion modes. The ion source voltage was set to 5500V for ceramide and cerebroside lipidomics and to −4500V for ganglioside lipidomics, and source temperature at 400° C. The collision energy (CE) and declustering potential (DP) was optimized for each lipid class using synthetic standards. A 20 sec dwell time was applied for each scan. Multiple reaction monitoring (MRM) scan mode was applied and based on the description by Sullards and colleagues (Sullards M C, et al: *Structure-specific, quantitative methods for analysis of sphingolipids by liquid chromatography-tandem mass spectrometry: "inside-out" sphingolipidomics. Methods Enzymol* 2007).

The data processing was done in the following way. Initially the retention time (in LC mode) and identification of each peak was done using endogenous standards and by Information Dependent Acquisition (IDA) experiments where applicable. The raw data were processed according to peak detected and retention time (in LC mode) in automated fashion. A stringent cutoff was applied for separating background noise from actual lipid peaks. Each sample was controlled and only accepted when fulfilling the stringent acceptance criteria. Peak area counts (cps) of detected peaks were converted into a list of corresponding lipid names. Lipids were normalized to their respective internal standard and sample volume or tissue weight to retrieve their concentrations.

Several quality controls were used in the lipidomic analyses. A calibration line using synthetic or isolated standards was obtained prior to sample analysis. Synthetic standards were chosen based on application and had similar properties to the endogenous lipids or analyte(s) of interest. The calibration line consisted of a minimum of five standards points covering the expected quantification range. A sample extracted without standard and standards extracted with no matrix, were included with the calibration line.

The calibration line was used to determine the dynamic quantification range for each lipid class monitored, e.g., the linear quantification limits. As the internal standards used behave in the same way as endogenous lipids they were used for quantifying endogenous lipid species. The calibration lines were based on the same internal standards that were used for quantification of the endogenous lipids.

In each sample extracted for lipids, the ratio of synthetic internal standards (IS) to corresponding post-extract spiked external standard (ES) was determined. The peak area (cps) ratio of internal to external standard (IS/ES) was used for calculating the Coefficient of Variation (CV) across all samples. The IS/ES ratio enabled the calculation of lipid extraction recovery.

Instrument control (IC) was included at the start, middle and end of each run. IC sample analyzed was an extracted reference plasma sample and a set of standards to monitor the instrument's performance, i.e., the intra- and inter-assay variation.

For each platform, a stringent cutoff was applied for separating background noise from actual lipid peaks. Each sample was controlled and only accepted when fulfilling the stringent acceptance criteria. Masses and counts of detected peaks were converted into a list of corresponding lipid names. Lipids were normalized to their respective internal standard and sample volume to retrieve their concentrations.

Statistical Analyses

Percentage changes in lipid concentrations between control and case groups were calculated as follows:

$$100*(AVG[C] \text{ in case group} - AVG[C] \text{ in control group})/AVG[C] \text{ in control group}$$

Statistical significance was assigned based on standard t-test p-values.

In addition, ROC curves were used for finding lipid molecules and concentration cutoffs that separate the best cases from controls. Selectivity is calculated as a number of correctly identified cases divided by the total number of cases. Specificity is calculated as a number of correctly identified controls divided by the total number of controls. Selectivity and specificity was calculated for each lipid concentration, lipid to lipid ratio and ratio of lipid to clinical concentrations.

Example 3

Ethics

The LURIC study was approved by the ethics review committee at the "Landesärztekammer Rheinland-Pfalz" (Mainz, Germany). Written informed consent was obtained from each of the participants.

Results

In this LURIC study sub-cohort, the traditional biomarkers including LDL-cholesterol and HDL-cholesterol concentrations were practically identical in both groups and therefore were not predictive of CVD-related for predicting severe CVD/CAD-associated complications, including AMI, stroke and CVD death in this study.

Multiple lipidomic markers appeared as significant predictors of severe CVD/CAD-associated complications (Tables 3-8). A total of 162 molecular lipids were quantified. The significant predictors were selected based on the top fifty candidates from each category, when available. The biomarker candidates were selected according to the following criteria: t-test p-value≤0.05 or sensitivity≥60% and specificity≥60%. From traditional clinical chemistry only apolipoprotein A1 and total cholesterol reached statistical significance with p-value lower than 0.05, but % change was less than 10% between controls and cases, other clinical values did not show any statistical significance. The predictive value of new lipidomic biomarkers was increased when their levels were expressed as distinct lipid-lipid concentration ratios or lipid-clinical ratios (e.g. LDL-C or HDL-C).

Furthermore, to demonstrate improved diagnostic potential, logistic models were fitted in order to find different combinations of lipids that could separate cases and controls from each other. The lipids were set as possible explanatory variables and model was selected using stepwise method with different entry and stay significance levels. The markers with best diagnostic potential are listed in Table 8.

Importance of Detailed Molecular Lipid Analyses

Recent evolvement of mass spectrometry driven lipid analysis approaches has made it possible to resolve complex lipidomes to their molecular lipid species level at high-throughput and quality required for analyses of clinical cohorts. As a result of the high sensitivity and selectivity of the methods, a lipidome-wide analysis of minute sample amounts has become feasible. Present technologies are capable of identifying lipids with different sum compositions, i.e. phosphatidylcholine (PC) 34:1, but more important is the identification of molecular lipid species, e.g. PC 16:0/18:1. In the latter analysis, information of the type of fatty acids and their positions attached to the glycerol backbone making up the particular PC molecule is retrieved.

The seminal work of Shinzawa-Itoh and colleagues showed by highly sophisticated experiments that the oxygen transfer mechanism in cytochrome c oxidase requires a specific phosphatidylglycerol molecular lipid with palmitate and vaccenate at the sn-1 and sn-2 positions respectively on the glycerol backbone (Shinzawa-Itoh K, Aoyama H, Muramoto K et al: *Structures and physiological roles of 13 integral lipids of bovine heart cytochrome c oxidase. EMBO J* 2007, 26:1713-1725). In line with other studies, this undoubtedly indicates that the lipid structure is an essential determinant of the biological effect. Therefore, molecular lipidomics is an essential for biomarker discovery. FIG. 1 illustrates the importance of molecular lipid data by comparing the biomarker value of two PC and LacCer molecules in predicting CVD mortality in the LURIC cohort. The data reveals that while LacCer(d18:1/20:0) is a significant CVD predictor, LacCer (d18:1/18:16:0) has low biomarker potential. In addition, two PC molecules PC (18:0/20:4) and PC (18:0/16:0) have even opposite effects on CVD complications. Thus, it is always necessary to identify and quantify all lipid species for lipid classes of interest including but not limited to cholesterol esters, different phospholipid classes, ceramides, cerebrosides (lactosylceramides, glycosylceramides, globotriaosylceramides).

TABLE 3

Significant markers (lipid-lipid concentration ratios and lipid-clinical concentration ratios) for CVD patients not undergoing statin treatment. Lipid names, p-values, % change, AUC, Sensitivity and Specificity are presented.

| Measurement name | P-value | Percentage change | AUC | Sensitivity | Specificity |
|---|---|---|---|---|---|
| *Lipid-lipid concentration ratios* | | | | | |
| *Increased* | | | | | |
| Gb3(d18:1/16:0)/PC 18:0/22:6 | 0.00054 | 50.7 | 0.73 | 69.0 | 66.7 |
| Cer(d18:1/18:0)/Cer(d18:1/24:0) | 0.00208 | 43.6 | 0.73 | 71.7 | 71.7 |
| Cer(d18:1/20:0)/Cer(d18:1/24:0) | 0.00056 | 35.0 | 0.70 | 68.6 | 60.9 |
| SM (d18:1/16:0) (d18:1/15:1-OH)/SM (d18:1/24:0) (d18:1/23:1-OH) | | 21.2 | 0.74 | 72.2 | 62.2 |
| Cer(d18:1/22:0)/Cer(d18:1/24:0) | 0.00153 | 12.1 | 0.70 | 74.5 | 65.2 |
| *Decreased* | | | | | |
| Cer(d18:1/24:0)/PC 16:0/18:2 | 0.02011 | −13.2 | | | |
| SM (d18:1/24:0) (d18:1/23:1-OH)/SM (d18:1/24:1) d18:1/23:2-OH) | 0.00811 | −15.1 | | | |
| Cer(d18:1/24:0)/Cer(d18:1/24:1) | 0.00062 | −16.9 | 0.70 | 74.5 | 60.9 |
| Cer(d18:1/24:0)/SM (d18:1/14:0) (d18:1/13:1-OH) | 0.01940 | −17.3 | | | |
| Cer(d18:1/24:0)/Gb3(d18:1/16:0) | 0.00517 | −20.1 | 0.68 | 64.8 | 65.2 |
| Cer(d18:1/24:0)/SM (d18:1/16:1) (d18:1/15:2-OH) | 0.00327 | −20.8 | 0.66 | 72.7 | 60.0 |
| *Lipid - clinical concentration ratios* | | | | | |
| *Increased* | | | | | |
| GlcCer(d18:1/16:0)/total cholesterol | 0.02241 | 21.6 | | | |
| Gb3(d18:1/16:0)/apolipoprotein A-I | 0.01039 | 21.2 | 0.63 | 64.8 | 60.9 |
| Gb3(d18:1/18:0)/apolipoprotein A-I | 0.03763 | 20.3 | | | |
| Gb3(d18:1/16:0)/HDL cholesterol | 0.04197 | 19.7 | 0.65 | 61.1 | 63.0 |
| PC 16:0/18:2/total cholesterol | | 1.6 | 0.55 | 63.6 | 60.9 |
| *Decreased* | | | | | |
| Cer(d18:1/24:0)/supersensitive C-reactive protein | | −27.5 | 0.66 | 63.6 | 64.4 |
| PC 18:0/22:6/supersensitive C-reactive protein | | −28.8 | 0.65 | 62.8 | 65.8 |

TABLE 4

Significant markers for CVD patients not undergoing statin treatment and not suffering from diabetes. Lipid names, p-values, % change, AUC, Sensitivity and Specificity values are presented. Table 4a shows significant lipid markers, Table 4b shows lipid-lipid concentration ratio markers and Table 4c shows lipid-clinical concentration ratio markers.

| Measurement name | P-value | Percentage change | AUC | Sensitivity | Specificity |
|---|---|---|---|---|---|
| *4a) Significant lipid markers for CVD patients not undergoing statin treatment and not suffering from diabetes.* | | | | | |
| *Increased* | | | | | |
| CE 19:1 (oxCE 682.6) | | 27.7 | 0.65 | 70.5 | 66.7 |
| GlcCer(d18:1/16:0) | 0.02176 | 22.7 | | | |
| SM (d18:1/18:1) | | 14.2 | 0.59 | 63.0 | 60.0 |
| *Decreased* | | | | | |
| PC 18:0/22:6 | 0.00685 | −20.3 | 0.67 | 74.4 | 61.5 |
| SM (d18:1/23:1) (d18:1/22:2-OH) | 0.01808 | −22.1 | 0.64 | 60.0 | 61.0 |
| *4b) Significant lipid - lipid concentration ratio markers for CVD patients not undergoing statin treatment and not suffering from diabetes.* | | | | | |
| *Increased* | | | | | |
| Cer(d18:1/18:0)/SM (d18:1/23:1) (d18:1/22:2-OH) | 0.00331 | 81.9 | 0.70 | 68.8 | 63.4 |
| Cer(d18:1/16:0)/PC 18:0/22:6 | 0.00045 | 78.7 | 0.74 | 76.7 | 61.5 |
| Cer(d18:1/18:0)/PC 16:0/22:6 | 0.00259 | 74.5 | 0.71 | 67.3 | 67.4 |
| GlcCer(d18:1/16:0)/PC 18:0/22:6 | 0.00101 | 69.7 | 0.73 | 74.4 | 61.5 |
| GlcCer(d18:1/18:0)/SM (d18:1/23:1) (d18:1/22:2-OH) | 0.00462 | 68.5 | 0.75 | 76.1 | 65.9 |
| Cer(d18:1/16:0)/PC 16:0/22:6 | 0.00024 | 62.1 | 0.72 | 75.9 | 60.9 |
| Cer(d18:1/20:0)/SM (d18:1/23:1) (d18:1/22:2-OH) | 0.00573 | 62.0 | 0.71 | 67.4 | 61.0 |
| GlcCer(d18:1/18:0)/PC 16:0/22:6 | 0.00006 | 60.4 | 0.76 | 80.0 | 60.9 |
| SM (d18:1/18:1)/SM (d18:1/23:1) (d18:1/22:2-OH) | | 60.2 | 0.76 | 81.6 | 63.4 |
| Cer(d18:1/20:0)/PC 16:0/22:6 | 0.00017 | 59.5 | 0.73 | 74.0 | 63.0 |
| SM (d18:1/16:0) (d18:1/15:1-OH)/SM (d18:1/23:1) (d18:1/22:2-OH) | | 57.1 | 0.73 | 74.0 | 63.4 |
| SM (d18:1/15:0) (d18:1/14:1-OH)/SM (d18:1/23:1) (d18:1/22:2-OH) | | 55.1 | 0.73 | 78.0 | 63.4 |
| GlcCer(d18:1/20:0)/SM (d18:1/23:1) (d18:1/22:2-OH) | | 54.9 | 0.71 | 78.3 | 61.0 |

TABLE 4-continued

Significant markers for CVD patients not undergoing statin treatment and not suffering from diabetes. Lipid names, p-values, % change, AUC, Sensitivity and Specificity values are presented. Table 4a shows significant lipid markers, Table 4b shows lipid-lipid concentration ratio markers and Table 4c shows lipid-clinical concentration ratio markers.

| Measurement name | P-value | Percentage change | AUC | Sensitivity | Specificity |
|---|---|---|---|---|---|
| Cer(d18:1/24:1)/PC 18:0/22:6 | | 53.8 | 0.70 | 72.1 | 69.2 |
| SM (d18:1/16:1) (d18:1/15:2-OH)/SM (d18:1/23:1) (d18:1/22:2-OH) | | 52.9 | 0.75 | 82.0 | 61.0 |
| GlcCer(d18:1/16:0)/PC 16:0/22:6 | 0.00081 | 52.6 | 0.72 | 75.9 | 60.9 |
| LacCer(d18:1/22:0)/PC 16:0/22:6 | 0.00047 | 52.4 | 0.73 | 68.0 | 60.9 |
| LacCer(d18:1/22:0)/SM (d18:1/23:1) (d18:1/22:2-OH) | | 49.3 | 0.71 | 71.7 | 61.0 |
| GlcCer(d18:1/20:0)/PC 16:0/22:6 | 0.00042 | 48.1 | 0.74 | 76.0 | 60.9 |
| CE 16:0/PC 18:0/22:6 | 0.00008 | 47.2 | 0.76 | 81.4 | 64.1 |
| Cer(d18:1/22:0)/PC 18:0/22:6 | | 44.3 | 0.71 | 74.4 | 61.5 |
| CE 18:2/PC 18:0/22:6 | 0.00025 | 43.5 | 0.75 | 67.4 | 64.1 |
| CE 18:1/PC 18:0/22:6 | 0.00106 | 42.6 | 0.73 | 79.1 | 61.5 |
| Cer(d18:1/16:0)/Cer(d18:1/24:0) | 0.00011 | 42.0 | 0.75 | 81.8 | 60.9 |
| Gb3(d18:1/16:0)/PC 16:0/22:6 | 0.00039 | 39.4 | 0.70 | 71.7 | 60.9 |
| CE 20:4/PC 18:0/22:6 | 0.00053 | 38.1 | 0.70 | 62.8 | 61.5 |
| CE 22:6/PC 18:0/22:6 | 0.00047 | 37.2 | 0.73 | 73.8 | 65.8 |
| PC 16:0/16:0/PC 16:0/22:6 | 0.00058 | 35.4 | | | |
| CE 16:0/PC 16:0/22:6 | 0.00023 | 33.8 | 0.71 | 68.5 | 63.0 |
| CE 18:2/PC 16:0/22:6 | 0.00057 | 33.7 | | | |
| Gb3(d18:1/24:0)/PC 16:0/22:6 | 0.00149 | 33.5 | 0.71 | 73.5 | 60.0 |
| CE 18:1/PC 16:0/22:6 | 0.00081 | 31.5 | 0.70 | 72.2 | 63.0 |
| CE 20:4/PC 16:0/22:6 | 0.00059 | 30.7 | | | |
| SM (d18:1/16:1) (d18:1/15:2-OH)/SM (d18:1/24:0) (d18:1/23:1-OH) | | 26.2 | 0.72 | 74.1 | 62.2 |
| Cer(d18:1/16:0)/Cer(d18:1/22:0) | 0.00048 | 26.0 | 0.71 | 67.3 | 65.2 |
| CE 16:0/Cer(d18:1/24:0) | 0.00089 | 22.9 | | | |
| SM (d18:1/18:1)/SM (d18:1/24:0) (d18:1/23:1-OH) | | 21.5 | 0.72 | 77.4 | 60.0 |
| GlcCer(d18:1/18:0)/SM (d18:1/24:0) (d18:1/23:1-OH) | | 21.3 | 0.72 | 70.0 | 62.2 |
| SM (d18:1/15:0) (d18:1/14:1-OH)/SM (d18:1/24:0) (d18:1/23:1-OH) | | 17.9 | 0.71 | 73.6 | 62.2 |
| Decreased | | | | | |
| Cer(d18:1/24:0)/GlcCer(d18:1/18:0) | 0.00035 | −22.3 | 0.70 | 60.8 | 65.2 |
| Cer(d18:1/24:0)/GlcCer(d18:1/16:0) | 0.00024 | −23.8 | 0.70 | 67.3 | 60.9 |
| PC 16:0/22:6/SM (d18:1/16:0) (d18:1/15:1-OH) | 0.00123 | −24.4 | 0.72 | 75.9 | 60.0 |
| PC 18:0/22:6/SM (d18:1/14:0) (d18:1/13:1-OH) | 0.00307 | −26.4 | 0.71 | 74.4 | 60.5 |
| PC 16:0/22:6/SM (d18:1/16:1) (d18:1/15:2-OH) | 0.00031 | −27.3 | 0.73 | 77.8 | 62.2 |
| PC 18:0/22:6/SM (d18:1/16:0) (d18:1/15:1-OH) | 0.00161 | −28.1 | 0.75 | 74.4 | 71.1 |
| PC 18:0/22:6/SM (d18:1/15:0) (d18:1/14:1-OH) | 0.00727 | −28.7 | 0.73 | 76.2 | 60.5 |
| PC 18:0/22:6/SM (d18:1/18:0) | 0.00565 | −28.9 | 0.72 | 69.8 | 64.9 |
| PC 18:0/22:6/SM (d18:1/16:1) (d18:1/15:2-OH) | 0.00018 | −33.3 | 0.78 | 81.4 | 60.5 |
| PC 18:0/22:6/SM (d18:1/18:1) | 0.00074 | −34.5 | 0.76 | 83.7 | 65.8 |
| 4c) Significant lipid-clinical concentration ratio markers for CVD patients not undergoing statin treatment and not suffering from diabetes. | | | | | |
| Increased | | | | | |
| Cer(d18:1/16:0)/HDL cholesterol | 0.00649 | 39.2 | 0.69 | 70.9 | 63.0 |
| GlcCer(d18:1/16:0)/apolipoprotein A-I | 0.01107 | 32.2 | | | |
| CE 19:1 oxCE 682.6/apolipoprotein A-I | | 32.0 | 0.66 | 63.6 | 66.7 |
| GlcCer(d18:1/18:0)/apolipoprotein A-I | 0.00289 | 31.9 | 0.69 | 72.5 | 60.9 |
| GlcCer(d18:1/18:0)/HDL cholesterol | 0.00816 | 31.2 | 0.68 | 70.6 | 60.9 |
| GlcCer(d18:1/16:0)/HDL cholesterol | 0.01982 | 31.1 | | | |
| GlcCer(d18:1/20:0)/apolipoprotein A-I | 0.01983 | 21.5 | 0.66 | 68.6 | 60.9 |
| GlcCer(d18:1/18:0)/total cholesterol | 0.00787 | 21.5 | 0.65 | 68.6 | 60.9 |
| Cer(d18:1/16:0)/apolipoprotein B | 0.01020 | 20.3 | 0.66 | 61.8 | 60.9 |
| Decreased | | | | | |
| LacCer(d18:1/24:0)/supersensitive C-reactive protein | | −9.1 | 0.65 | 64.6 | 60.0 |
| CE 17:1/supersensitive C-reactive protein | | −12.3 | 0.64 | 61.5 | 61.9 |
| SM (d18:1/16:0) (d18:1/15:1-OH)/supersensitive C-reactive protein | | −13.0 | 0.64 | 60.0 | 61.4 |
| GlcCer(d18:1/24:0)/supersensitive C-reactive protein | | −13.1 | 0.64 | 65.5 | 60.0 |
| Gb3(d18:1/22:0)/supersensitive C-reactive protein | | −14.0 | 0.64 | 60.0 | 68.2 |
| PC 18:0/20:3/apolipoprotein B | 0.01774 | −16.0 | | | |
| PC 16:0/16:1/supersensitive C-reactive protein | | −16.2 | 0.64 | 63.0 | 63.4 |
| PC 16:0/22:6/total cholesterol | 0.00719 | −16.5 | | | |
| PC 16:0/22:6/apolipoprotein B | 0.00559 | −19.0 | | | |
| PC 18:1/18:1/supersensitive C-reactive protein | | −19.0 | 0.64 | 61.8 | 60.5 |
| SM (d18:1/24:1) (d18:1/23:2-OH)/supersensitive C-reactive protein | | −19.2 | 0.66 | 65.5 | 65.9 |
| PC 18:0/18:2/supersensitive C-reactive protein | | −20.4 | 0.64 | 61.8 | 64.4 |
| Cer(d18:1/24:1)/supersensitive C-reactive protein | | −20.5 | 0.64 | 60.0 | 62.2 |
| Cer(d18:1/22:0)/supersensitive C-reactive protein | | −21.0 | 0.64 | 61.8 | 68.9 |

TABLE 4-continued

Significant markers for CVD patients not undergoing statin treatment and not suffering from diabetes. Lipid names, p-values, % change, AUC, Sensitivity and Specificity values are presented. Table 4a shows significant lipid markers, Table 4b shows lipid-lipid concentration ratio markers and Table 4c shows lipid-clinical concentration ratio markers.

| Measurement name | P-value | Percentage change | AUC | Sensitivity | Specificity |
| --- | --- | --- | --- | --- | --- |
| PC 18:0/22:6/triglycerides | | −21.4 | 0.67 | 60.5 | 64.1 |
| SM (d18:1/18:0)/supersensitive C-reactive protein | | −22.3 | 0.64 | 63.6 | 60.5 |
| PC 18:0/20:3/supersensitive C-reactive protein | | −22.4 | 0.65 | 66.7 | 60.0 |
| SM (d18:1/24:0) (d18:1/23:1-OH)/supersensitive C-reactive protein | | −22.8 | 0.65 | 63.0 | 61.4 |
| PC 16:0/18:1/supersensitive C-reactive protein | | −22.9 | 0.64 | 61.8 | 62.2 |
| SM (d18:1/23:1) (d18:1/22:2-OH)/total cholesterol | 0.01384 | −23.0 | | | |
| PC 18:0/22:6/LDL cholesterol | 0.00466 | −23.1 | 0.73 | 76.7 | 61.5 |
| PC 18:0/22:6/total cholesterol | 0.00079 | −23.2 | 0.73 | 81.4 | 64.1 |
| SM (d18:1/23:1) (d18:1/22:2-OH)/LDL cholesterol | 0.01112 | −23.8 | | | |
| SM (d18:1/23:1) (d18:1/22:2-OH)/apolipoprotein B | 0.01067 | −24.9 | 0.64 | 60.0 | 61.0 |
| PC 18:0/22:6/apolipoprotein B | 0.00065 | −25.2 | 0.74 | 81.4 | 64.1 |
| SM (d18:1/23:0) (d18:1/22:1-OH)/supersensitive C-reactive protein | | −27.0 | 0.65 | 63.0 | 61.4 |
| PC 18:0/18:1/supersensitive C-reactive protein | | −27.2 | 0.64 | 63.0 | 60.0 |
| LPC 16:0/supersensitive C-reactive protein | | −27.7 | 0.65 | 63.6 | 62.2 |
| PC 16:0/22:6/supersensitive C-reactive protein | | −30.9 | 0.66 | 63.0 | 64.4 |
| SM (d18:1/23:1) (d18:1/22:2-OH)/supersensitive C-reactive protein | | −34.8 | 0.69 | 72.0 | 60.0 |
| PC 18:0/22:6/lipoprotein(a) | | −46.6 | 0.66 | 63.9 | 71.4 |
| PC 16:0/18:0/supersensitive C-reactive protein | 0.03865 | −47.5 | 0.65 | 62.8 | 61.8 |

TABLE 5

Significant markers for CVD patients not undergoing statin treatment and having diabetes. Marker names, p-values, percentage change, AUC, Specificity and Sensitivity are presented. Table 5a shows significant lipid markers, Table 5b shows significant lipid-lipid concentration ratio markers and Table 5c shows significant lipid-clinical concentration ratio markers.

| Measurement name | P-value | Percentage change | AUC | Sensitivity | Specificity |
| --- | --- | --- | --- | --- | --- |
| 5a) Significant lipid markers for CVD patients not undergoing statin treatment and having diabetes. | | | | | |
| Increased | | | | | |
| Gb3(d18:1/24:1) | 0.02669 | 25.9 | | | |
| Gb3(d18:1/16:0) | 0.01318 | 17.6 | | | |
| Decreased | | | | | |
| PC O-16:0/20:4-alkyl | | −13.7 | 0.58 | 61.5 | 60.0 |
| CE 20:4 | 0.02179 | −14.0 | 0.61 | 64.2 | 60.0 |
| CE 18:0 | 0.00754 | −18.0 | | | |
| 5b) Significant lipid-lipid concentration ratio markers for CVD patients not undergoing statin treatment and having diabetes. | | | | | |
| Increased | | | | | |
| Gb3(d18:1/24:1)/SM (d18:1/17:0) (d18:1/16:1-OH) | 0.00674 | 44.5 | 0.69 | 69.2 | 60.5 |
| Gb3(d18:1/24:1)/PC O-16:0/20:4-alkyl | 0.00606 | 33.8 | 0.68 | 69.2 | 60.0 |
| Gb3(d18:1/16:0)/SM (d18:1/17:0) (d18:1/16:1-OH) | 0.03447 | 32.6 | 0.66 | 63.5 | 62.8 |
| Gb3(d18:1/24:1)/GlcCer(d18:1/24:0) | 0.00369 | 31.5 | 0.67 | 75.0 | 62.0 |
| Gb3(d18:1/24:1)/GlcCer(d18:1/22:0) | 0.00635 | 27.8 | 0.66 | 63.2 | 62.0 |
| Gb3(d18:1/22:0)/SM (d18:1/17:0) (d18:1/16:1-OH) | | 26.4 | 0.67 | 68.6 | 61.9 |
| Decreased | | | | | |
| CE 18:0/PC 18:0/18:2 | | −12.0 | 0.67 | 64.1 | 65.2 |
| PC 18:0/18:2/PE 18:0/18:2 | | −13.0 | 0.67 | 70.7 | 61.5 |
| Cer(d18:1/24:0)/PE 18:0/18:2 | | −13.8 | 0.65 | 65.5 | 61.5 |
| CE 18:0/CE 18:1 | 0.00266 | −15.6 | | | |
| CE 18:2/Gb3(d18:1/16:0) | 0.00336 | −16.2 | 0.66 | 74.6 | 62.0 |
| CE 16:0/Gb3(d18:1/16:0) | 0.00265 | −16.4 | 0.66 | 64.2 | 60.0 |
| CE 18:0/PC 16:0/22:6 | | −17.5 | 0.68 | 70.3 | 60.0 |
| CE 14:0/Gb3(d18:1/24:0) | | −18.9 | 0.66 | 67.7 | 61.2 |
| CE 18:0/SM (d18:1/16:0) (d18:1/15:1-OH) | 0.00313 | −19.1 | | | |
| CE 18:3/SM (d18:1/14:0) (d18:1/13:1-OH) | 0.00287 | −19.3 | 0.66 | 67.2 | 60.0 |
| CE 18:0/PC 16:0/18:2 | 0.00185 | −19.6 | 0.69 | 62.5 | 65.2 |
| Cer(d18:1/24:0)/PC O-16:0/18:1-alkyl | 0.00226 | −19.8 | 0.67 | 66.0 | 61.5 |
| CE 18:0/Gb3(d18:1/24:0) | | −20.6 | 0.66 | 61.7 | 60.0 |
| CE 18:3/PC 16:0/18:1 | 0.00081 | −20.8 | 0.69 | 73.1 | 62.0 |
| PC 18:0/20:3/PC O-16:0/18:1-alkyl | 0.00849 | −20.9 | 0.69 | 73.6 | 61.5 |

TABLE 5-continued

Significant markers for CVD patients not undergoing statin treatment and having diabetes. Marker names, p-values, percentage change, AUC, Specificity and Sensitivity are presented. Table 5a shows significant lipid markers, Table 5b shows significant lipid-lipid concentration ratio markers and Table 5c shows significant lipid-clinical concentration ratio markers.

| Measurement name | P-value | Percentage change | AUC | Sensitivity | Specificity |
|---|---|---|---|---|---|
| CE 14:0/PC 16:0/16:0 | 0.00266 | −20.9 | 0.65 | 65.2 | 63.3 |
| CE 17:1/Gb3(d18:1/16:0) | 0.00301 | −21.1 | 0.66 | 68.3 | 60.9 |
| CE 14:0/SM (d18:1/14:0) (d18:1/13:1-OH) | 0.00090 | −21.4 | | | |
| PC 18:0/20:3/PE 18:0/18:2 | 0.00794 | −21.5 | 0.70 | 65.5 | 71.8 |
| CE 18:0/SM (d18:1/14:0) (d18:1/13:1-OH) | 0.00120 | −21.6 | 0.70 | 75.0 | 60.9 |
| CE 14:0/PC 16:0/18:1 | 0.00110 | −21.8 | 0.66 | 68.2 | 60.0 |
| CE 18:0/SM (d18:1/24:1) (d18:1/23:2-OH) | | −21.9 | 0.66 | 62.5 | 60.9 |
| CE 18:0/Cer(d18:1/16:0) | 0.00203 | −22.5 | 0.65 | 60.9 | 60.9 |
| CE 18:0/Cer(d18:1/24:1) | 0.00347 | −22.9 | 0.68 | 68.8 | 63.0 |
| CE 18:0/PC 16:0/16:0 | 0.00085 | −23.4 | 0.66 | 62.5 | 62.2 |
| CE 18:0/PC 18:1/18:1 | 0.00151 | −23.7 | 0.67 | 63.5 | 61.4 |
| CE 18:0/PC 16:0/18:1 | 0.00032 | −24.1 | 0.69 | 67.2 | 60.9 |
| CE 20:4/PC O-16:0/18:1-alkyl | 0.00261 | −24.1 | | | |
| CE 18:3/PE 18:0/18:2 | 0.00810 | −24.2 | 0.68 | 63.2 | 66.7 |
| CE 20:4/Gb3(d18:1/16:0) | 0.00070 | −24.4 | 0.66 | 61.2 | 66.0 |
| CE 14:0/PE 18:0/18:2 | 0.00735 | −24.9 | 0.68 | 75.0 | 61.5 |
| CE 18:0/Cer(d18:1/26:1) | 0.00471 | −25.0 | 0.66 | 62.3 | 68.4 |
| CE 18:3/Gb3(d18:1/22:0) | 0.00487 | −25.4 | 0.66 | 61.5 | 61.2 |
| CE 14:0/Gb3(d18:1/16:0) | 0.00189 | −25.4 | 0.67 | 68.2 | 60.0 |
| CE 18:3/PC O-16:0/18:1-alkyl | 0.00038 | −25.7 | 0.70 | 75.0 | 66.7 |
| CE 18:3/Gb3(d18:1/16:0) | 0.00180 | −26.0 | 0.66 | 70.1 | 62.0 |
| CE 14:0/PC O-16:0/18:1-alkyl | 0.00041 | −26.5 | 0.70 | 72.5 | 64.1 |
| CE 20:4/Gb3(d18:1/18:0) | 0.00233 | −26.6 | 0.66 | 68.3 | 61.7 |
| CE 18:3/Gb3(d18:1/24:1) | 0.00624 | −27.3 | 0.67 | 68.7 | 60.0 |
| CE 14:0/Gb3(d18:1/24:1) | 0.00652 | −27.6 | 0.68 | 65.2 | 60.0 |
| CE 20:5/PC O-16:0/18:1-alkyl | | −28.0 | 0.67 | 68.6 | 64.1 |
| CE 18:0/Gb3(d18:1/18:0) | 0.00246 | −28.2 | 0.66 | 61.4 | 60.5 |
| CE 18:0/Gb3(d18:1/16:0) | 0.00056 | −28.4 | 0.68 | 64.1 | 63.0 |
| CE 18:0/Gb3(d18:1/24:1) | | −34.6 | 0.69 | 67.2 | 60.9 |

5c) Significant lipid-clinical concentration ratio markers for CVD patients not undergoing statin treatment and having diabetes.

Increased

| Measurement name | P-value | Percentage change | AUC | Sensitivity | Specificity |
|---|---|---|---|---|---|
| PC 18:1/18:1/lipoprotein(a) | | 381.2 | 0.67 | 62.3 | 61.7 |
| PC O-16:0/18:1-alkyl/lipoprotein(a) | | 221.1 | 0.68 | 70.2 | 63.2 |
| Gb3(d18:1/18:0)/lipoprotein(a) | 0.01723 | 180.6 | 0.67 | 60.0 | 65.2 |
| SM (d18:1/23:1) (d18:1/22:2-OH)/lipoprotein(a) | 0.01616 | 179.1 | 0.67 | 63.8 | 60.0 |
| Gb3(d18:1/24:1)/lipoprotein(a) | 0.01496 | 176.8 | | | |
| Gb3(d18:1/16:0)/lipoprotein(a) | 0.03006 | 174.6 | 0.67 | 64.5 | 61.2 |
| PE 18:0/18:2/lipoprotein(a) | 0.01545 | 173.2 | | | |
| LacCer(d18:1/24:1)/lipoprotein(a) | | 164.4 | 0.65 | 62.9 | 64.6 |
| LacCer(d18:1/22:0)/lipoprotein(a) | | 158.5 | 0.64 | 62.9 | 61.2 |
| Gb3(d18:1/22:0)/lipoprotein(a) | 0.01598 | 148.3 | | | |
| CE 17:1/lipoprotein(a) | 0.04319 | 148.1 | 0.64 | 64.9 | 60.0 |
| Gb3(d18:1/24:0)/lipoprotein(a) | 0.04567 | 131.6 | 0.67 | 63.8 | 62.5 |
| PC 16:0/18:2/lipoprotein(a) | 0.01114 | 128.9 | | | |
| PC O-18:0/18:2-alkyl/lipoprotein(a) | 0.04267 | 125.5 | 0.65 | 61.8 | 60.0 |
| LacCer(d18:1/24:0)/lipoprotein(a) | | 117.2 | 0.64 | 60.3 | 60.5 |
| PC 17:0/18:2/lipoprotein(a) | | 116.6 | 0.65 | 66.1 | 60.5 |
| SM (d18:1/18:0)/lipoprotein(a) | 0.01151 | 108.7 | | | |
| CE 15:0/lipoprotein(a) | 0.03255 | 98.1 | 0.64 | 64.3 | 61.4 |
| PC O-16:0/18:2-alkyl/lipoprotein(a) | | 70.4 | 0.65 | 67.3 | 61.0 |
| Gb3(d18:1/24:1)/LDL cholesterol | 0.00201 | 43.8 | | | |
| Gb3(d18:1/24:1)/apolipoprotein B | 0.00406 | 37.8 | | | |
| Gb3(d18:1/24:1)/total cholesterol | 0.00279 | 35.6 | | | |
| Gb3(d18:1/24:1)/apolipoprotein A-I | 0.00640 | 35.3 | | | |
| PC O-16:0/18:1-alkyl/LDL cholesterol | 0.01994 | 34.1 | 0.66 | 60.4 | 64.1 |
| Gb3(d18:1/16:0)/LDL cholesterol | 0.00024 | 33.2 | 0.69 | 64.7 | 60.0 |
| Gb3(d18:1/24:1)/HDL cholesterol | 0.01160 | 32.0 | | | |
| Gb3(d18:1/22:0)/LDL cholesterol | 0.00367 | 31.2 | | | |
| Gb3(d18:1/18:0)/LDL cholesterol | 0.00054 | 30.3 | | | |
| Gb3(d18:1/24:0)/LDL cholesterol | 0.01420 | 29.8 | | | |
| Gb3(d18:1/16:0)/apolipoprotein B | 0.00125 | 27.4 | 0.67 | 67.6 | 60.0 |
| PC O-16:0/18:1-alkyl/apolipoprotein B | 0.00725 | 26.5 | | | |
| PC O-16:0/18:1-alkyl/triglycerides | | 26.3 | 0.61 | 62.3 | 61.5 |
| Gb3(d18:1/16:0)/total cholesterol | 0.00060 | 25.5 | 0.68 | 66.2 | 62.0 |
| Gb3(d18:1/22:0)/apolipoprotein B | 0.01357 | 25.3 | | | |
| PC 16:0/16:0/LDL cholesterol | 0.01619 | 25.0 | | | |
| Gb3(d18:1/18:0)/apolipoprotein B | 0.00545 | 24.6 | | | |
| PC O-16:0/18:1-alkyl/total cholesterol | 0.00448 | 24.1 | | | |
| SM (d18:1/24:1) (d18:1/23:2-OH)/LDL cholesterol | 0.04799 | 24.0 | 0.62 | 62.7 | 62.0 |
| Gb3(d18:1/16:0)/triglycerides | | 23.8 | 0.60 | 64.7 | 60.0 |

TABLE 5-continued

Significant markers for CVD patients not undergoing statin treatment and having diabetes. Marker names, p-values, percentage change, AUC, Specificity and Sensitivity are presented. Table 5a shows significant lipid markers, Table 5b shows significant lipid-lipid concentration ratio markers and Table 5c shows significant lipid-clinical concentration ratio markers.

| Measurement name | P-value | Percentage change | AUC | Sensitivity | Specificity |
|---|---|---|---|---|---|
| PE 18:0/18:2/LDL cholesterol | | 23.4 | 0.62 | 65.5 | 61.5 |
| Gb3(d18:1/22:0)/total cholesterol | 0.01269 | 22.9 | | | |
| PE 18:0/18:2/triglycerides | | 21.6 | 0.63 | 67.2 | 61.5 |
| Gb3(d18:1/18:0)/total cholesterol | 0.01020 | 21.4 | | | |
| PE 18:0/18:2/total cholesterol | 0.01992 | 19.2 | 0.64 | 62.1 | 61.5 |
| PC 16:0/18:2/LDL cholesterol | | 17.9 | 0.60 | 61.8 | 64.0 |
| PC 16:0/16:0/total cholesterol | 0.01555 | 17.5 | | | |
| PE 18:0/18:2/apolipoprotein B | | 15.0 | 0.64 | 65.5 | 61.5 |
| SM (d18:1/14:0) (d18:1/13:1-OH)/total cholesterol | 0.04182 | 11.0 | 0.62 | 61.2 | 60.0 |
| Decreased | | | | | |
| CE 14:0/HDL cholesterol | | −13.1 | 0.61 | 63.6 | 62.0 |
| CE 14:0/supersensitive C-reactive protein | | −36.8 | 0.62 | 60.6 | 60.0 |

TABLE 6

The preferred embodiment markers from CVD patients not undergoing statin treatment and not having diabetes.

| Measurement name | P-value | Percentage change | AUC | Sensitivity | Specificity |
|---|---|---|---|---|---|
| Lipids Increased | | | | | |
| CE 19:1 oxCE 682.6 | | 27.7 | 0.65 | 70.5 | 66.7 |
| GlcCer(d18:1/16:0) | 0.02176 | 22.7 | | | |
| SM (d18:1/18:1) | | 14.2 | 0.59 | 63.0 | 60.0 |
| Decreased | | | | | |
| PC 18:0/22:6 | 0.00685 | −20.3 | 0.67 | 74.4 | 61.5 |
| SM (d18:1/23:1) (d18:1/22:2-OH) | 0.01808 | −22.1 | 0.64 | 60.0 | 61.0 |
| Lipid-lipid concentration ratios Increased | | | | | |
| Cer(d18:1/18:0)/SM (d18:1/23:1) (d18:1/22:2-OH) | 0.00331 | 81.9 | 0.70 | 68.8 | 63.4 |
| Cer(d18:1/16:0)/PC 18:0/22:6 | 0.00045 | 78.7 | 0.74 | 76.7 | 61.5 |
| Cer(d18:1/18:0)/PC 16:0/22:6 | 0.00259 | 74.5 | 0.71 | 67.3 | 67.4 |
| GlcCer(d18:1/16:0)/PC 18:0/22:6 | 0.00101 | 69.7 | 0.73 | 74.4 | 61.5 |
| GlcCer(d18:1/18:0)/SM (d18:1/23:1) (d18:1/22:2-OH) | 0.00462 | 68.5 | 0.75 | 76.1 | 65.9 |
| Cer(d18:1/16:0)/PC 16:0/22:6 | 0.00024 | 62.1 | 0.72 | 75.9 | 60.9 |
| Cer(d18:1/20:0)/SM (d18:1/23:1) (d18:1/22:2-OH) | 0.00573 | 62.0 | 0.71 | 67.4 | 61.0 |
| GlcCer(d18:1/18:0)/PC 16:0/22:6 | 0.00006 | 60.4 | 0.76 | 80.0 | 60.9 |
| SM (d18:1/18:1)/SM (d18:1/23:1) (d18:1/22:2-OH) | | 60.2 | 0.76 | 81.6 | 63.4 |
| Cer(d18:1/20:0)/PC 16:0/22:6 | 0.00017 | 59.5 | 0.73 | 74.0 | 63.0 |
| SM (d18:1/16:0) (d18:1/15:1-OH)/SM (d18:1/23:1) (d18:1/22:2-OH) | | 57.1 | 0.73 | 74.0 | 63.4 |
| SM (d18:1/15:0) (d18:1/14:1-OH)/SM (d18:1/23:1) (d18:1/22:2-OH) | | 55.1 | 0.73 | 78.0 | 63.4 |
| GlcCer(d18:1/20:0)/SM (d18:1/23:1) (d18:1/22:2-OH) | | 54.9 | 0.71 | 78.3 | 61.0 |
| Cer(d18:1/24:1)/PC 18:0/22:6 | | 53.8 | 0.70 | 72.1 | 69.2 |
| SM (d18:1/16:1) (d18:1/15:2-OH)/SM (d18:1/23:1) (d18:1/22:2-OH) | | 52.9 | 0.75 | 82.0 | 61.0 |
| GlcCer(d18:1/16:0)/PC 16:0/22:6 | 0.00081 | 52.6 | 0.72 | 75.9 | 60.9 |
| LacCer(d18:1/22:0)/PC 16:0/22:6 | 0.00047 | 52.4 | 0.73 | 68.0 | 60.9 |
| CE 16:0/PC 18:0/22:6 | 0.00008 | 47.2 | 0.76 | 81.4 | 64.1 |
| CE 18:2/PC 18:0/22:6 | 0.00025 | 43.5 | 0.75 | 67.4 | 64.1 |
| Cer(d18:1/16:0)/Cer(d18:1/24:0) | | 42.0 | 0.75 | 81.8 | 60.9 |
| Decreased | | | | | |
| PC 18:0/22:6/SM (d18:1/16:1) (d18:1/15:2-OH) | 0.00018 | −33.3 | 0.78 | 81.4 | 60.5 |
| PC 18:0/22:6/SM (d18:1/18:1) | 0.00074 | −34.5 | 0.76 | 83.7 | 65.8 |
| Lipid-clinical concentration ratios Increased | | | | | |
| Cer(d18:1/16:0)/HDL cholesterol | 0.00649 | 39.2 | 0.69 | 70.9 | 63.0 |

TABLE 6-continued

The preferred embodiment markers from CVD patients not undergoing statin treatment and not having diabetes.

| Measurement name | P-value | Percentage change | AUC | Sensitivity | Specificity |
|---|---|---|---|---|---|
| Decreased | | | | | |
| PC 18:0/22:6/LDL cholesterol | 0.00466 | −23.1 | 0.73 | 76.7 | 61.5 |
| PC 18:0/22:6/total cholesterol | 0.00079 | −23.2 | 0.73 | 81.4 | 64.1 |
| PC 18:0/22:6/apolipoprotein B | 0.00065 | −25.2 | 0.74 | 81.4 | 64.1 |

TABLE 7

The preferred embodiment markers from CVD patients not undergoing statin treatment and having diabetes.

| Measurement name | P-value | Percentage change | AUC | Sensitivity | Specificity |
|---|---|---|---|---|---|
| Lipids Increased | | | | | |
| Gb3(d18:1/24:1) | 0.02669 | 25.9 | | | |
| Gb3(d18:1/16:0) | 0.01318 | 17.6 | | | |
| Decreased | | | | | |
| PC O-16:0/20:4-alkyl | | −13.7 | 0.58 | 61.5 | 60.0 |
| CE 20:4 | 0.02179 | −14.0 | 0.61 | 64.2 | 60.0 |
| CE 18:0 | 0.00754 | −18.0 | | | |
| Lipid-lipid concentration ratios Increased | | | | | |
| Gb3(d18:1/24:1)/SM (d18:1/17:0) (d18:1/16:1-OH) | 0.00674 | 44.5 | 0.69 | 69.2 | 60.5 |
| Gb3(d18:1/16:0)/SM (d18:1/17:0) (d18:1/16:1-OH) | 0.03447 | 32.6 | 0.66 | 63.5 | 62.8 |
| Gb3(d18:1/24:1)/GlcCer(d18:1/24:0) | 0.00369 | 31.5 | 0.67 | 75.0 | 62.0 |
| Decreased | | | | | |
| CE 18:3/PC 16:0/18:1 | 0.00081 | −20.8 | 0.69 | 73.1 | 62.0 |
| CE 18:0/SM (d18:1/14:0) (d18:1/13:1-OH) | 0.00120 | −21.6 | 0.70 | 75.0 | 60.9 |
| CE 14:0/PE 18:0/18:2 | 0.00735 | −24.9 | 0.68 | 75.0 | 61.5 |
| CE 18:3/PC O-16:0/18:1-alkyl | 0.00038 | −25.7 | 0.70 | 75.0 | 66.7 |
| CE 18:0/Gb3(d18:1/16:0) | 0.00056 | −28.4 | 0.68 | 64.1 | 63.0 |
| CE 18:0/Gb3(d18:1/24:1) | | −34.6 | 0.69 | 67.2 | 60.9 |
| Lipid-clinical concentration ratios Increased | | | | | |
| PC 18:1/18:1/lipoprotein(a) | | 381.2 | 0.67 | 62.3 | 61.7 |
| Gb3(d18:1/18:0)/lipoprotein(a) | 0.01723 | 180.6 | 0.67 | 60.0 | 65.2 |
| Gb3(d18:1/16:0)/lipoprotein(a) | 0.03006 | 174.6 | 0.67 | 64.5 | 61.2 |
| LacCer(d18:1/24:1)/lipoprotein(a) | | 164.4 | 0.65 | 62.9 | 64.6 |
| Decreased | | | | | |
| CE 14:0/supersensitive C-reactive protein | | −36.8 | 0.62 | 60.6 | 60.0 |

The preferred lipid molecules of the invention were selected as follows: a) it was likely to be biologically meaningful, b) it preferably belongs to a family of lipids that are behaving similarly, c) it is expressed in meaningful & measurable concentrations, d) it has very significant p-value or good AUC-value (>0.65) and for most also the %-change is substantial (>20%), and e) it appeared significant in different tests

TABLE 8

Lipid markers generated with logistic modeling.

| CVD high risk markers for CVD patients not on statin treatment and not having diabetes | | CVD high risk markers for CVD patients not on statin treatment and having diabetes | |
|---|---|---|---|
| Lipid | Direction of change | Lipid | Direction of change |
| GlcCer 18:1/16:0 | increased | Gb3 18:1/16:0 | increased |
| CE 20:4 | increased | GlcCer 18:1/16:0 | increased |
| LacCer(d18:1/16:0) | increased | LacCer 18:1/16:0 | increased |
| Cer 18:1/16:0 | increased | PC 16:0/22:6 | increased |
| CE 16:0 | increased | CE 14:0 | decreased |
| SM 18:1/16:0 | increased | CE 22:6 | decreased |

TABLE 8-continued

Lipid markers generated with logistic modeling.

| CVD high risk markers for CVD patients not on statin treatment and not having diabetes | | CVD high risk markers for CVD patients not on statin treatment and having diabetes | |
|---|---|---|---|
| Lipid | Direction of change | Lipid | Direction of change |
| LPC 16:0 | decreased | CE 18:3 | decreased |
| PC 16:0/22:6 | decreased | GlcCer 18:1/18:0 | decreased |
| SM 18:1/24:0 | decreased | SM 18:1/24:0 | decreased |

Lipidomic analysis proved to be efficient in identifying novel plasma biomarkers for CVD complications.

Molecular lipid to molecular lipid ratio could be an important indicator of cellular lipid metabolism including e.g., enzyme activities in the lipid metabolism pathways. Thus, these ratios may provide more information as the absolute plasma concentrations of the molecular lipids alone. As the absolute molecular lipid plasma concentration differences in general between healthy individuals and atherosclerotic patients seem to be between 30-70%, it might be reasonable to calculate and use different ratios instead of absolute concentrations only. As lipoprotein particles (e.g. LDL, HDL and VLDL) are serving as carriers for most of the lipids in the blood stream it is appropriate to relate molecular lipid concentrations to lipoprotein data. Thus, the molecular lipid to HDL-cholesterol, LDL-cholesterol, apolipoprotein A-I and apolipoprotein B ratios were calculated. In fact, a number of ratios between the concentrations of different molecular lipids outperformed absolute plasma concentrations as disease biomarkers in CVD patients.

As the detected lipids are carried in the lipoprotein particles (LDL, VLDL and HDL) it is obvious that the corresponding lipoprotein fraction concentrations will even improve the prediction potential of molecular lipids from the results of the present study in total serum/plasma samples.

The lipid lowering drug efficiency measurements have so far been based on LDL-C and HDL-C assays. As the inventors have herein observed more potential biomarkers that predict the development of high-risk CVD complications better than these classical analyses, future drug efficiency profiling should be based on new sensitive and specific biomarkers that are more directly related to the risk of severe CVD-related complications rather than to LDL-C.

Those skilled in the art will recognize, or be able to ascertain using no more than routine experimentation, numerous equivalents to the specific embodiments described herein both in the Examples in the body of the entire patent description. Such equivalents are considered to be within the scope of this invention and are covered by the following claims.

The invention claimed is:

1. A method for determining whether a subject not undergoing statin treatment who is not suffering from type 2 diabetes mellitus is at risk to develop one or more cardiovascular vascular disease (CVD) complications, comprising:
   a) determining in a sample from said subject one or more lipid-lipid concentration ratio(s), wherein (an) increased or decreased lipid-lipid concentration ratio(s) in said sample, when compared to a control sample is (are) indicative of said subject having an increased risk of developing one or more CVD complications,
   wherein the one or more lipid-lipid concentration ratio(s) whose increase(s) is (are) compared to the control is (are) selected from: Cer(d18:1/16:0)/PC 18:0/22:6, Cer(d18:1/16:0)/PC 16:0/22:6, Cer(d18:1/18:0)/PC 16:0/22:6, Cer(d18:1/24:1)/PC 18:0/22:6, Cer(d18:1/20:0)/PC 16:0/22:6, Cer(d18:1/22:0)/PC 18:0/22:6, CE 16:0/Cer(d18:1/24:0), Cer(d18:1/18:0)/SM (d18:1/23:1) (d18:1/22:2-OH) and Cer(d18:1/20:0)/SM (d18:1/23:1) (d18:1/22:2-OH); and
   wherein the one or more lipid-lipid concentration ratio(s) whose decrease(s) is (are) compared to the control is (are) selected from: Cer(d18:1/24:0)/GlcCer(d18:1/18:0) and Cer(d18:1/24:0)/GlcCer(d18:1/16:0); and/or
   b) determining in a sample from said subject one or more lipid-clinical concentration ratio(s), wherein (an) increased or decreased lipid-clinical concentration ratio(s) in said sample, when compared to a control sample is (are) indicative of said subject having an increased risk of developing one or more CVD complications,
   wherein the one or more lipid-clinical concentration ratio(s) whose increase(s) is (are) compared to the control is (are) selected from: Cer(d18:1/16:0)/HDL cholesterol and Cer(d18:1/16:0)/apolipoprotein B; and wherein the one or more lipid-clinical concentration ratio(s) whose decrease(s) is (are) compared to the control is (are) selected from: Cer(d18:1/24:1)/super-sensitive C-reactive protein and Cer(d18:1/22:0)/super-sensitive C-reactive protein.

2. A method for determining whether a subject not undergoing statin treatment who is suffering from type 2 diabetes mellitus is at risk to develop one or more cardiovascular vascular disease (CVD) complications, comprising:
   a) determining in a sample from said subject one or more lipid-lipid concentration ratio(s), wherein (a) decreased lipid-lipid concentration ratio(s) in said sample, when compared to a control sample, is (are) indicative of said subject having an increased risk of developing one or more CVD complications,
   wherein the one or more lipid-lipid concentration ratio(s) whose decrease(s) is (are) compared to the control is (are) selected from: Cer(d18:1/24:0)/PE 18:0/18:2, Cer(d18:1/24:0)/PC 0-16:0/18:1-alkyl, CE 18:0/Cer(d18:1/16:0), CE 18:0/Cer(d18:1/24:1) and CE 18:0/Cer(d18:1/26:1).

3. The method of claim 1, comprising determining at least 2 lipid-lipid concentration ratios or lipid-clinical concentration ratios, respectively, or combinations thereof.

4. The method of claim 2, comprising determining at least 2 lipid-lipid concentration ratios.

5. The method of claim 1, wherein
   a) said CVD complications is (are) coronary artery disease, peripheral artery disease, a stroke and/or CVD death; and/or
   b) said CVD is atherosclerosis-induced; and/or
   c) said subject has atherosclerosis; or
   d) said subject does not have atherosclerosis.

6. The method of claim 2, wherein
a) said CVD complications is (are) coronary artery disease, peripheral artery disease, a stroke and/or CVD death; and/or
b) said CVD is atherosclerosis-induced; and/or
c) said subject has atherosclerosis; or
d) said subject does not have atherosclerosis.

7. The method of claim 1, wherein
a) the method further comprises determining the serum or plasma level of total cholesterol, low-density lipoprotein cholesterol (LDL-C), high-density lipoprotein cholesterol (HDL-C), Apolipoprotein B (ApoB) and/or Apolipoprotein C-III (ApoC-III) in said sample; and/or
b) the subject does not have elevated serum or plasma levels of one or more of total cholesterol, low-density lipoprotein cholesterol (LDL-C), Apolipoprotein C-III (ApoC-III) or Apolipoprotein B (ApoB), or a decreased serum level of HDL-cholesterol (HDL-C).

8. The method of claim 2, wherein
a) the method further comprises determining the serum or plasma level of total cholesterol, low-density lipoprotein cholesterol (LDL-C), high-density lipoprotein cholesterol (HDL-C), Apolipoprotein B (ApoB) and/or Apolipoprotein C-III (ApoC-III) in said sample; and/or
b) the subject does not have elevated serum or plasma levels of one or more of total cholesterol, low-density lipoprotein cholesterol (LDL-C), Apolipoprotein C-III (ApoC-III) or Apolipoprotein B (ApoB), or a decreased serum level of HDL-cholesterol (HDL-C).

9. The method of claim 1, wherein
a) the sample is blood, plasma, serum, urine or tissue, or a lipoprotein fraction thereof; and/or
b) the lipid concentration, the lipid-lipid concentration ratio(s) or the lipid-clinical concentration ratio(s) is (are) determined by using mass spectrometry, nuclear magnetic resonance spectroscopy, fluorescence spectroscopy or dual polarization interferometry, a high performance separation method, an immunoassay and/or with a binding moiety capable of specifically binding the analyte.

10. The method of claim 2, wherein
a) the sample is blood, plasma, serum, urine or tissue, or a lipoprotein fraction thereof; and/or
b) the lipid concentrations, the lipid-lipid concentration ratio(s) or the lipid-clinical concentration ratio(s) is (are) determined by using mass spectrometry, nuclear magnetic resonance spectroscopy, fluorescence spectroscopy or dual polarization interferometry, a high performance separation method, an immunoassay and/or with a binding moiety capable of specifically binding the analyte.

11. The method of claim 1, wherein the one or more CVD complications are selected from CVD death and acute myocardial infarction (AMI).

12. The method of claim 2, wherein the one or more CVD complications are selected from CVD death and acute myocardial infarction (AMI).

13. The method of claim 1, wherein the subject is at risk to develop or has suffered from one or more CVD complications.

14. The method of claim 2, wherein the subject is at risk to develop or has suffered from one or more CVD complications.

15. The method of claim 1, wherein the control sample is from (a) coronary artery disease patient(s) (CAD) patient(s) or a group of CAD patients, wherein the CAD patient(s) or group of CAD patients has/have no history of major CVD events and is/are not undergoing statin treatment; wherein the control sample is blood, plasma, serum, urine or tissue, or a lipoprotein fraction thereof.

16. The method of claim 2, wherein the control sample is from (a) coronary artery disease patient(s) (CAD) patient(s) or a group of CAD patients, wherein the CAD patient(s) or group of CAD patients has/have no history of major CVD events and is/are not undergoing statin treatment; wherein the control sample is blood, plasma, serum, urine or tissue, or a lipoprotein fraction thereof.

17. The method of claim 9, further comprising a step of obtaining the sample from the subject.

18. The method of claim 10, further comprising a step of obtaining the sample from the subject.

19. The method of claim 9, further comprising a step of extracting lipids from the blood, serum, or plasma sample.

20. The method of claim 10, further comprising a step of extracting lipids from the blood, serum, or plasma sample.

21. The method of claim 9, wherein the one or more CVD complications are selected from CVD death and acute myocardial infarction (AMI).

22. The method of claim 10, wherein the one or more CVD complications are selected from CVD death and acute myocardial infarction (AMI).

23. The method of claim 1, wherein the method further comprises:
(d) treating the subject, if the determining steps indicate the subject has an increased risk of developing one or more CVD complications.

24. The method of claim 2, wherein the method further comprises:
(b) treating the subject, if the determining steps indicate the subject has an increased risk of developing one or more CVD complications.

25. The method of claim 23, wherein the treating comprises administering a lipid modifying treatment to the subject.

26. The method of claim 24, wherein the treating comprises administering a lipid modifying treatment to the subject.

27. A method of treating or preventing one or more CVD complications in a subject who is not undergoing statin treatment and who is not suffering from type 2 diabetes mellitus, the method comprising:
administering a treatment to the subject, wherein, prior to administering the treatment, the subject has been identified as being at risk to develop one or more CVD complications by the method according to claim 1.

28. A method of treating or preventing one or more CVD complications in a subject who is not undergoing statin treatment and who is suffering from type 2 diabetes mellitus, the method comprising:
administering a treatment to the subject, wherein, prior to administering the treatment, the subject has been identified as being at risk to develop one or more CVD complications by the method according to claim 2.

29. A method for detecting a lipid concentration, a lipid-lipid concentration ratio(s) and/or a lipid-clinical concentration ratio(s) in a sample from a coronary artery disease subject, comprising:
(a) assaying the sample from the coronary artery disease subject to detect the concentration of a lipid, wherein the lipid is Cer(d18:1/16:0);
(b) assaying the sample from the coronary artery disease subject to detect one or more lipid-lipid concentration ratio(s), wherein the one or more lipid-lipid concentration ratio(s) is (are) selected from: Cer(d18:1/16:0)/Cer (d18:1/24:0), Cer(d18:1/16:0)/Cer(d18:1/22:0), Cer(d18:1/16:0)/PC 18:0/22:6, Cer(d18:1/16:0)/PC 16:0/22:6, Cer(d18:1/18:0)/PC 16:0/22:6, Cer(d18:1/24:1)/PC 18:0/22:6, Cer(d18:1/20:0)/PC 16:0/22:6, Cer(d18:1/22:0)/PC 18:0/22:6, CE 16:0/Cer(d18:1/24:0), Cer(d18:1/18:0)/SM (d18:1/23:1)(d18:1/22:2-OH), Cer(d18:1/20:0)/SM (d18:1/23:1)(d18:1/22:2-0H), Cer(d18:1/24:0)/GlcCer(d18:1/18:0) and Cer(d18:1/24:0)/GlcCer(d18:1/16:0); and/or (c) assaying the sample from the coronary artery disease subject to detect one or more lipid-clinical concentration ratio(s), wherein the one or more lipid-clinical concentration ratio(s) is (are) selected from: Cer(d18:1/16:0)/HDL cholesterol, Cer(d18:1/16:0)/apolipoprotein B, Cer(d18:1/24:1)/supersensitive C-reactive protein and Cer(d18:1/22:0)/supersensitive C-reactive protein.

30. The method of claim 1, further comprising:

determining in a sample from said subject the concentration of a lipid, wherein an increased concentration in said sample, when compared to a control sample is indicative of said subject having an increased risk of developing one or more CVD complications, wherein the lipid whose increase in concentration is compared to the control is Cer(d18:1/16:0).

* * * * *